United States Patent
Henrik-Grinnemo et al.

(10) Patent No.: US 11,607,429 B2
(45) Date of Patent: Mar. 21, 2023

(54) DERIVATION AND SELF-RENEWAL OF ISl1+ CELLS AND USES THEREOF

(71) Applicant: Swedish StromaBio AB, Solna (SE)

(72) Inventors: Karl Henrik-Grinnemo, Hägersten (SE); Oscar Simonson, Stockholm (SE); Matthias Corbascio, Vallentuna (SE); Christer Sylvén, Bromma (SE); Eva Wärdell, Älvsjö (SE)

(73) Assignee: Swedish StromaBio AB, Solna (SE)

( * ) Notice: Subject to any disclaimer, the term of this patent is extended or adjusted under 35 U.S.C. 154(b) by 820 days.

(21) Appl. No.: 16/298,957

(22) Filed: Mar. 11, 2019

(65) Prior Publication Data

US 2019/0290700 A1    Sep. 26, 2019

Related U.S. Application Data

(62) Division of application No. 14/414,685, filed as application No. PCT/SE2013/000112 on Jul. 11, 2013, now Pat. No. 10,226,487.

(60) Provisional application No. 61/670,640, filed on Jul. 12, 2012.

(51) Int. Cl.
| | | |
|---|---|---|
| *A61K 35/34* | (2015.01) | |
| *C12N 5/0775* | (2010.01) | |
| *C12N 5/077* | (2010.01) | |

(52) U.S. Cl.
CPC ............ *A61K 35/34* (2013.01); *C12N 5/0657* (2013.01); *C12N 5/0668* (2013.01); *C12N 2501/40* (2013.01); *C12N 2501/415* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 10,226,487 B2 | 3/2019 | Grinnemo et al. | |
| 2010/0323443 A1 | 12/2010 | Domogatskaya et al. | |
| 2011/0305672 A1 | 12/2011 | Dalton et al. | |
| 2013/0280750 A1* | 10/2013 | Tryggvason | C12N 5/0668 435/459 |
| 2014/0315306 A1* | 10/2014 | Tryggvason | C12N 5/0668 435/377 |
| 2015/0164958 A1 | 6/2015 | Grinnemo et al. | |
| 2016/0122717 A1* | 5/2016 | Tryggvason | C12Q 1/6876 435/377 |
| 2018/0030415 A1* | 2/2018 | Nguyen | C12N 5/0672 |

FOREIGN PATENT DOCUMENTS

| | | |
|---|---|---|
| WO | 2007/016366 A2 | 2/2007 |
| WO | 2008/094597 A2 | 8/2008 |
| WO | 2010/011352 A2 | 1/2010 |

OTHER PUBLICATIONS

Bu et al, Nature Letters, 2009, vol. 460, pp. 113-117. (Year: 2009).*
Qyang et al, Cell Stem Cell, 2007, vol. 1, pp. 165-179. (Year: 2007).*
Final Office Action received for U.S. Appl. No. 14/414,685, dated May 5, 2017, 7 pages.
Genead et al., "Early First Trimester Human Embryonic Cardiac Islet-1 Progenitor Cells and Cardiomyocytes: Immunohistochemical and Electrophysiological Characterization", Stem Cell Research, vol. 4, Jan. 2010, pp. 69-76.
Genead et al., "Islet-1 Cells are Cardiac Progenitors Present During the Entire Lifespan: from the Embryonic Stage to Adulthood", Stem Cells and Development, vol. 19, No. 10, 2010, 2 pages.
International Preliminary Report on Patentability received for PCT Patent Application No. PCT/SE2013/000112, dated Jan. 22, 2015, 7 pages.
International Search Report and Written Opinion received for PCT Patent Application No. PCT/SE2013/000112, dated Nov. 22, 2013, 11 pages.
Klaus et al., "Wnt/β-Catenin and Bmp Signals Control Distinct Sets of Transcription Factors in Cardiac Progenitor Cells", PNAS, vol. 109, No. 27, Jul. 3, 2012, pp. 10921-10926.
Laugwitz et al., "Postnatal isl1+ Cardioblasts Enter Fully Differentiated Cardiomyocyte Lineages", Nature, vol. 433, Feb. 10, 2005, pp. 647-653.
Mittal et al., "Fibronectin and Integrin Alpha 5 Play Essential Roles in the Development of the Cardiac Neural Crest", Mechanisms of Development, vol. 127, 2010, pp. 472-484.
Non-Final Office Action received for U.S. Appl. No. 14/414,685, dated Dec. 14, 2017, 10 pages.
Non-Final Office Action received for U.S. Appl. No. 14/414,685, dated Aug. 24, 2016, 11 pages.
Notice of Allowance received for U.S. Appl. No. 14/414,685, dated Jul. 12, 2018, 7 pages.
Notice of Allowance received for U.S. Appl. No. 14/414,685, dated Nov. 7, 2018, 5 pages.
Genead et al., "Ischemia-Reperfusion Injury and Pregnancy Initiate Time-Dependent and Robust Signs of Up-Regulation of Cardiac Progenitor Cells", PLoS ONE, vol. 7, No. 5, May 2012, e36804, 11 pages.

* cited by examiner

*Primary Examiner* — Allison M Fox
(74) *Attorney, Agent, or Firm* — Morrison & Foerster LLP

(57) ABSTRACT

The present invention relates to methods for deriving multipotent Isl1+ cells (i.e. methods for inducing a cell to enter a multipotent Isl1+ lineage), methods for differentiating Isl1+ cells to cardiac cells, cells obtainable by such methods, kits and compositions for carrying out the methods in accordance with the invention, and also medical applications and pharmaceutical compositions of said cells.

2 Claims, 12 Drawing Sheets
Specification includes a Sequence Listing.

Initial Fraction 1 week 2 weeks

Differentiation

SEQUENCE LISTING

```
<160> NUMBER OF SEQ ID NOS: 6

<210> SEQ ID NO 1
<211> LENGTH: 3075
<212> TYPE: PRT
<213> ORGANISM: Homo sapiens

<400> SEQUENCE: 1

Met Arg Gly Gly Val Leu Leu Val Leu Leu Leu Cys Val Ala Ala Gln
1               5                   10                  15

Cys Arg Gln Arg Gly Leu Phe Pro Ala Ile Leu Asn Leu Ala Ser Asn
                20                  25                  30

Ala His Ile Ser Thr Asn Ala Thr Cys Gly Glu Lys Gly Pro Glu Met
            35                  40                  45
```

-continued

```
Phe Cys Lys Leu Val Glu His Val Pro Gly Arg Pro Val Arg Asn Pro
 50                  55                  60
Gln Cys Arg Ile Cys Asp Gly Asn Ser Ala Asn Pro Arg Glu Arg His
 65                  70                  75                  80
Pro Ile Ser His Ala Ile Asp Gly Thr Asn Asn Trp Trp Gln Ser Pro
                 85                  90                  95
Ser Ile Gln Asn Gly Arg Glu Tyr His Trp Val Thr Ile Thr Leu Asp
                100                 105                 110
Leu Arg Gln Val Phe Gln Val Ala Tyr Val Ile Ile Lys Ala Ala Asn
                115                 120                 125
Ala Pro Arg Pro Gly Asn Trp Ile Leu Glu Arg Ser Leu Asp Gly Thr
130                 135                 140
Thr Phe Ser Pro Trp Gln Tyr Ala Val Ser Asp Ser Glu Cys Leu
145                 150                 155                 160
Ser Arg Tyr Asn Ile Thr Pro Arg Arg Gly Pro Pro Thr Tyr Arg Ala
                165                 170                 175
Asp Asp Glu Val Ile Cys Thr Ser Tyr Tyr Ser Arg Leu Val Pro Leu
                180                 185                 190
Glu His Gly Glu Ile His Thr Ser Leu Ile Asn Gly Arg Pro Ser Ala
                195                 200                 205
Asp Asp Leu Ser Pro Lys Leu Leu Glu Phe Thr Ser Ala Arg Tyr Ile
210                 215                 220
Arg Leu Arg Leu Gln Arg Ile Arg Thr Leu Asn Ala Asp Leu Met Thr
225                 230                 235                 240
Leu Ser His Arg Glu Pro Lys Glu Leu Asp Pro Ile Val Thr Arg Arg
                245                 250                 255
Tyr Tyr Tyr Ser Ile Lys Asp Ile Ser Val Gly Gly Met Cys Ile Cys
                260                 265                 270
Tyr Gly His Ala Ser Ser Cys Pro Trp Asp Glu Thr Thr Lys Lys Leu
                275                 280                 285
Gln Cys Gln Cys Glu His Asn Thr Cys Gly Glu Ser Cys Asn Arg Cys
290                 295                 300
Cys Pro Gly Tyr His Gln Gln Pro Trp Arg Pro Gly Thr Val Ser Ser
305                 310                 315                 320
Gly Asn Thr Cys Glu Ala Cys Asn Cys His Asn Lys Ala Lys Asp Cys
                325                 330                 335
Tyr Tyr Asp Glu Ser Val Ala Lys Gln Lys Ser Leu Asn Thr Ala
                340                 345                 350
Gly Gln Phe Arg Gly Gly Val Cys Ile Asn Cys Leu Gln Asn Thr
                355                 360                 365
Met Gly Ile Asn Cys Glu Thr Cys Ile Asp Gly Tyr Tyr Arg Pro His
370                 375                 380
Lys Val Ser Pro Tyr Glu Asp Glu Pro Cys Arg Pro Cys Asn Cys Asp
385                 390                 395                 400
Pro Val Gly Ser Leu Ser Ser Val Cys Ile Lys Asp Asp Leu His Ser
                405                 410                 415
Asp Leu His Asn Gly Lys Gln Pro Gly Gln Cys Pro Cys Lys Glu Gly
                420                 425                 430
Tyr Thr Gly Glu Lys Cys Asp Arg Cys Gln Leu Gly Tyr Lys Asp Tyr
                435                 440                 445
Pro Thr Cys Val Ser Cys Gly Cys Asn Pro Val Gly Ser Ala Ser Asp
450                 455                 460
Glu Pro Cys Thr Gly Pro Cys Val Cys Lys Glu Asn Val Glu Gly Lys
```

-continued

```
            465                 470                 475                 480
        Ala Cys Asp Arg Cys Lys Pro Gly Phe Tyr Asn Leu Lys Glu Lys Asn
                        485                 490                 495
        Pro Arg Gly Cys Ser Glu Cys Phe Cys Phe Gly Val Ser Asp Val Cys
                        500                 505                 510
        Ser Ser Leu Ser Trp Pro Val Gly Gln Val Asn Ser Met Ser Gly Trp
                        515                 520                 525
        Leu Val Thr Asp Leu Ile Ser Pro Arg Lys Ile Pro Ser Gln Gln Asp
                        530                 535                 540
        Ala Leu Gly Gly Arg His Gln Val Ser Ile Asn Asn Thr Ala Val Met
        545                 550                 555                 560
        Gln Arg Leu Ala Pro Lys Tyr Tyr Trp Ala Ala Pro Glu Ala Tyr Leu
                        565                 570                 575
        Gly Asn Lys Leu Thr Ala Phe Gly Gly Phe Leu Lys Tyr Thr Val Ser
                        580                 585                 590
        Tyr Asp Ile Pro Val Glu Thr Val Asp Ser Asn Leu Met Ser His Ala
                        595                 600                 605
        Asp Val Ile Ile Lys Gly Asn Gly Leu Thr Leu Ser Thr Gln Ala Glu
                        610                 615                 620
        Gly Leu Ser Leu Gln Pro Tyr Glu Glu Tyr Leu Asn Val Val Arg Leu
        625                 630                 635                 640
        Val Pro Glu Asn Phe Gln Asp Phe His Ser Lys Arg Gln Ile Asp Arg
                        645                 650                 655
        Asp Gln Leu Met Thr Val Leu Ala Asn Val Thr His Leu Leu Ile Arg
                        660                 665                 670
        Ala Asn Tyr Asn Ser Ala Lys Met Ala Leu Tyr Arg Leu Glu Ser Val
                        675                 680                 685
        Ser Leu Asp Ile Ala Ser Ser Asn Ala Ile Asp Leu Val Val Ala Ala
                        690                 695                 700
        Asp Val Glu His Cys Glu Cys Pro Gln Gly Tyr Thr Gly Thr Ser Cys
        705                 710                 715                 720
        Glu Ser Cys Leu Ser Gly Tyr Tyr Arg Val Asp Gly Ile Leu Phe Gly
                        725                 730                 735
        Gly Ile Cys Gln Pro Cys Glu Cys His Gly His Ala Ala Glu Cys Asn
                        740                 745                 750
        Val His Gly Val Cys Ile Ala Cys Ala His Asn Thr Thr Gly Val His
                        755                 760                 765
        Cys Glu Gln Cys Leu Pro Gly Phe Tyr Gly Glu Pro Ser Arg Gly Thr
                        770                 775                 780
        Pro Gly Asp Cys Gln Pro Cys Ala Cys Pro Leu Thr Ile Ala Ser Asn
        785                 790                 795                 800
        Asn Phe Ser Pro Thr Cys His Leu Asn Asp Gly Asp Glu Val Val Cys
                        805                 810                 815
        Asp Trp Cys Ala Pro Gly Tyr Ser Gly Ala Trp Cys Glu Arg Cys Ala
                        820                 825                 830
        Asp Gly Tyr Tyr Gly Asn Pro Thr Val Pro Gly Glu Ser Cys Val Pro
                        835                 840                 845
        Cys Asp Cys Ser Gly Asn Val Asp Pro Ser Glu Ala Gly His Cys Asp
                        850                 855                 860
        Ser Val Thr Gly Glu Cys Leu Lys Cys Leu Gly Asn Thr Asp Gly Ala
        865                 870                 875                 880
        His Cys Glu Arg Cys Ala Asp Gly Phe Tyr Gly Asp Ala Val Thr Ala
                        885                 890                 895
```

-continued

Lys Asn Cys Arg Ala Cys Glu Cys His Val Lys Gly Ser His Ser Ala
        900                 905                 910

Val Cys His Leu Glu Thr Gly Leu Cys Asp Cys Lys Pro Asn Val Thr
        915                 920                 925

Gly Gln Gln Cys Asp Gln Cys Leu His Gly Tyr Tyr Gly Leu Asp Ser
        930                 935                 940

Gly His Gly Cys Arg Pro Cys Asn Cys Ser Val Ala Gly Ser Val Ser
945                 950                 955                 960

Asp Gly Cys Thr Asp Glu Gly Gln Cys His Cys Val Pro Gly Val Ala
                965                 970                 975

Gly Lys Arg Cys Asp Arg Cys Ala His Gly Phe Tyr Ala Tyr Gln Asp
        980                 985                 990

Gly Ser Cys Thr Pro Cys Asp Cys Pro His Thr Gln Asn Thr Cys Asp
        995                 1000                1005

Pro Glu Thr Gly Glu Cys Val Cys Pro Pro His Thr Gln Gly Val
        1010                1015                1020

Lys Cys Glu Glu Cys Glu Asp Gly His Trp Gly Tyr Asp Ala Glu
        1025                1030                1035

Val Gly Cys Gln Ala Cys Asn Cys Ser Leu Val Gly Ser Thr His
        1040                1045                1050

His Arg Cys Asp Val Val Thr Gly His Cys Gln Cys Lys Ser Lys
        1055                1060                1065

Phe Gly Gly Arg Ala Cys Asp Gln Cys Ser Leu Gly Tyr Arg Asp
        1070                1075                1080

Phe Pro Asp Cys Val Pro Cys Asp Cys Asp Leu Arg Gly Thr Ser
        1085                1090                1095

Gly Asp Ala Cys Asn Leu Glu Gln Gly Leu Cys Gly Cys Val Glu
        1100                1105                1110

Glu Thr Gly Ala Cys Pro Cys Lys Glu Asn Val Phe Gly Pro Gln
        1115                1120                1125

Cys Asn Glu Cys Arg Glu Gly Thr Phe Ala Leu Arg Ala Asp Asn
        1130                1135                1140

Pro Leu Gly Cys Ser Pro Cys Phe Cys Ser Gly Leu Ser His Leu
        1145                1150                1155

Cys Ser Glu Leu Glu Asp Tyr Val Arg Thr Pro Val Thr Leu Gly
        1160                1165                1170

Ser Asp Gln Pro Leu Leu Arg Val Val Ser Gln Ser Asn Leu Arg
        1175                1180                1185

Gly Thr Thr Glu Gly Val Tyr Tyr Gln Ala Pro Asp Phe Leu Leu
        1190                1195                1200

Asp Ala Ala Thr Val Arg Gln His Ile Arg Ala Glu Pro Phe Tyr
        1205                1210                1215

Trp Arg Leu Pro Gln Gln Phe Gln Gly Asp Gln Leu Met Ala Tyr
        1220                1225                1230

Gly Gly Lys Leu Lys Tyr Ser Val Ala Phe Tyr Ser Leu Asp Gly
        1235                1240                1245

Val Gly Thr Ser Asn Phe Glu Pro Gln Val Leu Ile Lys Gly Gly
        1250                1255                1260

Arg Ile Arg Lys Gln Val Ile Tyr Met Asp Ala Pro Ala Pro Glu
        1265                1270                1275

Asn Gly Val Arg Gln Glu Gln Glu Val Ala Met Arg Glu Asn Phe
        1280                1285                1290

-continued

```
Trp Lys Tyr Phe Asn Ser Val Ser Glu Lys Pro Val Thr Arg Glu
    1295                1300                1305

Asp Phe Met Ser Val Leu Ser Asp Ile Glu Tyr Ile Leu Ile Lys
    1310                1315                1320

Ala Ser Tyr Gly Gln Gly Leu Gln Gln Ser Arg Ile Ser Asp Ile
    1325                1330                1335

Ser Met Glu Val Gly Arg Lys Ala Glu Lys Leu His Pro Glu Glu
    1340                1345                1350

Glu Val Ala Ser Leu Leu Glu Asn Cys Val Cys Pro Pro Gly Thr
    1355                1360                1365

Val Gly Phe Ser Cys Gln Asp Cys Ala Pro Gly Tyr His Arg Gly
    1370                1375                1380

Lys Leu Pro Ala Gly Ser Asp Arg Gly Pro Arg Pro Leu Val Ala
    1385                1390                1395

Pro Cys Val Pro Cys Ser Cys Asn Asn His Ser Asp Thr Cys Asp
    1400                1405                1410

Pro Asn Thr Gly Lys Cys Leu Asn Cys Gly Asp Asn Thr Ala Gly
    1415                1420                1425

Asp His Cys Asp Val Cys Thr Ser Gly Tyr Tyr Gly Lys Val Thr
    1430                1435                1440

Gly Ser Ala Ser Asp Cys Ala Leu Cys Ala Cys Pro His Ser Pro
    1445                1450                1455

Pro Ala Ser Phe Ser Pro Thr Cys Val Leu Glu Gly Asp His Asp
    1460                1465                1470

Phe Arg Cys Asp Ala Cys Leu Leu Gly Tyr Glu Gly Lys His Cys
    1475                1480                1485

Glu Arg Cys Ser Ser Ser Tyr Tyr Gly Asn Pro Gln Thr Pro Gly
    1490                1495                1500

Gly Ser Cys Gln Lys Cys Asp Cys Asn Pro His Gly Ser Val His
    1505                1510                1515

Gly Asp Cys Asp Arg Thr Ser Gly Gln Cys Val Cys Arg Leu Gly
    1520                1525                1530

Ala Ser Gly Leu Arg Cys Asp Glu Cys Glu Pro Arg His Ile Leu
    1535                1540                1545

Met Glu Thr Asp Cys Val Ser Cys Asp Asp Glu Cys Val Gly Val
    1550                1555                1560

Leu Leu Asn Asp Leu Asp Glu Ile Gly Asp Ala Val Leu Ser Leu
    1565                1570                1575

Asn Leu Thr Gly Ile Ile Pro Val Pro Tyr Gly Ile Leu Ser Asn
    1580                1585                1590

Leu Glu Asn Thr Thr Lys Tyr Leu Gln Glu Ser Leu Leu Lys Glu
    1595                1600                1605

Asn Met Gln Lys Asp Leu Gly Lys Ile Lys Leu Glu Gly Val Ala
    1610                1615                1620

Glu Glu Thr Asp Asn Leu Gln Lys Lys Leu Thr Arg Met Leu Ala
    1625                1630                1635

Ser Thr Gln Lys Val Asn Arg Ala Thr Glu Arg Ile Phe Lys Glu
    1640                1645                1650

Ser Gln Asp Leu Ala Ile Ala Ile Glu Arg Leu Gln Met Ser Ile
    1655                1660                1665

Thr Glu Ile Met Glu Lys Thr Thr Leu Asn Gln Thr Leu Asp Glu
    1670                1675                1680

Asp Phe Leu Leu Pro Asn Ser Thr Leu Gln Asn Met Gln Gln Asn
```

-continued

```
            1685                1690                1695

Gly Thr Ser Leu Leu Glu Ile Met Gln Ile Arg Asp Phe Thr Gln
    1700                1705                1710

Leu His Gln Asn Ala Thr Leu Glu Leu Lys Ala Ala Glu Asp Leu
    1715                1720                1725

Leu Ser Gln Ile Gln Glu Asn Tyr Gln Lys Pro Leu Glu Glu Leu
    1730                1735                1740

Glu Val Leu Lys Glu Ala Ala Ser His Val Leu Ser Lys His Asn
    1745                1750                1755

Asn Glu Leu Lys Ala Ala Glu Ala Leu Val Arg Glu Ala Glu Ala
    1760                1765                1770

Lys Met Gln Glu Ser Asn His Leu Leu Leu Met Val Asn Ala Asn
    1775                1780                1785

Leu Arg Glu Phe Ser Asp Lys Lys Leu His Val Gln Glu Glu Gln
    1790                1795                1800

Asn Leu Thr Ser Glu Leu Ile Val Gln Gly Arg Gly Leu Ile Asp
    1805                1810                1815

Ala Ala Ala Ala Gln Thr Asp Ala Val Gln Asp Ala Leu Glu His
    1820                1825                1830

Leu Glu Asp His Gln Asp Lys Leu Leu Leu Trp Ser Ala Lys Ile
    1835                1840                1845

Arg His His Ile Asp Asp Leu Val Met His Met Ser Gln Arg Asn
    1850                1855                1860

Ala Val Asp Leu Val Tyr Arg Ala Glu Asp His Ala Ala Glu Phe
    1865                1870                1875

Gln Arg Leu Ala Asp Val Leu Tyr Ser Gly Leu Glu Asn Ile Arg
    1880                1885                1890

Asn Val Ser Leu Asn Ala Thr Ser Ala Ala Tyr Val His Tyr Asn
    1895                1900                1905

Ile Gln Ser Leu Ile Glu Glu Ser Glu Glu Leu Ala Arg Asp Ala
    1910                1915                1920

His Arg Thr Val Thr Glu Thr Ser Leu Leu Ser Glu Ser Leu Val
    1925                1930                1935

Ser Asn Gly Lys Ala Ala Val Gln Arg Ser Ser Arg Phe Leu Lys
    1940                1945                1950

Glu Gly Asn Asn Leu Ser Arg Lys Leu Pro Gly Ile Ala Leu Glu
    1955                1960                1965

Leu Ser Glu Leu Arg Asn Lys Thr Asn Arg Phe Gln Glu Asn Ala
    1970                1975                1980

Val Glu Ile Thr Arg Gln Thr Asn Glu Ser Leu Leu Ile Leu Arg
    1985                1990                1995

Ala Ile Pro Lys Gly Ile Arg Asp Lys Gly Ala Lys Thr Lys Glu
    2000                2005                2010

Leu Ala Thr Ser Ala Ser Gln Ser Ala Val Ser Thr Leu Arg Asp
    2015                2020                2025

Val Ala Gly Leu Ser Gln Glu Leu Leu Asn Thr Ser Ala Ser Leu
    2030                2035                2040

Ser Arg Val Asn Thr Thr Leu Arg Glu Thr His Gln Leu Leu Gln
    2045                2050                2055

Asp Ser Thr Met Ala Thr Leu Leu Ala Gly Arg Lys Val Lys Asp
    2060                2065                2070

Val Glu Ile Gln Ala Asn Leu Leu Phe Asp Arg Leu Lys Pro Leu
    2075                2080                2085
```

-continued

```
Lys Met Leu Glu Glu Asn Leu Ser Arg Asn Leu Ser Glu Ile Lys
    2090                2095                2100

Leu Leu Ile Ser Gln Ala Arg Lys Gln Ala Ala Ser Ile Lys Val
    2105                2110                2115

Ala Val Ser Ala Asp Arg Asp Cys Ile Arg Ala Tyr Gln Pro Gln
    2120                2125                2130

Ile Ser Ser Thr Asn Tyr Asn Thr Leu Thr Leu Asn Val Lys Thr
    2135                2140                2145

Gln Glu Pro Asp Asn Leu Leu Phe Tyr Leu Gly Ser Ser Thr Ala
    2150                2155                2160

Ser Asp Phe Leu Ala Val Glu Met Arg Arg Gly Arg Val Ala Phe
    2165                2170                2175

Leu Trp Asp Leu Gly Ser Gly Ser Thr Arg Leu Glu Phe Pro Asp
    2180                2185                2190

Phe Pro Ile Asp Asp Asn Arg Trp His Ser Ile His Val Ala Arg
    2195                2200                2205

Phe Gly Asn Ile Gly Ser Leu Ser Val Lys Glu Met Ser Ser Asn
    2210                2215                2220

Gln Lys Ser Pro Thr Lys Thr Ser Lys Ser Pro Gly Thr Ala Asn
    2225                2230                2235

Val Leu Asp Val Asn Asn Ser Thr Leu Met Phe Val Gly Gly Leu
    2240                2245                2250

Gly Gly Gln Ile Lys Lys Ser Pro Ala Val Lys Val Thr His Phe
    2255                2260                2265

Lys Gly Cys Leu Gly Glu Ala Phe Leu Asn Gly Lys Ser Ile Gly
    2270                2275                2280

Leu Trp Asn Tyr Ile Glu Arg Glu Gly Lys Cys Arg Gly Cys Phe
    2285                2290                2295

Gly Ser Ser Gln Asn Glu Asp Pro Ser Phe His Phe Asp Gly Ser
    2300                2305                2310

Gly Tyr Ser Val Val Glu Lys Ser Leu Pro Ala Thr Val Thr Gln
    2315                2320                2325

Ile Ile Met Leu Phe Asn Thr Phe Ser Pro Asn Gly Leu Leu Leu
    2330                2335                2340

Tyr Leu Gly Ser Tyr Gly Thr Lys Asp Phe Leu Ser Ile Glu Leu
    2345                2350                2355

Phe Arg Gly Arg Val Lys Val Met Thr Asp Leu Gly Ser Gly Pro
    2360                2365                2370

Ile Thr Leu Leu Thr Asp Arg Arg Tyr Asn Asn Gly Thr Trp Tyr
    2375                2380                2385

Lys Ile Ala Phe Gln Arg Asn Arg Lys Gln Gly Val Leu Ala Val
    2390                2395                2400

Ile Asp Ala Tyr Asn Thr Ser Asn Lys Glu Thr Lys Gln Gly Glu
    2405                2410                2415

Thr Pro Gly Ala Ser Ser Asp Leu Asn Arg Leu Asp Lys Asp Pro
    2420                2425                2430

Ile Tyr Val Gly Gly Leu Pro Arg Ser Arg Val Val Arg Arg Gly
    2435                2440                2445

Val Thr Thr Lys Ser Phe Val Gly Cys Ile Lys Asn Leu Glu Ile
    2450                2455                2460

Ser Arg Ser Thr Phe Asp Leu Leu Arg Asn Ser Tyr Gly Val Arg
    2465                2470                2475
```

```
Lys Gly Cys Leu Leu Glu Pro Ile Arg Ser Val Ser Phe Leu Lys
    2480                2485                2490

Gly Gly Tyr Ile Glu Leu Pro Pro Lys Ser Leu Ser Pro Glu Ser
    2495                2500                2505

Glu Trp Leu Val Thr Phe Ala Thr Thr Asn Ser Ser Gly Ile Ile
    2510                2515                2520

Leu Ala Ala Leu Gly Gly Asp Val Glu Lys Arg Gly Asp Arg Glu
    2525                2530                2535

Glu Ala His Val Pro Phe Phe Ser Val Met Leu Ile Gly Gly Asn
    2540                2545                2550

Ile Glu Val His Val Asn Pro Gly Asp Gly Thr Gly Leu Arg Lys
    2555                2560                2565

Ala Leu Leu His Ala Pro Thr Gly Thr Cys Ser Asp Gly Gln Ala
    2570                2575                2580

His Ser Ile Ser Leu Val Arg Asn Arg Arg Ile Ile Thr Val Gln
    2585                2590                2595

Leu Asp Glu Asn Asn Pro Val Glu Met Lys Leu Gly Thr Leu Val
    2600                2605                2610

Glu Ser Arg Thr Ile Asn Val Ser Asn Leu Tyr Val Gly Gly Ile
    2615                2620                2625

Pro Glu Gly Glu Gly Thr Ser Leu Leu Thr Met Arg Arg Ser Phe
    2630                2635                2640

His Gly Cys Ile Lys Asn Leu Ile Phe Asn Leu Glu Leu Leu Asp
    2645                2650                2655

Phe Asn Ser Ala Val Gly His Glu Gln Val Asp Leu Asp Thr Cys
    2660                2665                2670

Trp Leu Ser Glu Arg Pro Lys Leu Ala Pro Asp Ala Glu Asp Ser
    2675                2680                2685

Lys Leu Leu Pro Glu Pro Arg Ala Phe Pro Glu Gln Cys Val Val
    2690                2695                2700

Asp Ala Ala Leu Glu Tyr Val Pro Gly Ala His Gln Phe Gly Leu
    2705                2710                2715

Thr Gln Asn Ser His Phe Ile Leu Pro Phe Asn Gln Ser Ala Val
    2720                2725                2730

Arg Lys Lys Leu Ser Val Glu Leu Ser Ile Arg Thr Phe Ala Ser
    2735                2740                2745

Ser Gly Leu Ile Tyr Tyr Met Ala His Gln Asn Gln Ala Asp Tyr
    2750                2755                2760

Ala Val Leu Gln Leu His Gly Gly Arg Leu His Phe Met Phe Asp
    2765                2770                2775

Leu Gly Lys Gly Arg Thr Lys Val Ser His Pro Ala Leu Leu Ser
    2780                2785                2790

Asp Gly Lys Trp His Thr Val Lys Thr Asp Tyr Val Lys Arg Lys
    2795                2800                2805

Gly Phe Ile Thr Val Asp Gly Arg Glu Ser Pro Met Val Thr Val
    2810                2815                2820

Val Gly Asp Gly Thr Met Leu Asp Val Glu Gly Leu Phe Tyr Leu
    2825                2830                2835

Gly Gly Leu Pro Ser Gln Tyr Gln Ala Arg Lys Ile Gly Asn Ile
    2840                2845                2850

Thr His Ser Ile Pro Ala Cys Ile Gly Asp Val Thr Val Asn Ser
    2855                2860                2865

Lys Gln Leu Asp Lys Asp Ser Pro Val Ser Ala Phe Thr Val Asn
```

-continued

```
                2870                2875                2880
Arg Cys Tyr Ala Val Ala Gln Glu Gly Thr Tyr Phe Asp Gly Ser
    2885                2890                2895

Gly Tyr Ala Ala Leu Val Lys Glu Gly Tyr Lys Val Gln Ser Asp
    2900                2905                2910

Val Asn Ile Thr Leu Glu Phe Arg Thr Ser Ser Gln Asn Gly Val
    2915                2920                2925

Leu Leu Gly Ile Ser Thr Ala Lys Val Asp Ala Ile Gly Leu Glu
    2930                2935                2940

Leu Val Asp Gly Lys Val Leu Phe His Val Asn Asn Gly Ala Gly
    2945                2950                2955

Arg Ile Thr Ala Ala Tyr Glu Pro Lys Thr Ala Thr Val Leu Cys
    2960                2965                2970

Asp Gly Lys Trp His Thr Leu Gln Ala Asn Lys Ser Lys His Arg
    2975                2980                2985

Ile Thr Leu Ile Val Asp Gly Asn Ala Val Gly Ala Glu Ser Pro
    2990                2995                3000

His Thr Gln Ser Thr Ser Val Asp Thr Asn Asn Pro Ile Tyr Val
    3005                3010                3015

Gly Gly Tyr Pro Ala Gly Val Lys Gln Lys Cys Leu Arg Ser Gln
    3020                3025                3030

Thr Ser Phe Arg Gly Cys Leu Arg Lys Leu Ala Leu Ile Lys Ser
    3035                3040                3045

Pro Gln Val Gln Ser Phe Asp Phe Ser Arg Ala Phe Glu Leu His
    3050                3055                3060

Gly Val Phe Leu His Ser Cys Pro Gly Thr Glu Ser
    3065                3070                3075

<210> SEQ ID NO 2
<211> LENGTH: 3122
<212> TYPE: PRT
<213> ORGANISM: Homo sapiens

<400> SEQUENCE: 2

Met Pro Gly Ala Ala Gly Val Leu Leu Leu Leu Leu Ser Gly Gly
1               5                   10                  15

Leu Gly Gly Val Gln Ala Gln Arg Pro Gln Gln Gln Arg Gln Ser Gln
            20                  25                  30

Ala His Gln Gln Arg Gly Leu Phe Pro Ala Val Leu Asn Leu Ala Ser
        35                  40                  45

Asn Ala Leu Ile Thr Thr Asn Ala Thr Cys Gly Glu Lys Gly Pro Glu
    50                  55                  60

Met Tyr Cys Lys Leu Val Glu His Val Pro Gly Gln Pro Val Arg Asn
65                  70                  75                  80

Pro Gln Cys Arg Ile Cys Asn Gln Asn Ser Ser Asn Pro Asn Gln Arg
                85                  90                  95

His Pro Ile Thr Asn Ala Ile Asp Gly Lys Asn Thr Trp Trp Gln Ser
            100                 105                 110

Pro Ser Ile Lys Asn Gly Ile Glu Tyr His Tyr Val Thr Ile Thr Leu
        115                 120                 125

Asp Leu Gln Gln Val Phe Gln Ile Ala Tyr Val Ile Val Lys Ala Ala
    130                 135                 140

Asn Ser Pro Arg Pro Gly Asn Trp Ile Leu Glu Arg Ser Leu Asp Asp
145                 150                 155                 160
```

-continued

```
Val Glu Tyr Lys Pro Trp Gln Tyr His Ala Val Thr Asp Thr Glu Cys
                165                 170                 175

Leu Thr Leu Tyr Asn Ile Tyr Pro Arg Thr Gly Pro Pro Ser Tyr Ala
            180                 185                 190

Lys Asp Asp Glu Val Ile Cys Thr Ser Phe Tyr Ser Lys Ile His Pro
        195                 200                 205

Leu Glu Asn Gly Glu Ile His Ile Ser Leu Ile Asn Gly Arg Pro Ser
    210                 215                 220

Ala Asp Asp Pro Ser Pro Glu Leu Leu Glu Phe Thr Ser Ala Arg Tyr
225                 230                 235                 240

Ile Arg Leu Arg Phe Gln Arg Ile Arg Thr Leu Asn Ala Asp Leu Met
                245                 250                 255

Met Phe Ala His Lys Asp Pro Arg Glu Ile Asp Pro Ile Val Thr Arg
            260                 265                 270

Arg Tyr Tyr Ser Val Lys Asp Ile Ser Val Gly Gly Met Cys Ile
        275                 280                 285

Cys Tyr Gly His Ala Arg Ala Cys Pro Leu Asp Pro Ala Thr Asn Lys
    290                 295                 300

Ser Arg Cys Glu Cys Glu His Asn Thr Cys Gly Asp Ser Cys Asp Gln
305                 310                 315                 320

Cys Cys Pro Gly Phe His Gln Lys Pro Trp Arg Ala Gly Thr Phe Leu
                325                 330                 335

Thr Lys Thr Glu Cys Glu Ala Cys Asn Cys His Gly Lys Ala Glu Glu
            340                 345                 350

Cys Tyr Tyr Asp Glu Asn Val Ala Arg Arg Asn Leu Ser Leu Asn Ile
        355                 360                 365

Arg Gly Lys Tyr Ile Gly Gly Val Cys Ile Asn Cys Thr Gln Asn
    370                 375                 380

Thr Ala Gly Ile Asn Cys Glu Thr Cys Thr Asp Gly Phe Phe Arg Pro
385                 390                 395                 400

Lys Gly Val Ser Pro Asn Tyr Pro Arg Pro Cys Gln Pro Cys His Cys
                405                 410                 415

Asp Pro Ile Gly Ser Leu Asn Glu Val Cys Val Lys Asp Glu Lys His
            420                 425                 430

Ala Arg Arg Gly Leu Ala Pro Gly Ser Cys His Cys Lys Thr Gly Phe
        435                 440                 445

Gly Gly Val Ser Cys Asp Arg Cys Ala Arg Gly Tyr Thr Gly Tyr Pro
    450                 455                 460

Asp Cys Lys Ala Cys Asn Cys Ser Gly Leu Gly Ser Lys Asn Glu Asp
465                 470                 475                 480

Pro Cys Phe Gly Pro Cys Ile Cys Lys Glu Asn Val Glu Gly Asp
                485                 490                 495

Cys Ser Arg Cys Lys Ser Gly Phe Phe Asn Leu Gln Glu Asp Asn Trp
            500                 505                 510

Lys Gly Cys Asp Glu Cys Phe Cys Ser Gly Val Ser Asn Arg Cys Gln
        515                 520                 525

Ser Ser Tyr Trp Thr Tyr Gly Lys Ile Gln Asp Met Ser Gly Trp Tyr
    530                 535                 540

Leu Thr Asp Leu Pro Gly Arg Ile Arg Val Ala Pro Gln Gln Asp Asp
545                 550                 555                 560

Leu Asp Ser Pro Gln Gln Ile Ser Ile Ser Asn Ala Glu Ala Arg Gln
                565                 570                 575

Ala Leu Pro His Ser Tyr Tyr Trp Ser Ala Pro Ala Pro Tyr Leu Gly
```

-continued

```
            580                 585                 590
Asn Lys Leu Pro Ala Val Gly Gly Gln Leu Thr Phe Thr Ile Ser Tyr
            595                 600                 605
Asp Leu Glu Glu Glu Glu Asp Thr Glu Arg Val Leu Gln Leu Met
    610                 615                 620
Ile Ile Leu Glu Gly Asn Asp Leu Ser Ile Ser Thr Ala Gln Asp Glu
625                 630                 635                 640
Val Tyr Leu His Pro Ser Glu His Thr Asn Val Leu Leu Leu Lys
            645                 650                 655
Glu Glu Ser Phe Thr Ile His Gly Thr His Phe Pro Val Arg Arg Lys
            660                 665                 670
Glu Phe Met Thr Val Leu Ala Asn Leu Lys Arg Val Leu Leu Gln Ile
            675                 680                 685
Thr Tyr Ser Phe Gly Met Asp Ala Ile Phe Arg Leu Ser Ser Val Asn
            690                 695                 700
Leu Glu Ser Ala Val Ser Tyr Pro Thr Asp Gly Ser Ile Ala Ala Ala
705                 710                 715                 720
Val Glu Val Cys Gln Cys Pro Pro Gly Tyr Thr Gly Ser Ser Cys Glu
            725                 730                 735
Ser Cys Trp Pro Arg His Arg Arg Val Asn Gly Thr Ile Phe Gly Gly
            740                 745                 750
Ile Cys Glu Pro Cys Gln Cys Phe Gly His Ala Glu Ser Cys Asp Asp
            755                 760                 765
Val Thr Gly Glu Cys Leu Asn Cys Lys Asp His Thr Gly Gly Pro Tyr
770                 775                 780
Cys Asp Lys Cys Leu Pro Gly Phe Tyr Gly Glu Pro Thr Lys Gly Thr
785                 790                 795                 800
Ser Glu Asp Cys Gln Pro Cys Ala Cys Pro Leu Asn Ile Pro Ser Asn
            805                 810                 815
Asn Phe Ser Pro Thr Cys His Leu Asp Arg Ser Leu Gly Leu Ile Cys
            820                 825                 830
Asp Gly Cys Pro Val Gly Tyr Thr Gly Pro Arg Cys Glu Arg Cys Ala
            835                 840                 845
Glu Gly Tyr Phe Gly Gln Pro Ser Val Pro Gly Gly Ser Cys Gln Pro
            850                 855                 860
Cys Gln Cys Asn Asp Asn Leu Asp Phe Ser Ile Pro Gly Ser Cys Asp
865                 870                 875                 880
Ser Leu Ser Gly Ser Cys Leu Ile Cys Lys Pro Gly Thr Thr Gly Arg
            885                 890                 895
Tyr Cys Glu Leu Cys Ala Asp Gly Tyr Phe Gly Asp Ala Val Asp Ala
            900                 905                 910
Lys Asn Cys Gln Pro Cys Arg Cys Asn Ala Gly Gly Ser Phe Ser Glu
            915                 920                 925
Val Cys His Ser Gln Thr Gly Gln Cys Glu Cys Arg Ala Asn Val Gln
            930                 935                 940
Gly Gln Arg Cys Asp Lys Cys Lys Ala Gly Thr Phe Gly Leu Gln Ser
945                 950                 955                 960
Ala Arg Gly Cys Val Pro Cys Asn Cys Asn Ser Phe Gly Ser Lys Ser
            965                 970                 975
Phe Asp Cys Glu Glu Ser Gly Gln Cys Trp Cys Gln Pro Gly Val Thr
            980                 985                 990
Gly Lys Lys Cys Asp Arg Cys Ala  His Gly Tyr Phe Asn  Phe Gln Glu
            995                 1000                1005
```

```
Gly Gly Cys Thr Ala Cys Glu Cys Ser His Leu Gly Asn Asn Cys
1010            1015            1020

Asp Pro Lys Thr Gly Arg Cys Ile Cys Pro Pro Asn Thr Ile Gly
1025            1030            1035

Glu Lys Cys Ser Lys Cys Ala Pro Asn Thr Trp Gly His Ser Ile
1040            1045            1050

Thr Thr Gly Cys Lys Ala Cys Asn Cys Ser Thr Val Gly Ser Leu
1055            1060            1065

Asp Phe Gln Cys Asn Val Asn Thr Gly Gln Cys Asn Cys His Pro
1070            1075            1080

Lys Phe Ser Gly Ala Lys Cys Thr Glu Cys Ser Arg Gly His Trp
1085            1090            1095

Asn Tyr Pro Arg Cys Asn Leu Cys Asp Cys Phe Leu Pro Gly Thr
1100            1105            1110

Asp Ala Thr Thr Cys Asp Ser Glu Thr Lys Lys Cys Ser Cys Ser
1115            1120            1125

Asp Gln Thr Gly Gln Cys Thr Cys Lys Val Asn Val Glu Gly Ile
1130            1135            1140

His Cys Asp Arg Cys Arg Pro Gly Lys Phe Gly Leu Asp Ala Lys
1145            1150            1155

Asn Pro Leu Gly Cys Ser Ser Cys Tyr Cys Phe Gly Thr Thr Thr
1160            1165            1170

Gln Cys Ser Glu Ala Lys Gly Leu Ile Arg Thr Trp Val Thr Leu
1175            1180            1185

Lys Ala Glu Gln Thr Ile Leu Pro Leu Val Asp Glu Ala Leu Gln
1190            1195            1200

His Thr Thr Thr Lys Gly Ile Val Phe Gln His Pro Glu Ile Val
1205            1210            1215

Ala His Met Asp Leu Met Arg Glu Asp Leu His Leu Glu Pro Phe
1220            1225            1230

Tyr Trp Lys Leu Pro Glu Gln Phe Glu Gly Lys Lys Leu Met Ala
1235            1240            1245

Tyr Gly Gly Lys Leu Lys Tyr Ala Ile Tyr Phe Glu Ala Arg Glu
1250            1255            1260

Glu Thr Gly Phe Ser Thr Tyr Asn Pro Gln Val Ile Ile Arg Gly
1265            1270            1275

Gly Thr Pro Thr His Ala Arg Ile Ile Val Arg His Met Ala Ala
1280            1285            1290

Pro Leu Ile Gly Gln Leu Thr Arg His Glu Ile Glu Met Thr Glu
1295            1300            1305

Lys Glu Trp Lys Tyr Tyr Gly Asp Asp Pro Arg Val His Arg Thr
1310            1315            1320

Val Thr Arg Glu Asp Phe Leu Asp Ile Leu Tyr Asp Ile His Tyr
1325            1330            1335

Ile Leu Ile Lys Ala Thr Tyr Gly Asn Phe Met Arg Gln Ser Arg
1340            1345            1350

Ile Ser Glu Ile Ser Met Glu Val Ala Glu Gln Gly Arg Gly Thr
1355            1360            1365

Thr Met Thr Pro Pro Ala Asp Leu Ile Glu Lys Cys Asp Cys Pro
1370            1375            1380

Leu Gly Tyr Ser Gly Leu Ser Cys Glu Ala Cys Leu Pro Gly Phe
1385            1390            1395
```

-continued

Tyr Arg Leu Arg Ser Gln Pro Gly Gly Arg Thr Pro Gly Pro Thr
1400                    1405                1410

Leu Gly Thr Cys Val Pro Cys Gln Cys Asn Gly His Ser Ser Leu
1415                    1420                1425

Cys Asp Pro Glu Thr Ser Ile Cys Gln Asn Cys Gln His His Thr
1430                    1435                1440

Ala Gly Asp Phe Cys Glu Arg Cys Ala Leu Gly Tyr Tyr Gly Ile
1445                    1450                1455

Val Lys Gly Leu Pro Asn Asp Cys Gln Gln Cys Ala Cys Pro Leu
1460                    1465                1470

Ile Ser Ser Ser Asn Asn Phe Ser Pro Ser Cys Val Ala Glu Gly
1475                    1480                1485

Leu Asp Asp Tyr Arg Cys Thr Ala Cys Pro Arg Gly Tyr Glu Gly
1490                    1495                1500

Gln Tyr Cys Glu Arg Cys Ala Pro Gly Tyr Thr Gly Ser Pro Gly
1505                    1510                1515

Asn Pro Gly Gly Ser Cys Gln Glu Cys Glu Cys Asp Pro Tyr Gly
1520                    1525                1530

Ser Leu Pro Val Pro Cys Asp Pro Val Thr Gly Phe Cys Thr Cys
1535                    1540                1545

Arg Pro Gly Ala Thr Gly Arg Lys Cys Asp Gly Cys Lys His Trp
1550                    1555                1560

His Ala Arg Glu Gly Trp Glu Cys Val Phe Cys Gly Asp Glu Cys
1565                    1570                1575

Thr Gly Leu Leu Leu Gly Asp Leu Ala Arg Leu Glu Gln Met Val
1580                    1585                1590

Met Ser Ile Asn Leu Thr Gly Pro Leu Pro Ala Pro Tyr Lys Met
1595                    1600                1605

Leu Tyr Gly Leu Glu Asn Met Thr Gln Glu Leu Lys His Leu Leu
1610                    1615                1620

Ser Pro Gln Arg Ala Pro Glu Arg Leu Ile Gln Leu Ala Glu Gly
1625                    1630                1635

Asn Leu Asn Thr Leu Val Thr Glu Met Asn Glu Leu Leu Thr Arg
1640                    1645                1650

Ala Thr Lys Val Thr Ala Asp Gly Glu Gln Thr Gly Gln Asp Ala
1655                    1660                1665

Glu Arg Thr Asn Thr Arg Ala Lys Ser Leu Gly Glu Phe Ile Lys
1670                    1675                1680

Glu Leu Ala Arg Asp Ala Glu Ala Val Asn Glu Lys Ala Ile Lys
1685                    1690                1695

Leu Asn Glu Thr Leu Gly Thr Arg Asp Glu Ala Phe Glu Arg Asn
1700                    1705                1710

Leu Glu Gly Leu Gln Lys Glu Ile Asp Gln Met Ile Lys Glu Leu
1715                    1720                1725

Arg Arg Lys Asn Leu Glu Thr Gln Lys Glu Ile Ala Glu Asp Glu
1730                    1735                1740

Leu Val Ala Ala Glu Ala Leu Leu Lys Lys Val Lys Lys Leu Phe
1745                    1750                1755

Gly Glu Ser Arg Gly Glu Asn Glu Glu Met Glu Lys Asp Leu Arg
1760                    1765                1770

Glu Lys Leu Ala Asp Tyr Lys Asn Lys Val Asp Asp Ala Trp Asp
1775                    1780                1785

Leu Leu Arg Glu Ala Thr Asp Lys Ile Arg Glu Ala Asn Arg Leu

```
              1790                1795                1800

Phe Ala Val Asn Gln Lys Asn Met Thr Ala Leu Glu Lys Lys Lys
    1805                1810                1815

Glu Ala Val Glu Ser Gly Lys Arg Gln Ile Glu Asn Thr Leu Lys
    1820                1825                1830

Glu Gly Asn Asp Ile Leu Asp Glu Ala Asn Arg Leu Ala Asp Glu
    1835                1840                1845

Ile Asn Ser Ile Ile Asp Tyr Val Glu Asp Ile Gln Thr Lys Leu
    1850                1855                1860

Pro Pro Met Ser Glu Glu Leu Asn Asp Lys Ile Asp Asp Leu Ser
    1865                1870                1875

Gln Glu Ile Lys Asp Arg Lys Leu Ala Glu Lys Val Ser Gln Ala
    1880                1885                1890

Glu Ser His Ala Ala Gln Leu Asn Asp Ser Ser Ala Val Leu Asp
    1895                1900                1905

Gly Ile Leu Asp Glu Ala Lys Asn Ile Ser Phe Asn Ala Thr Ala
    1910                1915                1920

Ala Phe Lys Ala Tyr Ser Asn Ile Lys Asp Tyr Ile Asp Glu Ala
    1925                1930                1935

Glu Lys Val Ala Lys Glu Ala Lys Asp Leu Ala His Glu Ala Thr
    1940                1945                1950

Lys Leu Ala Thr Gly Pro Arg Gly Leu Leu Lys Glu Asp Ala Lys
    1955                1960                1965

Gly Cys Leu Gln Lys Ser Phe Arg Ile Leu Asn Glu Ala Lys Lys
    1970                1975                1980

Leu Ala Asn Asp Val Lys Glu Asn Glu Asp His Leu Asn Gly Leu
    1985                1990                1995

Lys Thr Arg Ile Glu Asn Ala Asp Ala Arg Asn Gly Asp Leu Leu
    2000                2005                2010

Arg Thr Leu Asn Asp Thr Leu Gly Lys Leu Ser Ala Ile Pro Asn
    2015                2020                2025

Asp Thr Ala Ala Lys Leu Gln Ala Val Lys Asp Lys Ala Arg Gln
    2030                2035                2040

Ala Asn Asp Thr Ala Lys Asp Val Leu Ala Gln Ile Thr Glu Leu
    2045                2050                2055

His Gln Asn Leu Asp Gly Leu Lys Lys Asn Tyr Asn Lys Leu Ala
    2060                2065                2070

Asp Ser Val Ala Lys Thr Asn Ala Val Val Lys Asp Pro Ser Lys
    2075                2080                2085

Asn Lys Ile Ile Ala Asp Ala Asp Ala Thr Val Lys Asn Leu Glu
    2090                2095                2100

Gln Glu Ala Asp Arg Leu Ile Asp Lys Leu Lys Pro Ile Lys Glu
    2105                2110                2115

Leu Glu Asp Asn Leu Lys Lys Asn Ile Ser Glu Ile Lys Glu Leu
    2120                2125                2130

Ile Asn Gln Ala Arg Lys Gln Ala Asn Ser Ile Lys Val Ser Val
    2135                2140                2145

Ser Ser Gly Gly Asp Cys Ile Arg Thr Tyr Lys Pro Glu Ile Lys
    2150                2155                2160

Lys Gly Ser Tyr Asn Asn Ile Val Val Asn Val Lys Thr Ala Val
    2165                2170                2175

Ala Asp Asn Leu Leu Phe Tyr Leu Gly Ser Ala Lys Phe Ile Asp
    2180                2185                2190
```

```
Phe Leu Ala Ile Glu Met Arg Lys Gly Lys Val Ser Phe Leu Trp
    2195            2200            2205

Asp Val Gly Ser Gly Val Gly Arg Val Glu Tyr Pro Asp Leu Thr
    2210            2215            2220

Ile Asp Asp Ser Tyr Trp Tyr Arg Ile Val Ala Ser Arg Thr Gly
    2225            2230            2235

Arg Asn Gly Thr Ile Ser Val Arg Ala Leu Asp Gly Pro Lys Ala
    2240            2245            2250

Ser Ile Val Pro Ser Thr His His Ser Thr Pro Pro Gly Tyr
    2255            2260            2265

Thr Ile Leu Asp Val Asp Ala Asn Ala Met Leu Phe Val Gly Gly
    2270            2275            2280

Leu Thr Gly Lys Leu Lys Lys Ala Asp Ala Val Arg Val Ile Thr
    2285            2290            2295

Phe Thr Gly Cys Met Gly Glu Thr Tyr Phe Asp Asn Lys Pro Ile
    2300            2305            2310

Gly Leu Trp Asn Phe Arg Glu Lys Glu Gly Asp Cys Lys Gly Cys
    2315            2320            2325

Thr Val Ser Pro Gln Val Glu Asp Ser Glu Gly Thr Ile Gln Phe
    2330            2335            2340

Asp Gly Glu Gly Tyr Ala Leu Val Ser Arg Pro Ile Arg Trp Tyr
    2345            2350            2355

Pro Asn Ile Ser Thr Val Met Phe Lys Phe Arg Thr Phe Ser Ser
    2360            2365            2370

Ser Ala Leu Leu Met Tyr Leu Ala Thr Arg Asp Leu Arg Asp Phe
    2375            2380            2385

Met Ser Val Glu Leu Thr Asp Gly His Ile Lys Val Ser Tyr Asp
    2390            2395            2400

Leu Gly Ser Gly Met Ala Ser Val Val Ser Asn Gln Asn His Asn
    2405            2410            2415

Asp Gly Lys Trp Lys Ser Phe Thr Leu Ser Arg Ile Gln Lys Gln
    2420            2425            2430

Ala Asn Ile Ser Ile Val Asp Ile Asp Thr Asn Gln Glu Glu Asn
    2435            2440            2445

Ile Ala Thr Ser Ser Ser Gly Asn Asn Phe Gly Leu Asp Leu Lys
    2450            2455            2460

Ala Asp Asp Lys Ile Tyr Phe Gly Gly Leu Pro Thr Leu Arg Asn
    2465            2470            2475

Leu Ser Met Lys Ala Arg Pro Glu Val Asn Leu Lys Lys Tyr Ser
    2480            2485            2490

Gly Cys Leu Lys Asp Ile Glu Ile Ser Arg Thr Pro Tyr Asn Ile
    2495            2500            2505

Leu Ser Ser Pro Asp Tyr Val Gly Val Thr Lys Gly Cys Ser Leu
    2510            2515            2520

Glu Asn Val Tyr Thr Val Ser Phe Pro Lys Pro Gly Phe Val Glu
    2525            2530            2535

Leu Ser Pro Val Pro Ile Asp Val Gly Thr Glu Ile Asn Leu Ser
    2540            2545            2550

Phe Ser Thr Lys Asn Glu Ser Gly Ile Ile Leu Leu Gly Ser Gly
    2555            2560            2565

Gly Thr Pro Ala Pro Pro Arg Arg Lys Arg Arg Gln Thr Gly Gln
    2570            2575            2580
```

| | | | | | | | | | | |
|---|---|---|---|---|---|---|---|---|---|---|
|Ala|Tyr|Tyr|Val|Ile|Leu|Leu|Asn|Arg|Gly|Arg|Leu|Glu|Val|His|
|2585| | | | |2590| | | | |2595| | | | |

Leu Ser Thr Gly Ala Arg Thr Met Arg Lys Ile Val Ile Arg Pro
2600                2605                2610

Glu Pro Asn Leu Phe His Asp Gly Arg Glu His Ser Val His Val
2615                2620                2625

Glu Arg Thr Arg Gly Ile Phe Thr Val Gln Val Asp Glu Asn Arg
2630                2635                2640

Arg Tyr Met Gln Asn Leu Thr Val Glu Gln Pro Ile Glu Val Lys
2645                2650                2655

Lys Leu Phe Val Gly Gly Ala Pro Pro Glu Phe Gln Pro Ser Pro
2660                2665                2670

Leu Arg Asn Ile Pro Pro Phe Glu Gly Cys Ile Trp Asn Leu Val
2675                2680                2685

Ile Asn Ser Val Pro Met Asp Phe Ala Arg Pro Val Ser Phe Lys
2690                2695                2700

Asn Ala Asp Ile Gly Arg Cys Ala His Gln Lys Leu Arg Glu Asp
2705                2710                2715

Glu Asp Gly Ala Ala Pro Ala Glu Ile Val Ile Gln Pro Glu Pro
2720                2725                2730

Val Pro Thr Pro Ala Phe Pro Thr Pro Thr Pro Val Leu Thr His
2735                2740                2745

Gly Pro Cys Ala Ala Glu Ser Glu Pro Ala Leu Leu Ile Gly Ser
2750                2755                2760

Lys Gln Phe Gly Leu Ser Arg Asn Ser His Ile Ala Ile Ala Phe
2765                2770                2775

Asp Asp Thr Lys Val Lys Asn Arg Leu Thr Ile Glu Leu Glu Val
2780                2785                2790

Arg Thr Glu Ala Glu Ser Gly Leu Leu Phe Tyr Met Ala Arg Ile
2795                2800                2805

Asn His Ala Asp Phe Ala Thr Val Gln Leu Arg Asn Gly Leu Pro
2810                2815                2820

Tyr Phe Ser Tyr Asp Leu Gly Ser Gly Asp Thr His Thr Met Ile
2825                2830                2835

Pro Thr Lys Ile Asn Asp Gly Gln Trp His Lys Ile Lys Ile Met
2840                2845                2850

Arg Ser Lys Gln Glu Gly Ile Leu Tyr Val Asp Gly Ala Ser Asn
2855                2860                2865

Arg Thr Ile Ser Pro Lys Lys Ala Asp Ile Leu Asp Val Val Gly
2870                2875                2880

Met Leu Tyr Val Gly Gly Leu Pro Ile Asn Tyr Thr Thr Arg Arg
2885                2890                2895

Ile Gly Pro Val Thr Tyr Ser Ile Asp Gly Cys Val Arg Asn Leu
2900                2905                2910

His Met Ala Glu Ala Pro Ala Asp Leu Glu Gln Pro Thr Ser Ser
2915                2920                2925

Phe His Val Gly Thr Cys Phe Ala Asn Ala Gln Arg Gly Thr Tyr
2930                2935                2940

Phe Asp Gly Thr Gly Phe Ala Lys Ala Val Gly Gly Phe Lys Val
2945                2950                2955

Gly Leu Asp Leu Leu Val Glu Phe Glu Phe Arg Thr Thr Thr Thr
2960                2965                2970

Thr Gly Val Leu Leu Gly Ile Ser Ser Gln Lys Met Asp Gly Met

```
                      2975                2980                2985
Gly Ile Glu Met Ile Asp Glu Lys Leu Met Phe His Val Asp Asn
    2990                2995                3000
Gly Ala Gly Arg Phe Thr Ala Val Tyr Asp Ala Gly Val Pro Gly
    3005                3010                3015
His Leu Cys Asp Gly Gln Trp His Lys Val Thr Ala Asn Lys Ile
    3020                3025                3030
Lys His Arg Ile Glu Leu Thr Val Asp Gly Asn Gln Val Glu Ala
    3035                3040                3045
Gln Ser Pro Asn Pro Ala Ser Thr Ser Ala Asp Thr Asn Asp Pro
    3050                3055                3060
Val Phe Val Gly Gly Phe Pro Asp Asp Leu Lys Gln Phe Gly Leu
    3065                3070                3075
Thr Thr Ser Ile Pro Phe Arg Gly Cys Ile Arg Ser Leu Lys Leu
    3080                3085                3090
Thr Lys Gly Thr Gly Lys Pro Leu Glu Val Asn Phe Ala Lys Ala
    3095                3100                3105
Leu Glu Leu Arg Gly Val Gln Pro Val Ser Cys Pro Ala Asn
    3110                3115                3120

<210> SEQ ID NO 3
<211> LENGTH: 3695
<212> TYPE: PRT
<213> ORGANISM: Homo sapiens

<400> SEQUENCE: 3

Met Ala Lys Arg Leu Cys Ala Gly Ser Ala Leu Cys Val Arg Gly Pro
1               5                   10                  15
Arg Gly Pro Ala Pro Leu Leu Leu Val Gly Leu Ala Leu Leu Gly Ala
            20                  25                  30
Ala Arg Ala Arg Glu Glu Ala Gly Gly Phe Ser Leu His Pro Pro
        35                  40                  45
Tyr Phe Asn Leu Ala Glu Gly Ala Arg Ile Ala Ala Ser Ala Thr Cys
50                  55                  60
Gly Glu Glu Ala Pro Ala Arg Gly Ser Pro Arg Pro Thr Glu Asp Leu
65                  70                  75                  80
Tyr Cys Lys Leu Val Gly Gly Pro Val Ala Gly Asp Pro Asn Gln
                85                  90                  95
Thr Ile Arg Gly Gln Tyr Cys Asp Ile Cys Thr Ala Ala Asn Ser Asn
            100                 105                 110
Lys Ala His Pro Ala Ser Asn Ala Ile Asp Gly Thr Glu Arg Trp Trp
        115                 120                 125
Gln Ser Pro Pro Leu Ser Arg Gly Leu Glu Tyr Asn Glu Val Asn Val
    130                 135                 140
Thr Leu Asp Leu Gly Gln Val Phe His Val Ala Tyr Val Leu Ile Lys
145                 150                 155                 160
Phe Ala Asn Ser Pro Arg Pro Asp Leu Trp Val Leu Glu Arg Ser Met
                165                 170                 175
Asp Phe Gly Arg Thr Tyr Gln Pro Trp Gln Phe Phe Ala Ser Ser Lys
            180                 185                 190
Arg Asp Cys Leu Glu Arg Phe Gly Pro Gln Thr Leu Glu Arg Ile Thr
        195                 200                 205
Arg Asp Asp Ala Ala Ile Cys Thr Thr Glu Tyr Ser Arg Ile Val Pro
    210                 215                 220
```

```
Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
    290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Thr Cys Asp Arg Cys
                325                 330                 335

Cys Pro Gly Phe Asn Gln Gln Pro Trp Lys Pro Ala Thr Ala Asn Ser
                340                 345                 350

Ala Asn Glu Cys Gln Ser Cys Asn Cys Tyr Gly His Ala Thr Asp Cys
            355                 360                 365

Tyr Tyr Asp Pro Glu Val Asp Arg Arg Arg Ala Ser Gln Ser Leu Asp
    370                 375                 380

Gly Thr Tyr Gln Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
                420                 425                 430

Ser Asp Phe Thr Asp Gly Thr Cys Glu Asp Leu Thr Gly Arg Cys Tyr
            435                 440                 445

Cys Arg Pro Asn Phe Ser Gly Glu Arg Cys Asp Val Cys Ala Glu Gly
    450                 455                 460

Phe Thr Gly Phe Pro Ser Cys Tyr Pro Thr Pro Ser Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
        515                 520                 525

Cys Ala Pro Gly Phe Tyr Gly Pro Gly Cys Gln Pro Cys Gln Cys Ser
    530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575

Gly Tyr Phe His Phe Pro Leu Cys Gln Leu Cys Gly Cys Ser Pro Ala
                580                 585                 590

Gly Thr Leu Pro Glu Gly Cys Asp Glu Ala Gly Arg Cys Leu Cys Gln
            595                 600                 605

Pro Glu Phe Ala Gly Pro His Cys Asp Arg Cys Arg Pro Gly Tyr His
        610                 615                 620

Gly Phe Pro Asn Cys Gln Ala Cys Thr Cys Asp Pro Arg Gly Ala Leu
    625                 630                 635                 640

Asp Gln Leu Cys Gly Ala Gly Gly Leu Cys Arg Cys Arg Pro Gly Tyr
```

-continued

```
                645                 650                 655
Thr Gly Thr Ala Cys Gln Glu Cys Ser Pro Gly Phe His Gly Phe Pro
                660                 665                 670

Ser Cys Val Pro Cys His Cys Ser Ala Glu Gly Ser Leu His Ala Ala
                675                 680                 685

Cys Asp Pro Arg Ser Gly Gln Cys Ser Cys Arg Pro Arg Val Thr Gly
            690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                        725                 730                 735

Leu Pro Glu Ala Gln Val Pro Cys Met Cys Arg Ala His Val Glu Gly
                740                 745                 750

Pro Ser Cys Asp Arg Cys Lys Pro Gly Phe Trp Gly Leu Ser Pro Ser
                755                 760                 765

Asn Pro Glu Gly Cys Thr Arg Cys Ser Cys Asp Leu Arg Gly Thr Leu
                770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                        805                 810                 815

Gly Leu Asp Gln Ala Asp Tyr Phe Gly Cys Arg Ser Cys Arg Cys Asp
                820                 825                 830

Ile Gly Gly Ala Leu Gly Gln Ser Cys Glu Pro Arg Thr Gly Val Cys
            835                 840                 845

Arg Cys Arg Pro Asn Thr Gln Gly Pro Thr Cys Ser Glu Pro Ala Arg
850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                        885                 890                 895

Glu Phe Glu Asn Phe Ser Trp Arg Gly Tyr Ala Gln Met Ala Pro Val
                900                 905                 910

Gln Pro Arg Ile Val Ala Arg Leu Asn Leu Thr Ser Pro Asp Leu Phe
            915                 920                 925

Trp Leu Val Phe Arg Tyr Val Asn Arg Gly Ala Met Ser Val Ser Gly
            930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Pro Ser Thr Glu Pro Ala
                        965                 970                 975

Phe Ile Thr Val Pro Gln Arg Gly Phe Gly Glu Pro Phe Val Leu Asn
                980                 985                 990

Pro Gly Thr Trp Ala Leu Arg Val  Glu Ala Glu Gly Val  Leu Leu Asp
            995                 1000                1005

Tyr Val  Val Leu Leu Pro Ser  Ala Tyr Glu Ala  Ala Leu Leu
    1010                1015                1020

Gln Leu  Arg Val Thr Glu Ala  Cys Thr Tyr Arg Pro  Ser Ala Gln
    1025                1030                1035

Gln Ser  Gly Asp Asn Cys Leu  Leu Tyr Thr His Leu  Pro Leu Asp
    1040                1045                1050

Gly Phe  Pro Ser Ala Ala Gly  Leu Glu Ala Leu Cys  Arg Gln Asp
    1055                1060                1065
```

```
Asn Ser Leu Pro Arg Pro Cys Pro Thr Glu Gln Leu Ser Pro Ser
1070                1075                1080

His Pro Pro Leu Ile Thr Cys Thr Gly Ser Asp Val Asp Val Gln
    1085                1090                1095

Leu Gln Val Ala Val Pro Gln Pro Gly Arg Tyr Ala Leu Val Val
1100                1105                1110

Glu Tyr Ala Asn Glu Asp Ala Arg Gln Glu Val Gly Val Ala Val
    1115                1120                1125

His Thr Pro Gln Arg Ala Pro Gln Gln Gly Leu Leu Ser Leu His
    1130                1135                1140

Pro Cys Leu Tyr Ser Thr Leu Cys Arg Gly Thr Ala Arg Asp Thr
    1145                1150                1155

Gln Asp His Leu Ala Val Phe His Leu Asp Ser Glu Ala Ser Val
    1160                1165                1170

Arg Leu Thr Ala Glu Gln Ala Arg Phe Phe Leu His Gly Val Thr
    1175                1180                1185

Leu Val Pro Ile Glu Glu Phe Ser Pro Glu Phe Val Glu Pro Arg
    1190                1195                1200

Val Ser Cys Ile Ser Ser His Gly Ala Phe Gly Pro Asn Ser Ala
    1205                1210                1215

Ala Cys Leu Pro Ser Arg Phe Pro Lys Pro Pro Gln Pro Ile Ile
    1220                1225                1230

Leu Arg Asp Cys Gln Val Ile Pro Leu Pro Pro Gly Leu Pro Leu
    1235                1240                1245

Thr His Ala Gln Asp Leu Thr Pro Ala Met Ser Pro Ala Gly Pro
    1250                1255                1260

Arg Pro Arg Pro Pro Thr Ala Val Asp Pro Asp Ala Glu Pro Thr
    1265                1270                1275

Leu Leu Arg Glu Pro Gln Ala Thr Val Val Phe Thr Thr His Val
    1280                1285                1290

Pro Thr Leu Gly Arg Tyr Ala Phe Leu Leu His Gly Tyr Gln Pro
    1295                1300                1305

Ala His Pro Thr Phe Pro Val Glu Val Leu Ile Asn Ala Gly Arg
    1310                1315                1320

Val Trp Gln Gly His Ala Asn Ala Ser Phe Cys Pro His Gly Tyr
    1325                1330                1335

Gly Cys Arg Thr Leu Val Val Cys Glu Gly Gln Ala Leu Leu Asp
    1340                1345                1350

Val Thr His Ser Glu Leu Thr Val Thr Val Arg Val Pro Lys Gly
    1355                1360                1365

Arg Trp Leu Trp Leu Asp Tyr Val Leu Val Val Pro Glu Asn Val
    1370                1375                1380

Tyr Ser Phe Gly Tyr Leu Arg Glu Glu Pro Leu Asp Lys Ser Tyr
    1385                1390                1395

Asp Phe Ile Ser His Cys Ala Ala Gln Gly Tyr His Ile Ser Pro
    1400                1405                1410

Ser Ser Ser Ser Leu Phe Cys Arg Asn Ala Ala Ala Ser Leu Ser
    1415                1420                1425

Leu Phe Tyr Asn Asn Gly Ala Arg Pro Cys Gly Cys His Glu Val
    1430                1435                1440

Gly Ala Thr Gly Pro Thr Cys Glu Pro Phe Gly Gly Gln Cys Pro
    1445                1450                1455
```

```
Cys His Ala His Val Ile Gly Arg Asp Cys Ser Arg Cys Ala Thr
    1460             1465             1470

Gly Tyr Trp Gly Phe Pro Asn Cys Arg Pro Cys Asp Cys Gly Ala
    1475             1480             1485

Arg Leu Cys Asp Glu Leu Thr Gly Gln Cys Ile Cys Pro Pro Arg
    1490             1495             1500

Thr Ile Pro Pro Asp Cys Leu Leu Cys Gln Pro Gln Thr Phe Gly
    1505             1510             1515

Cys His Pro Leu Val Gly Cys Glu Glu Cys Asn Cys Ser Gly Pro
    1520             1525             1530

Gly Ile Gln Glu Leu Thr Asp Pro Thr Cys Asp Thr Asp Ser Gly
    1535             1540             1545

Gln Cys Lys Cys Arg Pro Asn Val Thr Gly Arg Cys Asp Thr
    1550             1555             1560

Cys Ser Pro Gly Phe His Gly Tyr Pro Arg Cys Arg Pro Cys Asp
    1565             1570             1575

Cys His Glu Ala Gly Thr Ala Pro Gly Val Cys Asp Pro Leu Thr
    1580             1585             1590

Gly Gln Cys Tyr Cys Lys Glu Asn Val Gln Gly Pro Lys Cys Asp
    1595             1600             1605

Gln Cys Ser Leu Gly Thr Phe Ser Leu Asp Ala Ala Asn Pro Lys
    1610             1615             1620

Gly Cys Thr Arg Cys Phe Cys Phe Gly Ala Thr Glu Arg Cys Arg
    1625             1630             1635

Ser Ser Ser Tyr Thr Arg Gln Glu Phe Val Asp Met Glu Gly Trp
    1640             1645             1650

Val Leu Leu Ser Thr Asp Arg Gln Val Val Pro His Glu Arg Gln
    1655             1660             1665

Pro Gly Thr Glu Met Leu Arg Ala Asp Leu Arg His Val Pro Glu
    1670             1675             1680

Ala Val Pro Glu Ala Phe Pro Glu Leu Tyr Trp Gln Ala Pro Pro
    1685             1690             1695

Ser Tyr Leu Gly Asp Arg Val Ser Ser Tyr Gly Gly Thr Leu Arg
    1700             1705             1710

Tyr Glu Leu His Ser Glu Thr Gln Arg Gly Asp Val Phe Val Pro
    1715             1720             1725

Met Glu Ser Arg Pro Asp Val Val Leu Gln Gly Asn Gln Met Ser
    1730             1735             1740

Ile Thr Phe Leu Glu Pro Ala Tyr Pro Thr Pro Gly His Val His
    1745             1750             1755

Arg Gly Gln Leu Gln Leu Val Glu Gly Asn Phe Arg His Thr Glu
    1760             1765             1770

Thr Arg Asn Thr Val Ser Arg Glu Glu Leu Met Met Val Leu Ala
    1775             1780             1785

Ser Leu Glu Gln Leu Gln Ile Arg Ala Leu Phe Ser Gln Ile Ser
    1790             1795             1800

Ser Ala Val Phe Leu Arg Arg Val Ala Leu Glu Val Ala Ser Pro
    1805             1810             1815

Ala Gly Gln Gly Ala Leu Ala Ser Asn Val Glu Leu Cys Leu Cys
    1820             1825             1830

Pro Ala Ser Tyr Arg Gly Asp Ser Cys Gln Glu Cys Ala Pro Gly
    1835             1840             1845

Phe Tyr Arg Asp Val Lys Gly Leu Phe Leu Gly Arg Cys Val Pro
```

-continued

```
            1850                1855                1860
Cys Gln Cys His Gly His Ser Asp Arg Cys Leu Pro Gly Ser Gly
    1865            1870                1875

Val Cys Val Asp Cys Gln His Asn Thr Glu Gly Ala His Cys Glu
    1880                1885                1890

Arg Cys Gln Ala Gly Phe Val Ser Ser Arg Asp Asp Pro Ser Ala
    1895                1900                1905

Pro Cys Val Ser Cys Pro Cys Pro Leu Ser Val Pro Ser Asn Asn
    1910                1915                1920

Phe Ala Glu Gly Cys Val Leu Arg Gly Gly Arg Thr Gln Cys Leu
    1925                1930                1935

Cys Lys Pro Gly Tyr Ala Gly Ala Ser Cys Glu Arg Cys Ala Pro
    1940                1945                1950

Gly Phe Phe Gly Asn Pro Leu Val Leu Gly Ser Ser Cys Gln Pro
    1955                1960                1965

Cys Asp Cys Ser Gly Asn Gly Asp Pro Asn Leu Leu Phe Ser Asp
    1970                1975                1980

Cys Asp Pro Leu Thr Gly Ala Cys Arg Gly Cys Leu Arg His Thr
    1985                1990                1995

Thr Gly Pro Arg Cys Glu Ile Cys Ala Pro Gly Phe Tyr Gly Asn
    2000                2005                2010

Ala Leu Leu Pro Gly Asn Cys Thr Arg Cys Asp Cys Thr Pro Cys
    2015                2020                2025

Gly Thr Glu Ala Cys Asp Pro His Ser Gly His Cys Leu Cys Lys
    2030                2035                2040

Ala Gly Val Thr Gly Arg Arg Cys Asp Arg Cys Gln Glu Gly His
    2045                2050                2055

Phe Gly Phe Asp Gly Cys Gly Cys Arg Pro Cys Ala Cys Gly
    2060                2065                2070

Pro Ala Ala Glu Gly Ser Glu Cys His Pro Gln Ser Gly Gln Cys
    2075                2080                2085

His Cys Arg Pro Gly Thr Met Gly Pro Gln Cys Arg Glu Cys Ala
    2090                2095                2100

Pro Gly Tyr Trp Gly Leu Pro Glu Gln Gly Cys Arg Arg Cys Gln
    2105                2110                2115

Cys Pro Gly Gly Arg Cys Asp Pro His Thr Gly Arg Cys Asn Cys
    2120                2125                2130

Pro Pro Gly Leu Ser Gly Glu Arg Cys Asp Thr Cys Ser Gln Gln
    2135                2140                2145

His Gln Val Pro Val Pro Gly Gly Pro Val Gly His Ser Ile His
    2150                2155                2160

Cys Glu Val Cys Asp His Cys Val Val Leu Leu Leu Asp Asp Leu
    2165                2170                2175

Glu Arg Ala Gly Ala Leu Leu Pro Ala Ile His Glu Gln Leu Arg
    2180                2185                2190

Gly Ile Asn Ala Ser Ser Met Ala Trp Ala Arg Leu His Arg Leu
    2195                2200                2205

Asn Ala Ser Ile Ala Asp Leu Gln Ser Gln Leu Arg Ser Pro Leu
    2210                2215                2220

Gly Pro Arg His Glu Thr Ala Gln Gln Leu Glu Val Leu Glu Gln
    2225                2230                2235

Gln Ser Thr Ser Leu Gly Gln Asp Ala Arg Arg Leu Gly Gly Gln
    2240                2245                2250
```

```
Ala Val Gly Thr Arg Asp Gln Ala Ser Gln Leu Leu Ala Gly Thr
2255                2260                2265

Glu Ala Thr Leu Gly His Ala Lys Thr Leu Leu Ala Ala Ile Arg
2270                2275                2280

Ala Val Asp Arg Thr Leu Ser Glu Leu Met Ser Gln Thr Gly His
2285                2290                2295

Leu Gly Leu Ala Asn Ala Ser Ala Pro Ser Gly Glu Gln Leu Leu
2300                2305                2310

Arg Thr Leu Ala Glu Val Glu Arg Leu Leu Trp Glu Met Arg Ala
2315                2320                2325

Arg Asp Leu Gly Ala Pro Gln Ala Ala Ala Glu Ala Glu Leu Ala
2330                2335                2340

Ala Ala Gln Arg Leu Leu Ala Arg Val Gln Glu Gln Leu Ser Ser
2345                2350                2355

Leu Trp Glu Glu Asn Gln Ala Leu Ala Thr Gln Thr Arg Asp Arg
2360                2365                2370

Leu Ala Gln His Glu Ala Gly Leu Met Asp Leu Arg Glu Ala Leu
2375                2380                2385

Asn Arg Ala Val Asp Ala Thr Arg Glu Ala Gln Glu Leu Asn Ser
2390                2395                2400

Arg Asn Gln Glu Arg Leu Glu Glu Ala Leu Gln Arg Lys Gln Glu
2405                2410                2415

Leu Ser Arg Asp Asn Ala Thr Leu Gln Ala Thr Leu His Ala Ala
2420                2425                2430

Arg Asp Thr Leu Ala Ser Val Phe Arg Leu Leu His Ser Leu Asp
2435                2440                2445

Gln Ala Lys Glu Glu Leu Glu Arg Leu Ala Ala Ser Leu Asp Gly
2450                2455                2460

Ala Arg Thr Pro Leu Leu Gln Arg Met Gln Thr Phe Ser Pro Ala
2465                2470                2475

Gly Ser Lys Leu Arg Leu Val Glu Ala Ala Glu Ala His Ala Gln
2480                2485                2490

Gln Leu Gly Gln Leu Ala Leu Asn Leu Ser Ser Ile Ile Leu Asp
2495                2500                2505

Val Asn Gln Asp Arg Leu Thr Gln Arg Ala Ile Glu Ala Ser Asn
2510                2515                2520

Ala Tyr Ser Arg Ile Leu Gln Ala Val Gln Ala Ala Glu Asp Ala
2525                2530                2535

Ala Gly Gln Ala Leu Gln Gln Ala Asp His Thr Trp Ala Thr Val
2540                2545                2550

Val Arg Gln Gly Leu Val Asp Arg Ala Gln Gln Leu Leu Ala Asn
2555                2560                2565

Ser Thr Ala Leu Glu Glu Ala Met Leu Gln Glu Gln Gln Arg Leu
2570                2575                2580

Gly Leu Val Trp Ala Ala Leu Gln Gly Ala Arg Thr Gln Leu Arg
2585                2590                2595

Asp Val Arg Ala Lys Lys Asp Gln Leu Glu Ala His Ile Gln Ala
2600                2605                2610

Ala Gln Ala Met Leu Ala Met Asp Thr Asp Glu Thr Ser Lys Lys
2615                2620                2625

Ile Ala His Ala Lys Ala Val Ala Ala Glu Ala Gln Asp Thr Ala
2630                2635                2640
```

-continued

```
Thr Arg Val Gln Ser Gln Leu Gln Ala Met Gln Glu Asn Val Glu
    2645                2650                2655
Arg Trp Gln Gly Gln Tyr Glu Gly Leu Arg Gly Gln Asp Leu Gly
    2660                2665                2670
Gln Ala Val Leu Asp Ala Gly His Ser Val Ser Thr Leu Glu Lys
    2675                2680                2685
Thr Leu Pro Gln Leu Leu Ala Lys Leu Ser Ile Leu Glu Asn Arg
    2690                2695                2700
Gly Val His Asn Ala Ser Leu Ala Leu Ser Ala Ser Ile Gly Arg
    2705                2710                2715
Val Arg Glu Leu Ile Ala Gln Ala Arg Gly Ala Ala Ser Lys Val
    2720                2725                2730
Lys Val Pro Met Lys Phe Asn Gly Arg Ser Gly Val Gln Leu Arg
    2735                2740                2745
Thr Pro Arg Asp Leu Ala Asp Leu Ala Ala Tyr Thr Ala Leu Lys
    2750                2755                2760
Phe Tyr Leu Gln Gly Pro Glu Pro Glu Pro Gly Gln Gly Thr Glu
    2765                2770                2775
Asp Arg Phe Val Met Tyr Met Gly Ser Arg Gln Ala Thr Gly Asp
    2780                2785                2790
Tyr Met Gly Val Ser Leu Arg Asp Lys Lys Val His Trp Val Tyr
    2795                2800                2805
Gln Leu Gly Glu Ala Gly Pro Ala Val Leu Ser Ile Asp Glu Asp
    2810                2815                2820
Ile Gly Glu Gln Phe Ala Ala Val Ser Leu Asp Arg Thr Leu Gln
    2825                2830                2835
Phe Gly His Met Ser Val Thr Val Glu Arg Gln Met Ile Gln Glu
    2840                2845                2850
Thr Lys Gly Asp Thr Val Ala Pro Gly Ala Glu Gly Leu Leu Asn
    2855                2860                2865
Leu Arg Pro Asp Asp Phe Val Phe Tyr Val Gly Gly Tyr Pro Ser
    2870                2875                2880
Thr Phe Thr Pro Pro Pro Leu Leu Arg Phe Pro Gly Tyr Arg Gly
    2885                2890                2895
Cys Ile Glu Met Asp Thr Leu Asn Glu Glu Val Val Ser Leu Tyr
    2900                2905                2910
Asn Phe Glu Arg Thr Phe Gln Leu Asp Thr Ala Val Asp Arg Pro
    2915                2920                2925
Cys Ala Arg Ser Lys Ser Thr Gly Asp Pro Trp Leu Thr Asp Gly
    2930                2935                2940
Ser Tyr Leu Asp Gly Thr Gly Phe Ala Arg Ile Ser Phe Asp Ser
    2945                2950                2955
Gln Ile Ser Thr Thr Lys Arg Phe Glu Gln Glu Leu Arg Leu Val
    2960                2965                2970
Ser Tyr Ser Gly Val Leu Phe Phe Leu Lys Gln Gln Ser Gln Phe
    2975                2980                2985
Leu Cys Leu Ala Val Gln Glu Gly Ser Leu Val Leu Leu Tyr Asp
    2990                2995                3000
Phe Gly Ala Gly Leu Lys Lys Ala Val Pro Leu Gln Pro Pro Pro
    3005                3010                3015
Pro Leu Thr Ser Ala Ser Lys Ala Ile Gln Val Phe Leu Leu Gly
    3020                3025                3030
Gly Ser Arg Lys Arg Val Leu Val Arg Val Glu Arg Ala Thr Val
```

-continued

```
             3035                3040                3045
Tyr  Ser  Val  Glu  Gln  Asp  Asn  Asp  Leu  Glu  Leu  Ala  Asp  Ala  Tyr
     3050                3055                3060
Tyr  Leu  Gly  Gly  Val  Pro  Pro  Asp  Gln  Leu  Pro  Pro  Ser  Leu  Arg
     3065                3070                3075
Arg  Leu  Phe  Pro  Thr  Gly  Gly  Ser  Val  Arg  Gly  Cys  Val  Lys  Gly
     3080                3085                3090
Ile  Lys  Ala  Leu  Gly  Lys  Tyr  Val  Asp  Leu  Lys  Arg  Leu  Asn  Thr
     3095                3100                3105
Thr  Gly  Val  Ser  Ala  Gly  Cys  Thr  Ala  Asp  Leu  Leu  Val  Gly  Arg
     3110                3115                3120
Ala  Met  Thr  Phe  His  Gly  His  Gly  Phe  Leu  Arg  Leu  Ala  Leu  Ser
     3125                3130                3135
Asn  Val  Ala  Pro  Leu  Thr  Gly  Asn  Val  Tyr  Ser  Gly  Phe  Gly  Phe
     3140                3145                3150
His  Ser  Ala  Gln  Asp  Ser  Ala  Leu  Leu  Tyr  Tyr  Arg  Ala  Ser  Pro
     3155                3160                3165
Asp  Gly  Leu  Cys  Gln  Val  Ser  Leu  Gln  Gln  Gly  Arg  Val  Ser  Leu
     3170                3175                3180
Gln  Leu  Leu  Arg  Thr  Glu  Val  Lys  Thr  Gln  Ala  Gly  Phe  Ala  Asp
     3185                3190                3195
Gly  Ala  Pro  His  Tyr  Val  Ala  Phe  Tyr  Ser  Asn  Ala  Thr  Gly  Val
     3200                3205                3210
Trp  Leu  Tyr  Val  Asp  Asp  Gln  Leu  Gln  Gln  Met  Lys  Pro  His  Arg
     3215                3220                3225
Gly  Pro  Pro  Pro  Glu  Leu  Gln  Pro  Gln  Pro  Glu  Gly  Pro  Pro  Arg
     3230                3235                3240
Leu  Leu  Leu  Gly  Gly  Leu  Pro  Glu  Ser  Gly  Thr  Ile  Tyr  Asn  Phe
     3245                3250                3255
Ser  Gly  Cys  Ile  Ser  Asn  Val  Phe  Val  Gln  Arg  Leu  Leu  Gly  Pro
     3260                3265                3270
Gln  Arg  Val  Phe  Asp  Leu  Gln  Gln  Asn  Leu  Gly  Ser  Val  Asn  Val
     3275                3280                3285
Ser  Thr  Gly  Cys  Ala  Pro  Ala  Leu  Gln  Ala  Gln  Thr  Pro  Gly  Leu
     3290                3295                3300
Gly  Pro  Arg  Gly  Leu  Gln  Ala  Thr  Ala  Arg  Lys  Ala  Ser  Arg  Arg
     3305                3310                3315
Ser  Arg  Gln  Pro  Ala  Arg  His  Pro  Ala  Cys  Met  Leu  Pro  Pro  His
     3320                3325                3330
Leu  Arg  Thr  Thr  Arg  Asp  Ser  Tyr  Gln  Phe  Gly  Gly  Ser  Leu  Ser
     3335                3340                3345
Ser  His  Leu  Glu  Phe  Val  Gly  Ile  Leu  Ala  Arg  His  Arg  Asn  Trp
     3350                3355                3360
Pro  Ser  Leu  Ser  Met  His  Val  Leu  Pro  Arg  Ser  Ser  Arg  Gly  Leu
     3365                3370                3375
Leu  Leu  Phe  Thr  Ala  Arg  Leu  Arg  Pro  Gly  Ser  Pro  Ser  Leu  Ala
     3380                3385                3390
Leu  Phe  Leu  Ser  Asn  Gly  His  Phe  Val  Ala  Gln  Met  Glu  Gly  Leu
     3395                3400                3405
Gly  Thr  Arg  Leu  Arg  Ala  Gln  Ser  Arg  Gln  Arg  Ser  Arg  Pro  Gly
     3410                3415                3420
Arg  Trp  His  Lys  Val  Ser  Val  Arg  Trp  Glu  Lys  Asn  Arg  Ile  Leu
     3425                3430                3435
```

```
Leu Val Thr Asp Gly Ala Arg Ala Trp Ser Gln Glu Gly Pro His
    3440                3445                3450

Arg Gln His Gln Gly Ala Glu His Pro Gln Pro His Thr Leu Phe
    3455                3460                3465

Val Gly Gly Leu Pro Ala Ser Ser His Ser Ser Lys Leu Pro Val
    3470                3475                3480

Thr Val Gly Phe Ser Gly Cys Val Lys Arg Leu Arg Leu His Gly
    3485                3490                3495

Arg Pro Leu Gly Ala Pro Thr Arg Met Ala Gly Val Thr Pro Cys
    3500                3505                3510

Ile Leu Gly Pro Leu Glu Ala Gly Leu Phe Phe Pro Gly Ser Gly
    3515                3520                3525

Gly Val Ile Thr Leu Asp Leu Pro Gly Ala Thr Leu Pro Asp Val
    3530                3535                3540

Gly Leu Glu Leu Glu Val Arg Pro Leu Ala Val Thr Gly Leu Ile
    3545                3550                3555

Phe His Leu Gly Gln Ala Arg Thr Pro Pro Tyr Leu Gln Leu Gln
    3560                3565                3570

Val Thr Glu Lys Gln Val Leu Leu Arg Ala Asp Asp Gly Ala Gly
    3575                3580                3585

Glu Phe Ser Thr Ser Val Thr Arg Pro Ser Val Leu Cys Asp Gly
    3590                3595                3600

Gln Trp His Arg Leu Ala Val Met Lys Ser Gly Asn Val Leu Arg
    3605                3610                3615

Leu Glu Val Asp Ala Gln Ser Asn His Thr Val Gly Pro Leu Leu
    3620                3625                3630

Ala Ala Ala Ala Gly Ala Pro Ala Pro Leu Tyr Leu Gly Gly Leu
    3635                3640                3645

Pro Glu Pro Met Ala Val Gln Pro Trp Pro Ala Tyr Cys Gly
    3650                3655                3660

Cys Met Arg Arg Leu Ala Val Asn Arg Ser Pro Val Ala Met Thr
    3665                3670                3675

Arg Ser Val Glu Val His Gly Ala Val Gly Ala Ser Gly Cys Pro
    3680                3685                3690

Ala Ala
    3695

<210> SEQ ID NO 4
<211> LENGTH: 1786
<212> TYPE: PRT
<213> ORGANISM: Homo sapiens

<400> SEQUENCE: 4

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
                20                  25                  30

Gly Ser Cys Tyr Pro Ala Thr Gly Asp Leu Leu Ile Gly Arg Ala Gln
            35                  40                  45

Lys Leu Ser Val Thr Ser Thr Cys Gly Leu His Lys Pro Glu Pro Tyr
        50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
```

```
                    85                  90                  95
Glu Asn Val Val Thr Thr Phe Ala Pro Asn Arg Leu Lys Ile Trp Trp
                100                 105                 110

Gln Ser Glu Asn Gly Val Glu Asn Val Thr Ile Gln Leu Asp Leu Glu
            115                 120                 125

Ala Glu Phe His Phe Thr His Leu Ile Met Thr Phe Lys Thr Phe Arg
        130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
    210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
            260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
    290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
            340                 345                 350

Ala Thr Gly Asn Val Ser Gly Gly Val Cys Asp Asp Cys Gln His Asn
        355                 360                 365

Thr Met Gly Arg Asn Cys Glu Gln Cys Lys Pro Phe Tyr Tyr Gln His
    370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
            420                 425                 430

Glu Gly Glu His Cys Asp Val Cys Lys Glu Gly Phe Tyr Asp Leu Ser
        435                 440                 445

Ser Glu Asp Pro Phe Gly Cys Lys Ser Cys Ala Cys Asn Pro Leu Gly
    450                 455                 460

Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
            500                 505                 510
```

```
Asp Leu Gly Gly Ala Leu Asn Asn Ser Cys Phe Ala Glu Ser Gly Gln
            515                 520                 525

Cys Ser Cys Arg Pro His Met Ile Gly Arg Gln Cys Asn Glu Val Glu
        530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
        595                 600                 605

Glu Tyr Asp Ile Leu Ile Arg Tyr Glu Pro Gln Leu Pro Asp His Trp
        610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
                660                 665                 670

Glu Lys Gly Thr Asn Tyr Thr Val Arg Leu Glu Leu Pro Gln Tyr Thr
            675                 680                 685

Ser Ser Asp Ser Asp Val Glu Ser Pro Tyr Thr Leu Ile Asp Ser Leu
690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
            740                 745                 750

Asp Val Cys Arg Asn Ile Ile Phe Ser Ile Ser Ala Leu Leu His Gln
        755                 760                 765

Thr Gly Leu Ala Cys Glu Cys Asp Pro Gln Gly Ser Leu Ser Ser Val
    770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
            820                 825                 830

Cys Asn Pro Val Thr Gly Gln Cys His Cys Phe Gln Gly Val Tyr Ala
        835                 840                 845

Arg Gln Cys Asp Arg Cys Leu Pro Gly His Trp Gly Phe Pro Ser Cys
    850                 855                 860

Gln Pro Cys Gln Cys Asn Gly His Ala Asp Asp Cys Asp Pro Val Thr
865                 870                 875                 880

Gly Glu Cys Leu Asn Cys Gln Asp Tyr Thr Met Gly His Asn Cys Glu
                885                 890                 895

Arg Cys Leu Ala Gly Tyr Tyr Gly Asp Pro Ile Ile Gly Ser Gly Asp
            900                 905                 910

His Cys Arg Pro Cys Pro Cys Pro Asp Gly Pro Asp Ser Gly Arg Gln
        915                 920                 925
```

```
Phe Ala Arg Ser Cys Tyr Gln Asp Pro Val Thr Leu Gln Leu Ala Cys
    930             935             940
Val Cys Asp Pro Gly Tyr Ile Gly Ser Arg Cys Asp Asp Cys Ala Ser
945             950             955                 960
Gly Tyr Phe Gly Asn Pro Ser Glu Val Gly Gly Ser Cys Gln Pro Cys
                965             970             975
Gln Cys His Asn Asn Ile Asp Thr Thr Asp Pro Glu Ala Cys Asp Lys
            980             985             990
Glu Thr Gly Arg Cys Leu Lys Cys Leu Tyr His Thr Glu Gly Glu His
        995             1000            1005
Cys Gln Phe Cys Arg Phe Gly Tyr Tyr Gly Asp Ala Leu Gln Gln
    1010            1015            1020
Asp Cys Arg Lys Cys Val Cys Asn Tyr Leu Gly Thr Val Gln Glu
    1025            1030            1035
His Cys Asn Gly Ser Asp Cys Gln Cys Asp Lys Ala Thr Gly Gln
    1040            1045            1050
Cys Leu Cys Leu Pro Asn Val Ile Gly Gln Asn Cys Asp Arg Cys
    1055            1060            1065
Ala Pro Asn Thr Trp Gln Leu Ala Ser Gly Thr Gly Cys Asp Pro
    1070            1075            1080
Cys Asn Cys Asn Ala Ala His Ser Phe Gly Pro Ser Cys Asn Glu
    1085            1090            1095
Phe Thr Gly Gln Cys Gln Cys Met Pro Gly Phe Gly Gly Arg Thr
    1100            1105            1110
Cys Ser Glu Cys Gln Glu Leu Phe Trp Gly Asp Pro Asp Val Glu
    1115            1120            1125
Cys Arg Ala Cys Asp Cys Asp Pro Arg Gly Ile Glu Thr Pro Gln
    1130            1135            1140
Cys Asp Gln Ser Thr Gly Gln Cys Val Cys Val Glu Gly Val Glu
    1145            1150            1155
Gly Pro Arg Cys Asp Lys Cys Thr Arg Gly Tyr Ser Gly Val Phe
    1160            1165            1170
Pro Asp Cys Thr Pro Cys His Gln Cys Phe Ala Leu Trp Asp Val
    1175            1180            1185
Ile Ile Ala Glu Leu Thr Asn Arg Thr His Arg Phe Leu Glu Lys
    1190            1195            1200
Ala Lys Ala Leu Lys Ile Ser Gly Val Ile Gly Pro Tyr Arg Glu
    1205            1210            1215
Thr Val Asp Ser Val Glu Arg Lys Val Ser Glu Ile Lys Asp Ile
    1220            1225            1230
Leu Ala Gln Ser Pro Ala Ala Glu Pro Leu Lys Asn Ile Gly Asn
    1235            1240            1245
Leu Phe Glu Glu Ala Glu Lys Leu Ile Lys Asp Val Thr Glu Met
    1250            1255            1260
Met Ala Gln Val Glu Val Lys Leu Ser Asp Thr Thr Ser Gln Ser
    1265            1270            1275
Asn Ser Thr Ala Lys Glu Leu Asp Ser Leu Gln Thr Glu Ala Glu
    1280            1285            1290
Ser Leu Asp Asn Thr Val Lys Glu Leu Ala Glu Gln Leu Glu Phe
    1295            1300            1305
Ile Lys Asn Ser Asp Ile Arg Gly Ala Leu Asp Ser Ile Thr Lys
    1310            1315            1320
Tyr Phe Gln Met Ser Leu Glu Ala Glu Glu Arg Val Asn Ala Ser
```

-continued

```
            1325                1330                1335
Thr Thr Glu Pro Asn Ser Thr Val Glu Gln Ser Ala Leu Met Arg
        1340                1345                1350

Asp Arg Val Glu Asp Val Met Met Glu Arg Glu Ser Gln Phe Lys
        1355                1360                1365

Glu Lys Gln Glu Glu Gln Ala Arg Leu Leu Asp Glu Leu Ala Gly
        1370                1375                1380

Lys Leu Gln Ser Leu Asp Leu Ser Ala Ala Ala Glu Met Thr Cys
        1385                1390                1395

Gly Thr Pro Pro Gly Ala Ser Cys Ser Glu Thr Glu Cys Gly Gly
        1400                1405                1410

Pro Asn Cys Arg Thr Asp Glu Gly Glu Arg Lys Cys Gly Gly Pro
        1415                1420                1425

Gly Cys Gly Gly Leu Val Thr Val Ala His Asn Ala Trp Gln Lys
        1430                1435                1440

Ala Met Asp Leu Asp Gln Asp Val Leu Ser Ala Leu Ala Glu Val
        1445                1450                1455

Glu Gln Leu Ser Lys Met Val Ser Glu Ala Lys Leu Arg Ala Asp
        1460                1465                1470

Glu Ala Lys Gln Ser Ala Glu Asp Ile Leu Leu Lys Thr Asn Ala
        1475                1480                1485

Thr Lys Glu Lys Met Asp Lys Ser Asn Glu Glu Leu Arg Asn Leu
        1490                1495                1500

Ile Lys Gln Ile Arg Asn Phe Leu Thr Gln Asp Ser Ala Asp Leu
        1505                1510                1515

Asp Ser Ile Glu Ala Val Ala Asn Glu Val Leu Lys Met Glu Met
        1520                1525                1530

Pro Ser Thr Pro Gln Gln Leu Gln Asn Leu Thr Glu Asp Ile Arg
        1535                1540                1545

Glu Arg Val Glu Ser Leu Ser Gln Val Glu Val Ile Leu Gln His
        1550                1555                1560

Ser Ala Ala Asp Ile Ala Arg Ala Glu Met Leu Leu Glu Glu Ala
        1565                1570                1575

Lys Arg Ala Ser Lys Ser Ala Thr Asp Val Lys Val Thr Ala Asp
        1580                1585                1590

Met Val Lys Glu Ala Leu Glu Glu Ala Glu Lys Ala Gln Val Ala
        1595                1600                1605

Ala Glu Lys Ala Ile Lys Gln Ala Asp Glu Asp Ile Gln Gly Thr
        1610                1615                1620

Gln Asn Leu Leu Thr Ser Ile Glu Ser Glu Thr Ala Ala Ser Glu
        1625                1630                1635

Glu Thr Leu Phe Asn Ala Ser Gln Arg Ile Ser Glu Leu Glu Arg
        1640                1645                1650

Asn Val Glu Glu Leu Lys Arg Lys Ala Ala Gln Asn Ser Gly Glu
        1655                1660                1665

Ala Glu Tyr Ile Glu Lys Val Val Tyr Thr Val Lys Gln Ser Ala
        1670                1675                1680

Glu Asp Val Lys Lys Thr Leu Asp Gly Glu Leu Asp Glu Lys Tyr
        1685                1690                1695

Lys Lys Val Glu Asn Leu Ile Ala Lys Lys Thr Glu Glu Ser Ala
        1700                1705                1710

Asp Ala Arg Arg Lys Ala Glu Met Leu Gln Asn Glu Ala Lys Thr
        1715                1720                1725
```

```
Leu Leu Ala Gln Ala Asn Ser Lys Leu Gln Leu Leu Lys Asp Leu
        1730                1735                1740

Glu Arg Lys Tyr Glu Asp Asn Gln Arg Tyr Leu Glu Asp Lys Ala
    1745                1750                1755

Gln Glu Leu Ala Arg Leu Gly Glu Val Arg Ser Leu Leu Lys
1760                1765                1770

Asp Ile Ser Gln Lys Val Ala Val Tyr Ser Thr Cys Leu
    1775                1780                1785

<210> SEQ ID NO 5
<211> LENGTH: 1811
<212> TYPE: PRT
<213> ORGANISM: Homo sapiens

<400> SEQUENCE: 5

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
                20                  25                  30

Gln Ala Pro Ala Pro Asp Val Pro Gly Cys Ser Arg Gly Ser Cys Tyr
            35                  40                  45

Pro Ala Thr Gly Asp Leu Leu Val Gly Arg Ala Asp Arg Leu Thr Ala
        50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
        195                 200                 205

Ile Glu Pro Ser Thr Glu Gly Glu Val Ile Tyr Arg Val Leu Asp Pro
    210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
    290                 295                 300

Met Val His Gly Ala Cys Ile Cys Lys His Asn Thr Arg Gly Leu Asn
```

```
            305                 310                 315                 320
        Cys Glu Gln Cys Gln Asp Phe Tyr Arg Asp Leu Pro Trp Arg Pro Ala
                        325                 330                 335
        Glu Asp Gly His Ser His Ala Cys Arg Lys Cys Glu Cys His Gly His
                        340                 345                 350
        Thr His Ser Cys His Phe Asp Met Ala Val Tyr Leu Ala Ser Gly Asn
                        355                 360                 365
        Val Ser Gly Val Cys Asp Gly Cys Gln His Asn Thr Ala Gly Arg
            370                 375                 380
        His Cys Glu Leu Cys Arg Pro Phe Phe Tyr Arg Asp Pro Thr Lys Asp
        385                 390                 395                 400
        Leu Arg Asp Pro Ala Val Cys Arg Ser Cys Asp Cys Asp Pro Met Gly
                        405                 410                 415
        Ser Gln Asp Gly Gly Arg Cys Asp Ser His Asp Asp Pro Ala Leu Gly
                        420                 425                 430
        Leu Val Ser Gly Gln Cys Arg Cys Lys Glu His Val Val Gly Thr Arg
                        435                 440                 445
        Cys Gln Gln Cys Arg Asp Gly Phe Phe Gly Leu Ser Ile Ser Asp Arg
            450                 455                 460
        Leu Gly Cys Arg Arg Cys Gln Cys Asn Ala Arg Gly Thr Val Pro Gly
        465                 470                 475                 480
        Ser Thr Pro Cys Asp Pro Asn Ser Gly Ser Cys Tyr Cys Lys Arg Leu
                        485                 490                 495
        Val Thr Gly Arg Gly Cys Asp Arg Cys Leu Pro Gly His Trp Gly Leu
                        500                 505                 510
        Ser His Asp Leu Leu Gly Cys Arg Pro Cys Asp Cys Asp Val Gly Gly
                        515                 520                 525
        Ala Leu Asp Pro Gln Cys Asp Glu Gly Thr Gly Gln Cys His Cys Arg
                        530                 535                 540
        Gln His Met Val Gly Arg Arg Cys Glu Gln Val Gln Pro Gly Tyr Phe
        545                 550                 555                 560
        Arg Pro Phe Leu Asp His Leu Ile Trp Glu Ala Glu Asp Thr Arg Gly
                        565                 570                 575
        Gln Val Leu Asp Val Val Glu Arg Leu Val Thr Pro Gly Glu Thr Pro
                        580                 585                 590
        Ser Trp Thr Gly Ser Gly Phe Val Arg Leu Gln Glu Gly Gln Thr Leu
                        595                 600                 605
        Glu Phe Leu Val Ala Ser Val Pro Lys Ala Met Asp Tyr Asp Leu Leu
        610                 615                 620
        Leu Arg Leu Glu Pro Gln Val Pro Glu Gln Trp Ala Glu Leu Glu Leu
        625                 630                 635                 640
        Ile Val Gln Arg Pro Gly Pro Val Pro Ala His Ser Leu Cys Gly His
                        645                 650                 655
        Leu Val Pro Lys Asp Asp Arg Ile Gln Gly Thr Leu Gln Pro His Ala
                        660                 665                 670
        Arg Tyr Leu Ile Phe Pro Asn Pro Val Cys Leu Glu Pro Gly Ile Ser
                        675                 680                 685
        Tyr Lys Leu His Leu Lys Leu Val Arg Thr Gly Gly Ser Ala Gln Pro
                        690                 695                 700
        Glu Thr Pro Tyr Ser Gly Pro Gly Leu Leu Ile Asp Ser Leu Val Leu
        705                 710                 715                 720
        Leu Pro Arg Val Leu Val Leu Glu Met Phe Ser Gly Gly Asp Ala Ala
                        725                 730                 735
```

```
Ala Leu Glu Arg Gln Ala Thr Phe Glu Arg Tyr Gln Cys His Glu Glu
            740                 745                 750

Gly Leu Val Pro Ser Lys Thr Pro Ser Glu Ala Cys Ala Pro Leu
            755                 760                 765

Leu Ile Ser Leu Ser Thr Leu Ile Tyr Asn Gly Ala Leu Pro Cys Gln
        770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Cys Asp Leu Cys
                805                 810                 815

Ala Pro Gly Tyr Tyr Gly Phe Gly Pro Thr Gly Cys Gln Ala Cys Gln
            820                 825                 830

Cys Ser His Glu Gly Ala Leu Ser Ser Leu Cys Glu Lys Thr Ser Gly
            835                 840                 845

Gln Cys Leu Cys Arg Thr Gly Ala Phe Gly Leu Arg Cys Asp Arg Cys
850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
            900                 905                 910

His Gly Asp Pro Arg Leu Pro Tyr Gly Gly Gln Cys Arg Pro Cys Pro
            915                 920                 925

Cys Pro Glu Gly Pro Gly Ser Gln Arg His Phe Ala Thr Ser Cys His
    930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
            965                 970                 975

Ser Arg Pro Gly Gly Arg Cys Gln Leu Cys Glu Cys Ser Gly Asn Ile
            980                 985                 990

Asp Pro Met Asp Pro Asp Ala Cys Asp Pro His Thr Gly Gln Cys Leu
            995                 1000                1005

Arg Cys Leu His His Thr Glu Gly Pro His Cys Ala His Cys Lys
    1010                1015                1020

Pro Gly Phe His Gly Gln Ala Ala Arg Gln Ser Cys His Arg Cys
    1025                1030                1035

Thr Cys Asn Leu Leu Gly Thr Asn Pro Gln Gln Cys Pro Ser Pro
    1040                1045                1050

Asp Gln Cys His Cys Asp Pro Ser Ser Gly Gln Cys Pro Cys Leu
    1055                1060                1065

Pro Asn Val Gln Gly Pro Ser Cys Asp Arg Cys Ala Pro Asn Phe
    1070                1075                1080

Trp Asn Leu Thr Ser Gly His Gly Cys Gln Pro Cys Ala Cys His
    1085                1090                1095

Pro Ser Arg Ala Arg Gly Pro Thr Cys Asn Glu Phe Thr Gly Gln
    1100                1105                1110

Cys His Cys Arg Ala Gly Phe Gly Gly Arg Thr Cys Ser Glu Cys
    1115                1120                1125

Gln Glu Leu His Trp Gly Asp Pro Gly Leu Gln Cys His Ala Cys
    1130                1135                1140
```

```
Asp Cys Asp Ser Arg Gly Ile Asp Thr Pro Gln Cys His Arg Phe
    1145                1150                1155

Thr Gly His Cys Ser Cys Arg Pro Gly Val Ser Gly Val Arg Cys
    1160                1165                1170

Asp Gln Cys Ala Arg Gly Phe Ser Gly Ile Phe Pro Ala Cys His
    1175                1180                1185

Pro Cys His Ala Cys Phe Gly Asp Trp Asp Arg Val Val Gln Asp
    1190                1195                1200

Leu Ala Ala Arg Thr Gln Arg Leu Glu Gln Arg Ala Gln Glu Leu
    1205                1210                1215

Gln Gln Thr Gly Val Leu Gly Ala Phe Glu Ser Ser Phe Trp His
    1220                1225                1230

Met Gln Glu Lys Leu Gly Ile Val Gln Gly Ile Val Gly Ala Arg
    1235                1240                1245

Asn Thr Ser Ala Ala Ser Thr Ala Gln Leu Val Glu Ala Thr Glu
    1250                1255                1260

Glu Leu Arg Arg Glu Ile Gly Glu Ala Thr Glu His Leu Thr Gln
    1265                1270                1275

Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Asp Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
    1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470

Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530

Glu Met Val Ala Thr Arg Val Leu Glu Leu Ser Ile Pro Ala Ser
```

```
            1535                1540                1545

Ala Glu Gln Ile Gln His Leu Ala Gly Ala Ile Ala Glu Arg Val
        1550                1555                1560

Arg Ser Leu Ala Asp Val Asp Ala Ile Leu Ala Arg Thr Val Gly
        1565                1570                1575

Asp Val Arg Arg Ala Glu Gln Leu Leu Gln Asp Ala Arg Arg Ala
        1580                1585                1590

Arg Ser Trp Ala Glu Asp Glu Lys Gln Lys Ala Glu Thr Val Gln
        1595                1600                1605

Ala Ala Leu Glu Glu Ala Gln Arg Ala Gln Gly Ile Ala Gln Gly
        1610                1615                1620

Ala Ile Arg Gly Ala Val Ala Asp Thr Arg Asp Thr Glu Gln Thr
        1625                1630                1635

Leu Tyr Gln Val Gln Glu Arg Met Ala Gly Ala Glu Arg Ala Leu
        1640                1645                1650

Ser Ser Ala Gly Glu Arg Ala Arg Gln Leu Asp Ala Leu Leu Glu
        1655                1660                1665

Ala Leu Lys Leu Lys Arg Ala Gly Asn Ser Leu Ala Ala Ser Thr
        1670                1675                1680

Ala Glu Glu Thr Ala Gly Ser Ala Gln Gly Arg Ala Gln Glu Ala
        1685                1690                1695

Glu Gln Leu Leu Arg Gly Pro Leu Gly Asp Gln Tyr Gln Thr Val
        1700                1705                1710

Lys Ala Leu Ala Glu Arg Lys Ala Gln Gly Val Leu Ala Ala Gln
        1715                1720                1725

Ala Arg Ala Glu Gln Leu Arg Asp Glu Ala Arg Asp Leu Leu Gln
        1730                1735                1740

Ala Ala Gln Asp Lys Leu Gln Arg Leu Gln Glu Leu Glu Gly Thr
        1745                1750                1755

Tyr Glu Glu Asn Glu Arg Ala Leu Glu Ser Lys Ala Ala Gln Leu
        1760                1765                1770

Asp Gly Leu Glu Ala Arg Met Arg Ser Val Leu Gln Ala Ile Asn
        1775                1780                1785

Leu Gln Val Gln Ile Tyr Asn Thr Cys Gln Lys Ser Ser Trp Pro
        1790                1795                1800

Gly Arg Ala Pro Asn Lys Pro Val
        1805                1810

<210> SEQ ID NO 6
<211> LENGTH: 1609
<212> TYPE: PRT
<213> ORGANISM: Homo sapiens

<400> SEQUENCE: 6

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
                20                  25                  30

Ala Gln Ala Ala Met Asp Glu Cys Thr Asp Glu Gly Gly Arg Pro Gln
            35                  40                  45

Arg Cys Met Pro Glu Phe Val Asn Ala Ala Phe Asn Val Thr Val Val
        50                  55                  60

Ala Thr Asn Thr Cys Gly Thr Pro Pro Glu Glu Tyr Cys Val Gln Thr
65                  70                  75                  80
```

```
Gly Val Thr Gly Val Thr Lys Ser Cys His Leu Cys Asp Ala Gly Gln
                85                  90                  95
Pro His Leu Gln His Gly Ala Ala Phe Leu Thr Asp Tyr Asn Asn Gln
            100                 105                 110
Ala Asp Thr Thr Trp Trp Gln Ser Gln Thr Met Leu Ala Gly Val Gln
        115                 120                 125
Tyr Pro Ser Ser Ile Asn Leu Thr Leu His Leu Gly Lys Ala Phe Asp
    130                 135                 140
Ile Thr Tyr Val Arg Leu Lys Phe His Thr Ser Arg Pro Glu Ser Phe
145                 150                 155                 160
Ala Ile Tyr Lys Arg Thr Arg Glu Asp Gly Pro Trp Ile Pro Tyr Gln
                165                 170                 175
Tyr Tyr Ser Gly Ser Cys Glu Asn Thr Tyr Ser Lys Ala Asn Arg Gly
            180                 185                 190
Phe Ile Arg Thr Gly Gly Asp Glu Gln Gln Ala Leu Cys Thr Asp Glu
        195                 200                 205
Phe Ser Asp Ile Ser Pro Leu Thr Gly Gly Asn Val Ala Phe Ser Thr
    210                 215                 220
Leu Glu Gly Arg Pro Ser Ala Tyr Asn Phe Asp Asn Ser Pro Val Leu
225                 230                 235                 240
Gln Glu Trp Val Thr Ala Thr Asp Ile Arg Val Thr Leu Asn Arg Leu
                245                 250                 255
Asn Thr Phe Gly Asp Glu Val Phe Asn Asp Pro Lys Val Leu Lys Ser
            260                 265                 270
Tyr Tyr Tyr Ala Ile Ser Asp Phe Ala Val Gly Gly Arg Cys Lys Cys
        275                 280                 285
Asn Gly His Ala Ser Glu Cys Met Lys Asn Glu Phe Asp Lys Leu Val
    290                 295                 300
Cys Asn Cys Lys His Asn Thr Tyr Gly Val Asp Cys Glu Lys Cys Leu
305                 310                 315                 320
Pro Phe Phe Asn Asp Arg Pro Trp Arg Arg Ala Thr Ala Glu Ser Ala
                325                 330                 335
Ser Glu Cys Leu Pro Cys Asp Cys Asn Gly Arg Ser Gln Glu Cys Tyr
            340                 345                 350
Phe Asp Pro Glu Leu Tyr Arg Ser Thr Gly His Gly Gly His Cys Thr
        355                 360                 365
Asn Cys Gln Asp Asn Thr Asp Gly Ala His Cys Glu Arg Cys Arg Glu
    370                 375                 380
Asn Phe Phe Arg Leu Gly Asn Asn Glu Ala Cys Ser Ser Cys His Cys
385                 390                 395                 400
Ser Pro Val Gly Ser Leu Ser Thr Gln Cys Asp Ser Tyr Gly Arg Cys
                405                 410                 415
Ser Cys Lys Pro Gly Val Met Gly Asp Lys Cys Asp Arg Cys Gln Pro
            420                 425                 430
Gly Phe His Ser Leu Thr Glu Ala Gly Cys Arg Pro Cys Ser Cys Asp
        435                 440                 445
Pro Ser Gly Ser Ile Asp Glu Cys Asn Ile Glu Thr Gly Arg Cys Val
    450                 455                 460
Cys Lys Asp Asn Val Glu Gly Phe Asn Cys Glu Arg Cys Lys Pro Gly
465                 470                 475                 480
Phe Phe Asn Leu Glu Ser Ser Asn Pro Arg Gly Cys Thr Pro Cys Phe
                485                 490                 495
Cys Phe Gly His Ser Ser Val Cys Thr Asn Ala Val Gly Tyr Ser Val
```

```
            500                 505                 510
Tyr Ser Ile Ser Ser Thr Phe Gln Ile Asp Glu Asp Gly Trp Arg Ala
        515                 520                 525

Glu Gln Arg Asp Gly Ser Glu Ala Ser Leu Glu Trp Ser Ser Glu Arg
        530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                565                 570                 575

Leu Ser Phe Ser Phe Arg Val Asp Arg Arg Asp Thr Arg Leu Ser Ala
                580                 585                 590

Glu Asp Leu Val Leu Glu Gly Ala Gly Leu Arg Val Ser Val Pro Leu
        595                 600                 605

Ile Ala Gln Gly Asn Ser Tyr Pro Ser Glu Thr Thr Val Lys Tyr Val
        610                 615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
                645                 650                 655

Arg Gly Thr Tyr Ser Glu Arg Ser Ala Gly Tyr Leu Asp Asp Val Thr
                660                 665                 670

Leu Ala Ser Ala Arg Pro Gly Pro Gly Val Pro Ala Thr Trp Val Glu
        675                 680                 685

Ser Cys Thr Cys Pro Val Gly Tyr Gly Gly Gln Phe Cys Glu Met Cys
        690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
                725                 730                 735

Thr Gly Val Cys Asn Cys Arg Asp Asn Thr Ala Gly Pro His Cys Glu
                740                 745                 750

Lys Cys Ser Asp Gly Tyr Tyr Gly Asp Ser Thr Ala Gly Thr Ser Ser
        755                 760                 765

Asp Cys Gln Pro Cys Pro Cys Pro Gly Gly Ser Ser Cys Ala Val Val
        770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
                805                 810                 815

Gly Arg Asn Gly Pro Val Arg Leu Cys Arg Leu Cys Gln Cys Ser Asp
                820                 825                 830

Asn Ile Asp Pro Asn Ala Val Gly Asn Cys Asn Arg Leu Thr Gly Glu
        835                 840                 845

Cys Leu Lys Cys Ile Tyr Asn Thr Ala Gly Phe Tyr Cys Asp Arg Cys
        850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
                885                 890                 895

Ser Cys Asn Pro Val Thr Gly Gln Cys Glu Cys Leu Pro His Val Thr
                900                 905                 910

Gly Gln Asp Cys Gly Ala Cys Asp Pro Gly Phe Tyr Asn Leu Gln Ser
        915                 920                 925
```

-continued

Gly Gln Gly Cys Glu Arg Cys Asp Cys His Ala Leu Gly Ser Thr Asn
    930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
            965                 970                 975

Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
        995                 1000                1005

Gly Asn Arg Cys Asp Gln Cys Glu Glu Asn Tyr Phe Tyr Asn Arg
    1010                1015                1020

Ser Trp Pro Gly Cys Gln Glu Cys Pro Ala Cys Tyr Arg Leu Val
    1025                1030                1035

Lys Asp Lys Val Ala Asp His Arg Val Lys Leu Gln Glu Leu Glu
    1040                1045                1050

Ser Leu Ile Ala Asn Leu Gly Thr Gly Asp Glu Met Val Thr Asp
    1055                1060                1065

Gln Ala Phe Glu Asp Arg Leu Lys Glu Ala Glu Arg Glu Val Met
    1070                1075                1080

Asp Leu Leu Arg Glu Ala Gln Asp Val Lys Asp Val Asp Gln Asn
    1085                1090                1095

Leu Met Asp Arg Leu Gln Arg Val Asn Asn Thr Leu Ser Ser Gln
    1100                1105                1110

Ile Ser Arg Leu Gln Asn Ile Arg Asn Thr Ile Glu Glu Thr Gly
    1115                1120                1125

Asn Leu Ala Glu Gln Ala Arg Ala His Val Glu Asn Thr Glu Arg
    1130                1135                1140

Leu Ile Glu Ile Ala Ser Arg Glu Leu Glu Lys Ala Lys Val Ala
    1145                1150                1155

Ala Ala Asn Val Ser Val Thr Gln Pro Glu Ser Thr Gly Asp Pro
    1160                1165                1170

Asn Asn Met Thr Leu Leu Ala Glu Glu Ala Arg Lys Leu Ala Glu
    1175                1180                1185

Arg His Lys Gln Glu Ala Asp Asp Ile Val Arg Val Ala Lys Thr
    1190                1195                1200

Ala Asn Asp Thr Ser Thr Glu Ala Tyr Asn Leu Leu Leu Arg Thr
    1205                1210                1215

Leu Ala Gly Glu Asn Gln Thr Ala Phe Glu Ile Glu Glu Leu Asn
    1220                1225                1230

Arg Lys Tyr Glu Gln Ala Lys Asn Ile Ser Gln Asp Leu Glu Lys
    1235                1240                1245

Gln Ala Ala Arg Val His Glu Glu Ala Lys Arg Ala Gly Asp Lys
    1250                1255                1260

Ala Val Glu Ile Tyr Ala Ser Val Ala Gln Leu Ser Pro Leu Asp
    1265                1270                1275

Ser Glu Thr Leu Glu Asn Glu Ala Asn Asn Ile Lys Met Glu Ala
    1280                1285                1290

Glu Asn Leu Glu Gln Leu Ile Asp Gln Lys Leu Lys Asp Tyr Glu
    1295                1300                1305

Asp Leu Arg Glu Asp Met Arg Gly Lys Glu Leu Glu Val Lys Asn
    1310                1315                1320

```
Leu Leu Glu Lys Gly Lys Thr Glu Gln Gln Thr Ala Asp Gln Leu
    1325            1330                1335
Leu Ala Arg Ala Asp Ala Ala Lys Ala Leu Ala Glu Glu Ala Ala
    1340            1345                1350
Lys Lys Gly Arg Asp Thr Leu Gln Glu Ala Asn Asp Ile Leu Asn
    1355            1360                1365
Asn Leu Lys Asp Phe Asp Arg Arg Val Asn Asp Asn Lys Thr Ala
    1370            1375                1380
Ala Glu Glu Ala Leu Arg Lys Ile Pro Ala Ile Asn Gln Thr Ile
    1385            1390                1395
Thr Glu Ala Asn Glu Lys Thr Arg Glu Ala Gln Gln Ala Leu Gly
    1400            1405                1410
Ser Ala Ala Ala Asp Ala Thr Glu Ala Lys Asn Lys Ala His Glu
    1415            1420                1425
Ala Glu Arg Ile Ala Ser Ala Val Gln Lys Asn Ala Thr Ser Thr
    1430            1435                1440
Lys Ala Glu Ala Glu Arg Thr Phe Ala Glu Val Thr Asp Leu Asp
    1445            1450                1455
Asn Glu Val Asn Asn Met Leu Lys Gln Leu Gln Glu Ala Glu Lys
    1460            1465                1470
Glu Leu Lys Arg Lys Gln Asp Asp Ala Asp Gln Asp Met Met Met
    1475            1480                1485
Ala Gly Met Ala Ser Gln Ala Ala Gln Glu Ala Glu Ile Asn Ala
    1490            1495                1500
Arg Lys Ala Lys Asn Ser Val Thr Ser Leu Leu Ser Ile Ile Asn
    1505            1510                1515
Asp Leu Leu Glu Gln Leu Gly Gln Leu Asp Thr Val Asp Leu Asn
    1520            1525                1530
Lys Leu Asn Glu Ile Glu Gly Thr Leu Asn Lys Ala Lys Asp Glu
    1535            1540                1545
Met Lys Val Ser Asp Leu Asp Arg Lys Val Ser Asp Leu Glu Asn
    1550            1555                1560
Glu Ala Lys Lys Gln Glu Ala Ala Ile Met Asp Tyr Asn Arg Asp
    1565            1570                1575
Ile Glu Glu Ile Met Lys Asp Ile Arg Asn Leu Glu Asp Ile Arg
    1580            1585                1590
Lys Thr Leu Pro Ser Gly Cys Phe Asn Thr Pro Ser Ile Glu Lys
    1595            1600                1605
Pro
```

DERIVATION AND SELF-RENEWAL OF ISl1+ CELLS AND USES THEREOF

CROSS REFERENCE TO RELATED APPLICATIONS

This application is a Divisional patent application of U.S. patent application Ser. No. 14/414,685, with an international filing date of Jul. 11, 2013; which is the U.S. National Phase application of PCT/SE2013/000112, filed Jul. 11, 2013, which claims priority to U.S. Provisional Application Ser. No. 61/670,640 filed Jul. 12, 2012, the contents of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737452000110SeqList.txt, date recorded: Mar. 11, 2019, size: 130 KB).

TECHNICAL FIELD

The present invention pertains inter alia to methods for deriving multi potent Isl1+ cells (i.e. methods for inducing a cell to enter a multipotent Isl1+lineage), methods for differentiating Isl1+ cells to cardiac cells, cells obtainable by such methods, kits and compositions for carrying out the methods in accordance with the invention, and also medical applications of said cells.

BACKGROUND

The turnover of cardiomyocytes is low in the adult heart but can increase during ischemia through upregulation of Islet-1 positive (Isl1+) or C-Kit positive (C-Kit+) multipotent cardiac progenitor cells (Genead et al., PlosOne 7, e36804 (2012)). The upregulation of endogenous progenitor cells is not sufficient to replace the damaged musculature after substantial ischemic damage, resulting in heart failure. An attractive approach to prevent the development of heart failure would be to provide progenitor cells capable of repairing tissue damage in the heart. These progenitor cells should be capable of giving rise to cardiomyocytes, smooth muscle cells, nerve cells and endothelium. Isl1+ cells have this capacity and form ⅔ of the developing heart including the sino-atrial node (SA), part of the atrial-ventricular node (AV), right atrium, right ventricle, proximal aorta, trunk of the pulmonary arteries and proximal parts of the coronary arteries (Lam et al., Pediatr. Cardiol. 30, 690 (2009)).

However, one considerable limitation in using these progenitor cells for regenerative medicine pertains to the difficulty of expanding well-characterized clonal progenitor cell populations, from either adult human tissue or from fetal/embryonic stem cell tissues. In an earlier study, Laugwitz and coworkers showed that it was possible to expand postnatal Isl1+cells from transgenic mice if they were co-cultured with cardiac mesenchymal feeder cells (Laugwitz et al., Nature 433, 647 (2005)). Therefore there is great need in the art for methods that efficiently enable the formation of cardiovascular progenitors and maintaining and expanding these cardiovascular progenitors in a multipotent state to enable the generation of a diverse set of heart lineages. A desired method would enable the production of, and subsequent unlimited expansion of progenitors capable of entering different cardiac lineages. Such a method is highly desirable as it will circumvent many of the issues relating to tissue rejection commonly associated with transplantation therapies, and overall provide alternative regenerative medicine strategies and improve treatment outcomes for patients suffering from a variety of cardiac and cardiovascular disorders.

SUMMARY OF THE INVENTION

It is hence an object of the present invention to overcome the above-identified problems and satisfy the existing needs within the art, i. e. to provide for facile and efficient derivation of multipotent Isl1$^+$ cells using clearly defined and highly controllable methods. Furthermore, the present invention enables not only efficient derivation of multipotent Isl1$^+$ cells but also substantially indefinite self-renewal and proliferation (i.e. clonal expansion) of said multipotent Isl1$^+$ cells, as well as cellular differentiation, e.g. into cardiac tissue. The cells obtainable using the methods in accordance with the present invention are highly suitable for various clinical applications and exhibit strong homing ability to tissues and sites of interest, for instance cardiac tissue after differentiation into cardiomyocytes. Specifically, Isl1$^+$ cells that have been differentiated into cardiac tissue, using the derivation and differentiation methods according to the present invention, home strongly to infarcted (ischemic) regions of the heart, where they become elongated and arrange in parallel with the surrounding cardiomyocytes.

Thus, the present invention pertains to, in a first aspect, methods for deriving multipotent Isl1$^+$ cells (i.e. methods for inducing a cell to enter a multipotent Isl1$^+$ lineage). Such methods may comprise the step of culturing a mesenchymal cell (also known as a mesenchymal stem cell (MSC)), e.g. a cell from a mesenchymal cell fraction, in the presence of at least one laminin comprising an α5 chain (the α5 chain is represented by SEQ ID No 3), and in a medium comprising at least one agent which activates the Wnt canonical pathway, and to continue culturing the cell culture for a sufficient period of time to derive the Isl1$^+$ cell (and/or a sufficient population of Isl1$^+$ cells).

In a further aspect, the instant invention relates to methods for self-renewal of multipotent Isl1$^+$ cells, said methods may comprise the steps of (i) culturing cells obtainable through the methods as per the above-described aspect in the presence of at least one laminin comprising an α5 chain, and in a medium comprising at least one agent which activates the Wnt canonical pathway; and, (ii) maintaining and/or expanding the cells obtainable from step (i) in cell culture. In a third aspect, the present invention pertains to a method for differentiating Isl1$^+$ cells into cardiac cells (e.g. cardiomyocytes, smooth muscle cells, and/or cardiac endothelial cells). In a further aspect, the present invention relates to cells obtainable by the methods in accordance with the invention, notably multipotent Isl1$^+$ cells and Isl1$^+$ cells differentiated into cardiac cells (normally expressing e.g. Troponin T and other markers for heart cells) (both the multipotent Isl1$^+$ cells and the Isl1$^+$ cells differentiated into cardiomyocytes may optionally be cryopreserved).

In additional aspects, the instant invention pertains to compositions and kits (e.g. kits of parts) for carrying out the methods of the present invention. The compositions according to the invention may comprise at least one laminin comprising an α5 chain and at least one agent which activates the Wnt canonical pathway, and the kit (i.e. a kit of parts), similarly, may comprise at least one laminin comprising an α5 chain and a cell culture medium comprising at least one agent which activates the Wnt canonical pathway. In a further aspect, the present invention relates to kits and/or compositions for differentiating cells (notably Isl1+ cells) into cardiomyocytes. Such kits may comprise at least one laminin selected from the group comprising laminin-111, laminin-211, laminin-221, and any combination thereof. The components of the kit (e.g. the laminin and the Wnt-activating agent) may advantageously be provided in separate containers (for instance vials, ampoules, tubes, or the like), in order to enable combining the components when carrying out the methods as per the present invention. The laminins of the kits and/or compositions may be provided either in a suitable medium, lyophilized, or coated on dishes/plastic suitable for cell culture.

In other aspects, the present invention pertains to the cells as per the present invention for for use in medicine. More specifically, the cells may be used in the treatment and/or prophylaxis of heart insufficiency, heart failure, myocardial infarction, and/or congenital heart disease due to cardiac defects affecting parts derived from the second heart field (for instance right atrium, right ventricle, outflow tracts (aorta, pulmonary arteries) and ventricular septum). Further aspects as per the instant invention relates to pharmaceutical compositions comprising cells as per the invention, together with at least one pharmaceutically acceptable excipient, for use in medicine, for instance for use in the treatment and/or prophylaxis of heart insufficiency, heart failure, myocardial infarction, and/or congenital heart disease due to cardiac defects affecting parts derived from the second heart field (for instance right atrium, right ventricle, outflow tracts (aorta, pulmonary arteries) and ventricular septum).

A further aspect in accordance with the present invention pertains to methods of treatment for improving, alleviating or preventing heart insufficiency, heart failure, myocardial infarction, and/or congenital heart disease due to cardiac defects affecting parts derived from the second heart field (for instance right atrium, right ventricle, outflow tracts (aorta, pulmonary arteries) and ventricular septum) in a subject in need thereof, the method comprising administering to the subject a therapeutically effective amount of the cells according to the instant invention.

In yet another aspect, the present invention pertains to the use of a combination of at least one laminin comprising an α5 chain and at least one agent which activates the Wnt canonical pathway, for deriving a multipotent Isl1+ cell. In a further aspect, the present invention also relates to the use of laminin-111, laminin-211, laminin-221, and/or any combination thereof for differentiating cells (preferably Isl1+ cells in accordance with the present invention) into cardiac cells, for instance cardiomyocytes.

The present invention thus provides methods for deriving multipotent Isl1+ cell, for self-renewing such cells, and for differentiating such cells into cardiac cells, with considerably improved efficiency, less variability, under defined clinically acceptable conditions, and with enhanced control compared to the methods of the current art. Furthermore, the compositions and kits as per the present invention facilitate carrying out the methods as per the present invention, enabling facile culturing and handling, for both clinical and experimental purposes.

BRIEF DESCRIPTION OF THE DRAWINGS

(FIG. 1A) In the initial adherent stem cell fraction, there was only a small number of Isl1+ cells (<1%) (in the heart tissue these were mixed with cardiomyocytes expressing cardiac α-actinin). During the first week of culture in a Wnt-medium on laminin 511, laminin 521, or a combination of the two, the mesenchymal stem cells switched into cells expressing Isl1. Along with the Isl1+ cells there were more differentiated cells expressing cardiac α-actinin. During subsequent passages, the relative proportion of cells expressing cardiac α-actinin was reduced and after two weeks in culture (5 passages), 73±18% of the cells expressed Isl1 and there was no differentiated cells left. (FIG. 1B) Within two weeks of culture, the initial fraction had expanded 16 times. (FIG. 1C) Western blot analysis confirmed the activation of the Wnt/β-catenin pathway in the cultured Isl1+ cells, demonstrating increased levels of both phosphorylated Lrp6 on Serine 1490 and active (dephosphorylated) β-catenin (ABC) compared to the initial adherent cell fraction. In panel a, bars represent 50 μm.

(FIG. 2A) Schematic representation of the experimental procedure used to generate and expand multipotent Isl1+ cells from a mesenchymal stem cell fraction. (FIG. 2B) Before initiation of the Wnt and laminin protocol, less than 5% of the mesenchymal stem cell fraction expressed Isl1 (when using fetal/embryonic heart tissue these cells were mixed with cells expressing cardiac α-actinin (α-act)). (FIG. 2C) During the first week in culture on the at least one α5-containing laminin and in the Wnt-medium, the mesenchymal stem cell fraction switched into cells expressing Isl1. (FIG. 2D) After two weeks of culture, 92±2% of the cells were Isl1 positive and more than 40% of the cells were still proliferating expressing Ki67. (FIG. 2E) The cultured Isl1+ cells could be differentiated into cells expressing cardiac α-actinin, von Willebrand factor (vWF) and smooth muscle actin (SMA). (FIG. 2F) After three weeks of culture, the Isl1+ cell population had expanded more than 1000-fold. In order to verify the protocol, the initial mesenchymal stem cell fraction was cultured under different conditions: Wnt-medium+at least one α5-containing laminin, Wnt-medium+plastic, Medium without Wnt3a+at least one α5-containing laminin and Medium without Wnt3a+plastic. (FIG. 2G) The qRT-PCR-analysis demonstrates that the combination of Wnt-medium and at least one laminin comprising an α5 chain (e.g. either laminin 511 (a composition comprising SEQ ID No. 3, SEQ ID No. 4, and SEQ ID No. 6) or laminin 521 (a composition comprising SEQ ID No. 3, SEQ ID No. 5, and SEQ ID No. 6) or a combination of the two) is necessary for derivation and expansion of undifferentiated Isl1+ cells. In panel B to E, nuclear staining with DAPI is shown in magenta. Cells costaining for Isl1 and magenta are shown in white. Bars represent 50 μm. In panel F, error bars represent mean±SD. In figure: p<0.01; p<0.001.

(FIG. 5A) Total RNA was isolated from Isl1-positive (Islet1+ve, red cells) and –negative (Islet-1–ve) regions from a human fetal heart (9.5 weeks) and through laser capture microdissection. In figure: OFT: outflow tract; LA: left atrium; LV: left ventricle: RA: right atrium; RV: right ventricle. Nuclei are stained blue by DAPI. Bar represent 50 µm. (FIG. 5B) Heat map: The cultured human Isl1+ cells (obtained from human fetal heart) had a higher expression of Isl1 than the Isl1-positive region of the human embryonic heart, and the expression of differentiation markers was much lower. The expression of pluripotency markers of the cultured Isl1+ cells increased during the culturing process (from 2 to 3 weeks). In figure, average linkage and log 2 transformation of signals are presented. The heat map color scale ranges from red (high expression) via yellow to blue (low expression). (FIG. 5C) In flow cytometry analysis of human fetal heart, human cord blood MSCs, and human bone marrow MSCs, the CD34+ and CD45+ cell populations were excluded (and this may be preferably under certain circumstances). All human Isl1+ cells co-express KDR, 59.5% SSEA-1 and 4.3% c-kit. All SSEA-1+ cells co-express KDR, and they constitute 2.7% of the c-kit+ cell population.

(FIG. 6A) Hematoxylin and eosin staining demonstrating the site of injection of labelled Isl1+ cells into the left ventricular wall. 24 hours after injection, X-gal staining identified the labelled Isl1$^+$ cells (blue cells) both at the site of injection (insert in FIG. 6A) and in the outflow tract region close to the PA and Ao (insert in FIG. 6B). After two weeks, few Isl1+ cells could be detected at the site of injection (FIG. 6C). These cells had changed their appearance and were elongated and organized in parallel to the surrounding cardiomyocytes. (FIG. 6D, FIG. 6E) When labelled Isl1+ cells were injected into the peri-ischemic region of the left ventricle, the majority of the cells stayed in the infarction area (insert in FIG. 6D) and few cells were found in the outflow tract region 24 hours post injection (insert in FIG. 6E). (FIG. 6F) After two weeks, labelled Isl1+ cells were still found in the infarct area and again the implanted cells were elongated and interspersed between the surrounding cardiomyocytes (insert in FIG. 6F). In figures, bars represent 1000 µm and in insert 100 µm. Abbreviations; Ao: aorta; PA: pulmonary artery; RA: right atrium; LV: left ventricle.

(FIG. 7A) Labelled Isl1+ cells were injected into the left ventricular wall of a normal rat heart, where the In Vitro Imaging System (IVIS system) detected a strong signal a few hours after injection. (FIG. 7B) After 24 hours, the strongest signal was detected in a region corresponding to the outflow tract, where it stayed during the detection period of one week (FIG. 7C). Labeled Isl1+ cells were in the next step injected into the left ventricular wall of a normal heart. Within 24 hours, the strongest signal was detected in the outflow tract region (FIG. 7D). After induction of myocardial infarction, the strongest signal was again detected in the ischemic region where it increased from 24 hours (FIG. 7E) to one-week post infarction (FIG. 7F). (FIG. 7G) Injection of labelled Isl1+ cells into a tail vein, 8 hours after induction of myocardial infarction. The Isl1+ cells seemed to home into the infarction region where the signal was strongest. Signaling can also be seen in the lungs, which is probably indicative of some of the cells being maintained in the capillary network of the lungs.

DETAILED DESCRIPTION OF THE INVENTION

Figure 1A:
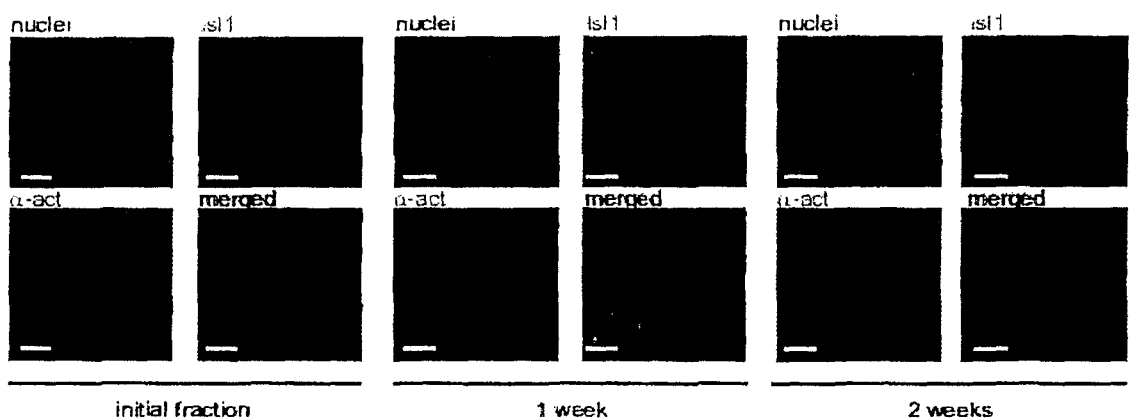
FIGS. 1A-C Derivation of Isl1+ cells from embryonic rat cardiac mesenchymal stem cells or from rat bone marrow.
Figure 1B:
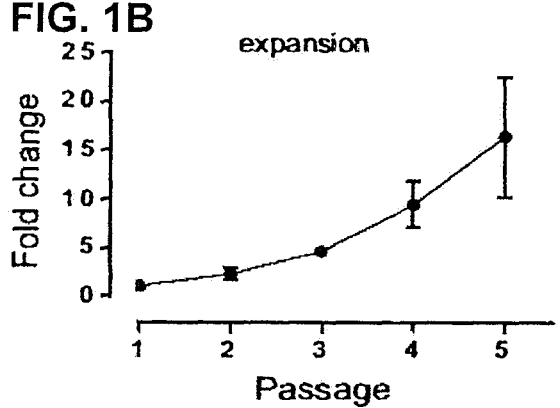
Figure 1C:
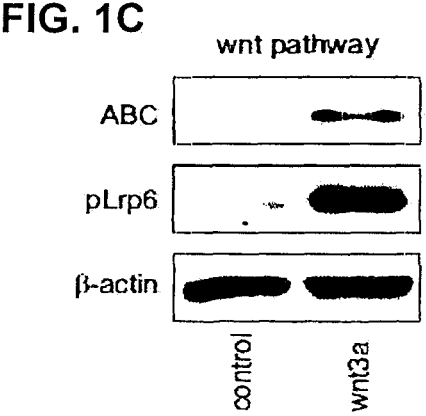
Figure 2A:
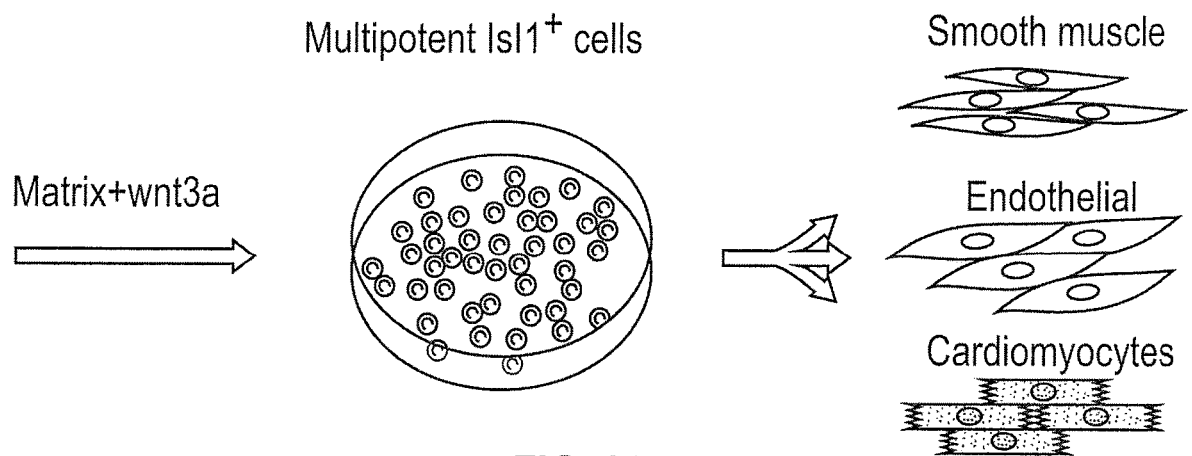
FIGS. 2A-G Derivation of Isl1+ cells from bone marrow, cord blood, and fetal/embryonic heart mesenchymal stem cells (MSCs).
Figure 2B:
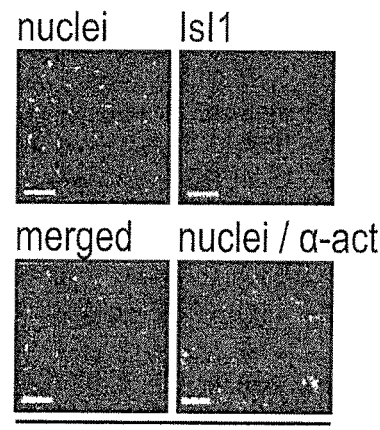
Figure 2C:
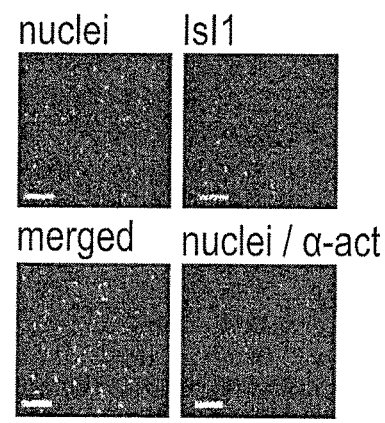
Figure 2D:
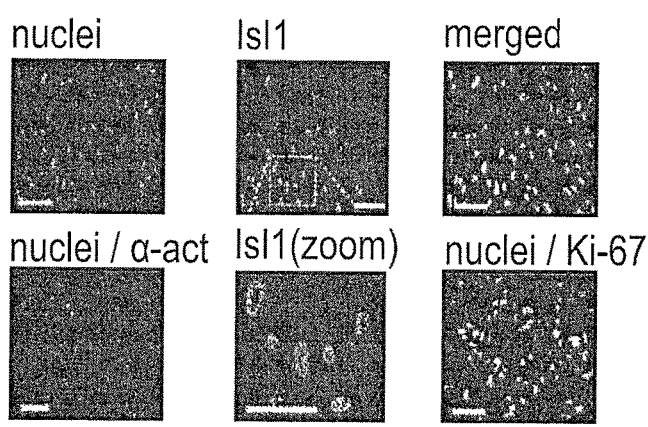
Figure 2E:
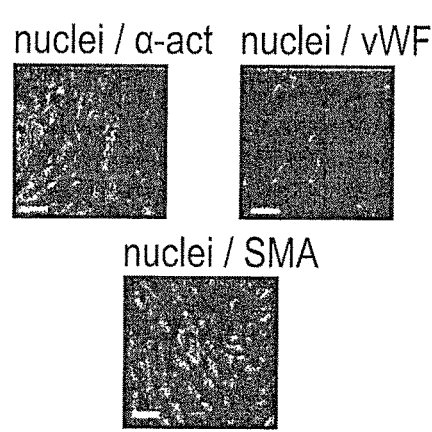
Figure 2F:
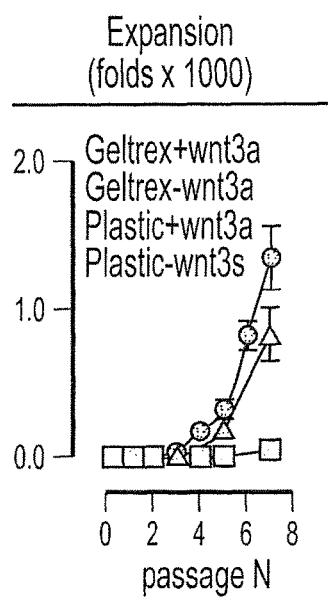
Figure 2G:
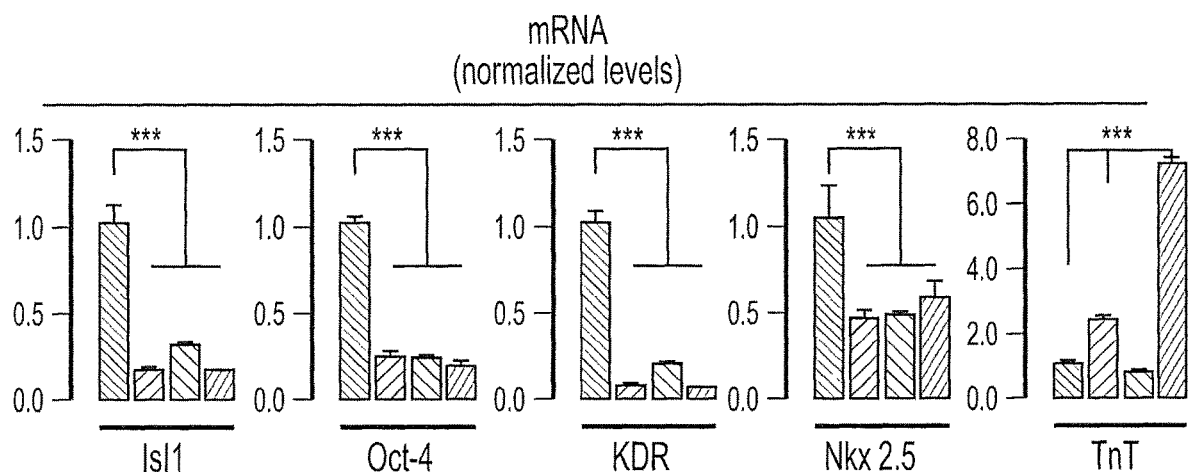

The present invention pertains inter alia to methods for deriving multipotent Isl1$^+$ cells (i.e. methods for inducing a cell to enter a multipotent Isl1$^+$ lineage), comprising the step of culturing a mesenchymal stem cell (MSC) (e.g. a cell from a mesenchymal cell fraction) in the presence of at least one laminin comprising an α5 chain, and in a medium comprising at least one agent which activates the Wnt canonical pathway. The Isl1$^+$ cell obtained using said method may subsequently be cultured in the presence of at least one laminin selected from the group comprising laminin 111, laminin 221, and laminin 211, or any combination thereof, in order to further differentiate the cell population. Also, the present invention pertains to methods for self-renewal and/or proliferation of Isl1$^+$ cells (optionally obtainable via the derivation methods as per the present invention but the self-renewal and/or maintenance procedure may also be applied to Isl1+ cells obtained via other methods or from other sources), comprising the steps of (i) culturing an Isl1+ cell in the presence of at least one laminin comprising an α5 chain, and in a medium comprising at least one agent which activates the Wnt canonical pathway; and, (ii) maintaining and/or expanding the cells obtainable from step (i), in cell culture. The Isl1$^+$ cell obtained in step (ii) of the self-renewal (proliferation) method may subsequently be cultured in the presence of at least one laminin selected from the group comprising laminin 111, laminin 211, laminin 221, and a combination thereof, in order to further differentiate the cell population (into cardiac cells, specifically cardiomyocytes).

The present invention additionally relates to cells obtainable by the methods in accordance with the present invention, compositions comprising at least one laminin comprising an α5 chain and at least one agent which activates the Wnt canonical pathway, as well as a kit (i.e. a kit of parts) comprising at least one laminin comprising an α5 chain and a cell culture medium containing at least one agent which activates the Wnt canonical pathway (e.g. in different vials), or, alternatively, a differentiation kit comprising at least one laminin selected from the group comprising laminin 111, laminin 211, laminin 221, and a combination thereof. Furthermore, the present invention also pertains to cells obtainable by the methods of the instant invention for use in medicine, for instance in cardiology-related indications, as well as pharmaceutical compositions comprising the cells and at least one pharmaceutically acceptable excipient, in order to enable efficient delivery of the cells to the target site/tissue. Finally, the present invention moreover relates to the use of a combination of at least one laminin comprising an α5 chain and at least one agent which activates the Wnt canonical pathway, for deriving a multipotent Isl1+ cell (i.e. for inducing a cell to enter a multipotent Isl1⁺ lineage). Similarly, the present invention moreover relates to the use of a combination of (i) laminin 111, laminin 211, laminin 221, or a combination thereof, and optionally (ii) at least one agent which activates the Wnt canonical pathway, for differentiating a multipotent Isl1+ cell into a cardiac cell. The agent which activates the Wnt canonical pathway may be included in the differentiation step although its presence is not absolutely necessary.

Where features, embodiments, or aspects of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in connection with one of the aspects and/or embodiments of the present invention also apply mutatis mutandis to all the other aspects and/or embodiments of the invention. For example, the at least one agent which activates the Wnt canonical pathway described in connection with the method for deriving the multipotent Isl1+ cells is to be understood to be relevant also for the kit of parts (interchangeably termed the kit). Furthermore, certain embodiments described in connection with certain aspects, for instance bromoindirubin-3'-oxime (BIO) as described in relation to the aspect pertaining to the method for deriving the multipotent Isl1+ cells, may naturally also be relevant in connection with other aspects and/or embodiment, in the case of BIO for instance in the aspects/embodiments pertaining to the compositions or the kit of parts, in accordance with the present invention.

In a first aspect, the present invention relates to a method for deriving multipotent Isl1⁺ cells (i.e. a method for inducing a cell to enter a multipotent Isl1⁺ lineage), comprising the steps of (i) culturing a mesenchymal cell (i.e. a cell from a mesenchymal cell fraction) in the presence of at least one laminin comprising an α5 chain, and in a medium comprising at least one agent which activates the Wnt canonical pathway (and continuing to culture the cell for a sufficient period of time to derive the Isl1⁺ cell and/or to derive sufficient populations of Isl1 cells).

It shall be understood that within the context of the present invention the term "culturing [ . . . ] in the presence of" may be interpreted as encompassing contacting the cell/cells with e.g. at least one laminin comprising an α5 chain and/or at least one agent which activates the Wnt canonical pathway. The time of culturing in the presence of for instance the at least one agent which activates the Wnt canonical pathway may naturally be of importance for the present invention, as is outlined in greater detail below. Normally, the laminins used within the context of the present invention are coated on the cell/tissue culture equipment, e.g. a cell culture dish or stent that may be implanted into the human or animal body for a therapeutic purpose, for instance to derive Isl1⁺ cells and subsequently differentiate said cells to cardiomyocytes, using the method steps of the present invention.

In a further embodiment in accordance with the present invention, the mesenchymal (stem) cells (e.g. cells from a mesenchymal fraction) may be cardiac mesenchymal cells, embryonic stem cells, cord blood stem cells, and/or amniotic stem cells, or any combination of these sources of cells. Mesenchymal cells, also known as mesenchymal stem cells (MSCs) are multipotent stromal cells that can differentiate into a variety of cell types, including but not limited to osteoblasts, chondrocytes, and adipocytes. MSCs may be derived from the bone marrow, mesoderm, umbilical cord blood, Wharton's jelly, adult muscle, developing tooth buds, and/or amniotic fluid. Cells from the "mesenchymal fraction" shall within the context of the present invention be understood to relate to cells that may be derived from any of the above sources, e.g. bone marrow, mesoderm, umbilical cord blood, Wharton's jelly, adult muscle, developing tooth buds, and/or amniotic fluid. Bone marrow aspirate is a suitable source for cells of a mesenchymal cell fraction (i.e. mesenchymal cells). Bone marrow aspirate may be obtained through entering the crista iliaca with an aspiration needle, followed by extracting a certain volume of cell-containing aspirate, which may subsequently be sorted, cultured or frozen for future use. Alternatively, cord blood or amniotic cells may be extracted and isolated for the purposes of the present invention. Isolation of said cells may be carried out in connection with partus through conventional techniques.

The MSCs (i.e. the cells from a mesenchymal fraction) that are employed for treating a patient may be of allogeneic origin, i.e. it is normally not necessary to use autologous cells from the patient in need of treatment.

Figure 8:
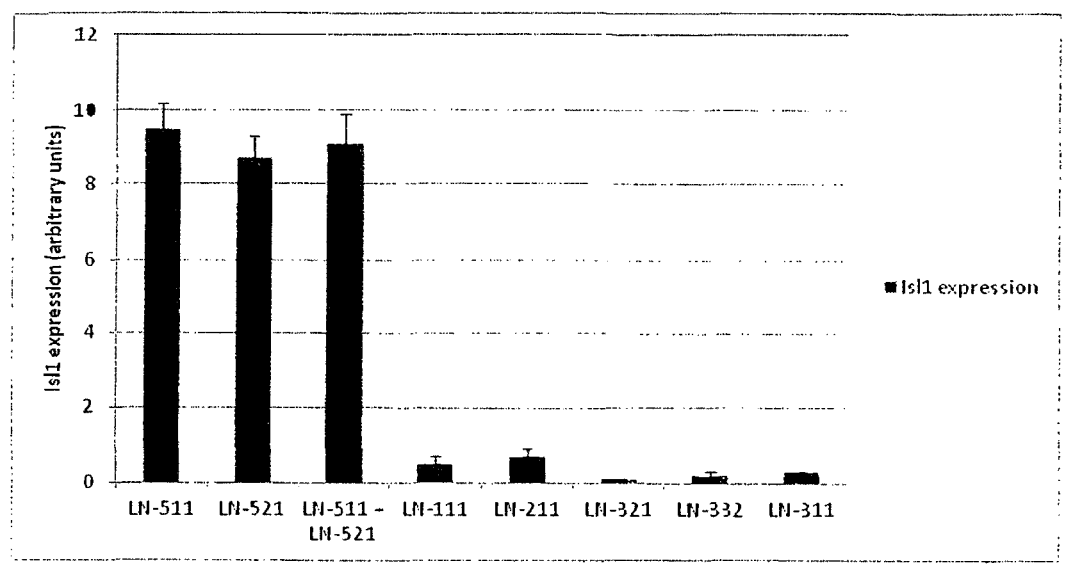
FIG. 8 Laminin comprising α5 chain crucial for derivation of Isl1+ cells. Laminin 511, laminin 521, and a combination of the two, induce mesenchymal stem cells (obtainable either from bone marrow of healthy human donors, from human cord blood, from the human amniotic sac, or from human fetal or embryonic heart tissue) to enter a multipotent Isl1 lineage, whereas other laminins are incapable of promoting derivation of Isl1$^+$ cells. Other laminins comprising an α5 chain (for instance laminins 522 and 523) are naturally also within the scope of the present invention.

The inventors have unexpectedly realized that using at least one laminin comprising an α5 chain is highly advantageous and results in surprisingly enhanced derivation of the Isl1⁺ cells (FIG. 8). When using the culturing methods of the present invention Isl1 expression was, after two weeks in culture, stably detected in more than 90% of the mesenchymal cell population, and after 3 weeks of culturing the cell population had expanded more than 1000-fold. The at least one laminin comprising an α5 chain may be selected from the group comprising laminin 511, laminin 521, a combination of laminin 511 and laminin 521, any natural, recombinant, or synthetic protein, which has at least approximately 70% (preferably at least 80% and even more preferably at least 90%) sequence identity to the polypeptide sequence of laminin 511 or laminin 521, any natural, recombinant, or synthetic protein comprising the polypeptide sequence of the laminin α5 chain G-domain, any natural, recombinant, or synthetic protein comprising a polypeptide sequence, which has at least approximately 70% (preferably at least 80% and even more preferably at least 90%) sequence identity to the polypeptide sequence of the laminin α5 chain G-domain, and any cell culture growth substratum or cell culture medium additive comprising polypeptides from the polypeptide sequence of laminin 511 or laminin 521.

Further in accordance with the present invention, the at least one agent which activates the Wnt canonical pathway may be selected from the group comprising Wnt-1, Wnt-3a, Wnt-8, Wnt-8b, and any combination thereof. Additional agents activating the Wnt canonical pathway are naturally also within the scope of the present invention, irrespective of whether the activation of the Wnt canonical pathway is effected via direct activation of the pathway in question (for instance mediated by Wnt-3a) or via indirect stimulation of the Wnt canonical pathway by blockage of the non-canonical pathway (for instance via blocking glycogen synthase kinase 3 (GSK3) which causes an upregulation of beta-catenin) (i.e. using BIO). Also, various types of agents may be utilized within the scope of the instant invention, as is outlined in more detail below.

The inventors have realized that selecting an appropriate concentration interval of the at least one agent which activates the Wnt canonical pathway is important for the present invention, suitably a concentration of approximately 10-250 ng/ml, but preferably a concentration of approximately 50-150 ng/ml, or even more preferably approximately around 100 ng/ml. Naturally, the concentration interval depends on the activity and the potency of the Wnt-activating agent employed in the specific case. When utilizing BIO, either in combination with e.g. a Wnt-activating polypeptide (e.g. Wnt-3a) or alone, a suitable concentration range may be approximately 0.1-5 mM, preferably approximately 0.5-3 mM, or even more preferably approximately 2.5 mM. Furthermore, epidermal growth factor (EGF), at a concentration ranging from 1 ng/ml to 100 ng/ml (preferably around 10 ng/ml) may be included in the culture medium, in order to enhance cell expansion. Additionally, when DMEM/F12 medium is used for the cell culturing methods, the medium may be supplemented with B27.

A second step of the method in accordance with the present invention (i.e. step (ii)) may further comprise expanding the Isl1$^+$ cell population, in order to increase the cell numbers. Additionally, the second step may furthermore comprise self-renewal and/or proliferation of the Isl1$^+$ cells (i.e. maintaining the Isl1$^+$ cells in culture basically indefinitely, to enable further usage or experimentation).

Figure 9:
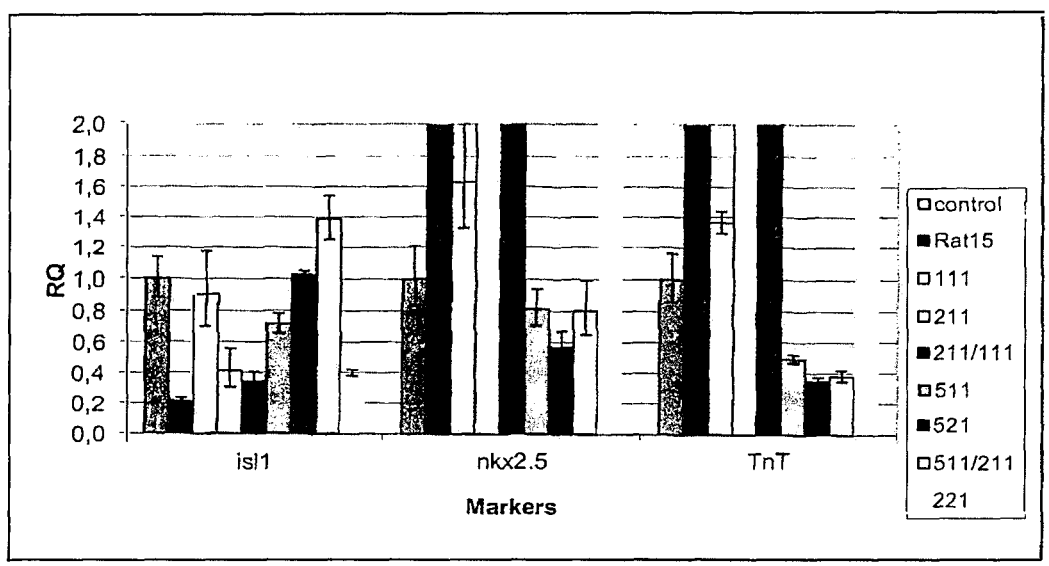
FIG. 9: Laminins 111 (a composition comprising SEQ ID No. 1, SEQ ID No. 2, and SEQ ID No. 6), 211 (a composition comprising SEQ ID No. 2, SEQ ID No. 2, and SEQ ID No. 6), 221 (a composition comprising SEQ ID No. 2, SEQ ID No. 5, and SEQ ID No. 6), and a combination of the two promotes cellular differentiation. Laminin 111, laminin 211, laminin 221, or any combination thereof, promote differentiation of Isl1+ cells into cardiac cells (e.g. cardiomyocytes, smooth muscle cells, and/or endothelial cells).

In order to further differentiate the cells obtainable by the methods of the present invention, a further differentiation step (iii) may be included, wherein Isl1$^+$ cells (either obtained via the derivation methods of the present invention or Isl1$^+$ cells obtainable from any other source) is cultured in the presence of at least one laminin selected from the group comprising laminin 111, laminin 211, laminin 221, and any combination of thereof, and any natural, recombinant, or synthetic protein comprising a polypeptide sequence, which has at least approximately 70% sequence identity to the polypeptide sequence(s) of either laminin 111, laminin 221, or laminin 211. When culturing the cells in the presence of the at least one laminin selected from the group comprising laminin 111, laminin 211, laminin 221, and a combination thereof, and any natural, recombinant, or synthetic protein comprising a polypeptide sequence, which has at least approximately 70% sequence identity to the polypeptide sequence(s) of either laminin 111, laminin 221 or laminin 211, the Wnt-activating agent may be excluded from the culture medium, in order to further enhance differentiation to the desired cell type, in this case cardiac (heart) cells (and possibly tissues) (FIG. 9). Laminin 111 and other al-containing laminins (such as laminin 121) may in some instances be utilized also to derive Isl1$^+$ cells from mesenchymal stem cells as per the present invention (in addition to their use for differentiating Isl1$^+$ cells into cardiac cells), although derivation using α5-containing laminins is generally significantly more efficient and reliable, al-containing laminins may be present in a 3-dimensional structure (such as a 3-dimensional matrix and/or gel, e.g. Geltrex™), in order to efficiently induce Isl1$^+$ expression (when using the same protocol as employed for the α5-containing laminins).

The present invention relates, at least partially, to methods for the production and expansion of Isl1$^+$ progenitors, for example cardiovascular progenitors, while maintaining their multipotency and capacity for multi-lineage differentiation. In a further aspect, the present invention pertains to a method for self-renewal of a multipotent Isl1$^+$ cell, comprising the steps of (i) culturing a cell, obtainable through the derivation methods as per the present invention, in the presence of at least one laminin comprising an α5 chain, and in a medium comprising at least one agent which activates the Wnt canonical pathway; and (ii) maintaining and/or expanding the cells obtainable from step (i) in cell culture, essentially indefinitely.

As abovementioned, in one aspect, the present invention provides a method to induce a cell to enter the Isl1$^+$ lineage. More specifically, the present invention is based on the realization that activation of Wnt signalling in the presence of at least one laminin comprising an α5 chain triggers the entry of cells into islet 1+ lineage and can be used to pre-specify cells to become Isl1$^+$ progenitors. Thus, the present invention pertains to methods to induce cells, for example uncommitted progenitors, into Isl1$^+$ progenitors, for example Isl1$^+$ cardiovascular progenitors. Furthermore, the instant invention provides methods for expanding Isl1$^+$ progenitors by triggering their renewal.

The cells in accordance with the present invention may be stem cells, including, but not limited to. embryonic stem cells, embryoid body (EB) cells, adult stem cells and fetal or postnatal stem cells, optionally obtained from from tissue, for instance embryonic, fetal, postnatal or adult tissue. The tissue may for instance be cardiac tissue. More specifically, the cells in accordance with the present invention may be cells from a mesenchymal fraction (i.e. mesenchymal cells, also known as mesenchymal stem cells), for instance derived from bone marrow, mesoderm, umbilical cord blood, Wharton's jelly, adult muscle, developing tooth buds, and/or amniotic fluid.

The tissue may comprise, but is not limited to, fibroblasts, cardiac fibroblasts, circulating endothelial progenitors, pancreas, liver, adipose tissue, bone marrow, kidney, bladder, palate, umbilical cord, amniotic fluid, dermal tissue, skin, muscle, spleen, placenta, bone, neural tissue or epithelial tissue.

The cells may further be obtained from a subject with a disease or disorder, for example from a subject with an acquired or congenital cardiac or cardiovascular disorder, disease or dysfunction, for example a cardiac defect. The cell may be of mammalian origin, for instance human, and it may also be a genetically modified cell. Additionally, the mesenchymal stem cells may also be obtained from a young healthy donor (preferably below 35 years of age), for instance through aspirating cells (e.g. around 50 ml) from the bone marrow.

The present invention also pertains to methods to expand Isl1$^+$ progenitors (i.e., progenitors that are already Isl1') by activating or enhancing the Wnt/3-catenin pathway. In particular, the present invention is based on the discovery that activating, increasing, or enhancing Wnt signalling when cells are cultured in the presence of at least one laminin comprising an α5 chain triggers renewal of Isl11 progenitors and can be used to expand Isl1$^+$ progenitors while maintaining their capacity for multi-lineage differentiation. Accordingly, the present invention relates to methods for expanding Isl1$^+$ progenitors, for example Isl1$^+$ cardiovascular progenitors. The activation, increasing, or enhancing of the Wnt canonical pathway is effectuated by at least one agent activating the Wnt canonical pathway. In this context, agents activating the Wnt canonical pathway are any agents which activate the Wnt canonical pathway. Preferably, such agent(s) activate the Wnt canonical pathway in a selective manner. In some embodiments, the agents that activate the Wnt canonical pathway are directly applied to the Isl1+ progenitor, for example, agents that activate the Wnt canonical pathway are applied to the culture media.

In another aspect, the present invention pertains to cells obtainable by the methods of the instant invention, i.e. Isl1+ cells, optionally further differentiated into e.g. cardiac cells, for instance cardiomyocytes (cells differentiated using the methods of the present invention normally display at least a 100-fold increase in Troponin T expression, and frequently a 150-fold increase in expression). The cells as per the present invention may optionally be cryopreserved, in order to enable storage, facilitated handling, and subsequent use and experimentation.

In yet another aspect, the present invention relates to a composition comprising at least one laminin comprising an α5 chain and at least one agent which activates the Wnt canonical pathway. The at least one laminin comprising an α5 chain may be selected from the group comprising laminin 51, laminin 521, a combination of laminin 511 and laminin 521, any natural, recombinant, or synthetic protein, which has at least approximately 70% sequence identity to the polypeptide sequence of laminin 511 or laminin 521, any natural, recombinant, or synthetic protein comprising the polypeptide sequence of the laminin α5 chain G-domain, any natural, recombinant, or synthetic protein comprising a polypeptide sequence, which has at least approximately 70% sequence identity to the polypeptide sequence of the laminin 05 chain G-domain, and any cell culture growth substratum or cell culture medium additive comprising polypeptides from the polypeptide sequence of laminin 511 or laminin 521.

Further in accordance with the present invention, the at least one agent which activates the Wnt canonical pathway, and which is comprised in the composition, may be selected from the group comprising Wnt-1, Wnt-3a, Wnt-8, Wnt-8b, and any combination thereof. Additional agents activating the Wnt canonical pathway are naturally also within the scope of the present invention, irrespective of whether the activation of the Wnt canonical pathway is effectuated via direct activation of the pathway in question (for instance mediated by Wnt-3a) or via indirect stimulation of the Wnt canonical pathway. The composition may be present in a number of different forms, for instance is selected from the group comprising a liquid, a solid, a matrix, a dispersion, a suspension, an emulsion, a microemulsion, a gel, or a solution, and any combination thereof. The composition in accordance with the present invention may for instance be a combination of a liquid (preferably comprising the at least one agent which activates the Wnt canonical pathway) and a substantially solid and/or a gel and/or a matrix (preferably comprising the laminin comprising an α5 chain).

In a further aspect, the instant invention relates to a kit (i.e. a kit of parts) comprising at least one laminin comprising an α5 chain and a cell culture medium comprising at least one agent which activates the Wnt canonical pathway. The components of the kit (i.e. the laminin and the Wnt-activating agent) may advantageously be provided in separate containers (for instance vials, ampoules, tubes, or the like), in order to enable combining the components when carrying out the methods as per the present invention. The kit may for instance comprise a cell culture medium comprising the at least one agent which activates the Wnt canonical pathway (at a suitable concentration), and the at least one laminin comprising an α5 chain, coated e.g. on a surface suitable for cell culture (such as a cell culture plate, a well of a multi-well plate, a petri dish, a cell culture flask, etc.). Furthermore, the kit may also comprise additional components for differentiating the Isl1+ cells to cardiac cells (e.g. cardiomyocytes), namely at least one laminin selected from the group comprising laminin 111, laminin 211, laminin 221, and any combination thereof. A suitable derivation and differentiation kit as per the present invention would thus comprise a cell culture medium comprising the at least one agent which activates the Wnt canonical pathway, at least one laminin comprising an α5 chain, a cell culture differentiation medium that may be devoid of the at least one agent which activates the Wnt canonical pathway, and at least one laminin selected from the group comprising laminin 111, laminin 211, laminin 221, and any combination thereof. In one embodiment, the laminin comprising an α5 chain may be coated on a $1^{st}$ set of cell culture equipment, whereas the at least one laminin selected from the group comprising laminin 111, laminin 211, laminin 221, and any combination thereof, are coated on a $2^{nd}$ set of cell culture equipment, and where a cell culture medium comprising the at least one agent which activates the Wnt canonical pathway is provided in one container whereas cell culture differentiation medium devoid of the Wnt-activating agent(s) is provided in another container.

Additionally, stents or other medical devices for implantation into a human or animal body may also be coated with suitable combinations of either the laminin comprising an α5 chain or the at least one laminin selected from the group comprising laminin 111, laminin 211, laminin 221, and any combination thereof, to enable derivation and/or cardiomyocyte differentiation inside the human or animal body. The stent may comprise gold, cobalt-chromium, tanatalum, nitinol, silicone, polyethylene, and/or polyurethane or any combination thereof. The stents in question may e.g. be a coronary stent, a blood vessel bypass stent, and/or a trachea stent. The stent may be a drug-eluting stent, wherein the drug to be eluted may for instance be a Wnt-activating agent, an agent for vascularisation, an immunomodulating agent, or any other suitable agent(s) to optimize the engraftment and stent function. The stents may be implanted with or without cells, e.g. Isl1+ cells or Isl1+ cells that have been further differentiated into cardiac cells (e.g. cardiomyocytes or cardiac endothelial or smooth muscle cells).

The at least one laminin comprising an α5 chain may be selected from the group comprising laminin 511, laminin 521, a combination of laminin 511 and laminin 521, any natural, recombinant, or synthetic protein, which has at least approximately 70% sequence identity to the polypeptide sequence of laminin 511 or laminin 521, any natural, recombinant, or synthetic protein comprising the polypeptide sequence of the laminin α5 chain G-domain, any natural, recombinant, or synthetic protein comprising a polypeptide sequence, which has at least approximately 90% sequence identity to the polypeptide sequence of the laminin α5 chain G-domain, and any cell culture growth substratum or cell culture medium additive comprising polypeptides from the polypeptide sequence of laminin 511 or laminin 521. Further in accordance with the present invention, the at least one agent which activates the Wnt canonical pathway, and which is comprised in the composition, may be selected from the group comprising Wnt-1, Wnt-3a, Wnt-8, Wnt-8b, and any combination thereof.

In another aspect, the present invention pertains to the cells as per the present invention for use in for use in medicine. More specifically, the cells may be used in the treatment and/or prophylaxis of heart insufficiency, heart failure, myocardial infarction, and/or congenital heart disease due to cardiac defects affecting parts derived from the second heart field (for instance right atrium, right ventricle, outflow tracts (aorta, pulmonary arteries) and ventricular septum). Further, the instant invention also relates to pharmaceutical compositions comprising cells as per the invention, together with at least one pharmaceutically acceptable excipient, for use in medicine, for instance for use in the treatment and/or prophylaxis of heart insufficiency, heart failure, myocardial infarction, and/or congenital heart disease due to cardiac defects affecting parts derived from the second heart field (for instance right atrium, right ventricle, outflow tracts (aorta, pulmonary arteries) and ventricular septum). Both the Isl1+ cells, derived through the derivation methods of the present invention (i.e. through culturing a mesenchymal cell in the presence of at least one laminin comprising an α5 chain, and in a medium comprising at least one agent which activates the Wnt canonical pathway), and the cells that have been further differentiated using the differentiation methods of the present invention (i.e. through culturing in the presence of at least one of laminin 111, laminin 211, laminin 221, or any combination thereof) may be included in a pharmaceutical composition for the treatment or prophylaxis of various illnesses and ailments. The pharmaceutical composition may comprise at least 100,000 ($1*10^5$) cells per ml, preferably at least 500,000 ($5*10^5$) per ml, in a pharmaceutically acceptable carrier, normally an aqueous solution comprising around 9% NaCl.

Furthermore, preferably at least 100,000 cells may be used per kg of body weight, preferably at least 500,000 per kg of body weight, or even more preferably at least 1,000,000 MSCs per kg of body weight.

A further aspect in accordance with the present invention pertains to methods of treatment for improving, alleviating or preventing heart insufficiency, heart failure, myocardial infarction, and/or congenital heart disease due to cardiac defects affecting parts derived from the second heart field (for instance right atrium, right ventricle, outflow tracts (aorta, pulmonary arteries) and ventricular septum) in a subject in need thereof, the method comprising administering to the subject a therapeutically effective amount of the cells according to the instant invention. The subject is preferably a mammal, for instance a human being. The cells may be administered via intravascular administration, intravenous administration, intraventricular administration, epicardial administration, intramuscular administration, intraportal administration, intrathecal administration, and/or subcutaneous administration, or via any other suitable administration method that delivers the cells to the target site/tissue. Specifically, in the context of myocardial infarction, the cells may advantageously be administered to a patient via endovascular injection/infusion or via percutaneous administration in the occluded vessel (before or after re-opening), using a catheter. Additionally, for the treatment of sinus node dysfunction, Isl1+ cells (optionally differentiated into cardiomyocytes, in this case pacemaker cells) may be administered to a patient via percutaneous administration using a catheter introduced into the right atrium, preferably through the sinus coronarius.

Alternatively, the cells of the present invention (either Isl1+ cells or Isl1+ cells further differentiated into cardiomyocytes) may be administered to the patient via the introduction of a suitable stent (e.g. a coronary stent that is introduced in connection with the treatment procedure).

Furthermore, in utero administration of cells may be applied to treat fetal cardiac defects.

In a further aspect, the present invention pertains to the use of a combination of at least one laminin comprising an α5 chain and at least one agent which activates the Wnt canonical pathway, for deriving a multipotent Isl1+ cell (i.e. for inducing a cell to enter a multipotent Isl1+ lineage). The at least one laminin comprising an α5 chain may be selected from the group comprising laminin 511, laminin 521, a combination of laminin 511 and laminin 521, any natural, recombinant, or synthetic protein, which has at least approximately 70% sequence identity to the polypeptide sequence of laminin 511 or laminin 521, any natural, recombinant, or synthetic protein comprising the polypeptide sequence of the laminin α5 chain G-domain, any natural, recombinant, or synthetic protein comprising a polypeptide sequence, which has at least approximately 70% sequence identity to the polypeptide sequence of the laminin α5 chain G-domain, and any cell culture growth substratum or cell culture medium additive comprising polypeptides from the polypeptide sequence of laminin 511 or laminin 521. Further in accordance with the present invention, the at least one agent which activates the Wnt canonical pathway, and which is comprised in the composition, may be selected from the group comprising Wnt-1, Wnt-3a, Wnt-8, Wnt-8b, and any combination thereof.

In another aspect, methods are provided that use the Isl1+ progenitors generated and expanded by the methods described herein. In one embodiment, the Isl1+ progenitors generated and expanded by the methods described herein are used for the production of a pharmaceutical composition, for example a composition for regenerative medicine. Additionally, the Isl1+ cells that have been differentiated into cardiomyocytes may also be used in pharmaceutical compositions, for instance for the treatment of various cardiology-related illnesses and ailments. The compositions may be for use in transplantation into subjects in need of cardiac transplantation, for example but not limited to subjects with congenital and/or acquired heart disease and/or subjects with vascular diseases and/or cardiovascular diseases.

The subjects may have or be at risk of heart disease and/or vascular disease and/or cardiovascular disease, and the Isl1+ progenitors generated and expanded by the methods of the present invention may be autologous and/or allogenic (and the cells may optionally be genetically modified).

The Isl1+ progenitors and the further differentiated cardiac cells generated and expanded by the methods of the present invention may be used in assays and experiments, for instance for screening agents, for example agents for the development of therapeutic interventions of diseases, including, but not limited to, therapeutics for congenital and adult heart failure. Alternatively, the cells of the present invention may be employed in assays for screening agents that are toxic to the cell (e.g. cardiotoxicity tests).

Thus, the present invention provides methods for; (i) triggering or inducing cells, typically mesenchymal stem cells, to enter the Isl1+ lineage pathway by activating the Wnt canonical pathway (i.e. a method for deriving an Isl1+ cell) and culturing in the presence of laminin(s) having certain characteristics, (ii) expanding Isl1+ cells, for example any Isl1+ progenitor of the Isl1+ cardiovascular progenitor hierarchy, by continued renewal of the cells so obtained, and (iii) differentiation of said Isl1+ cells into e.g. cardiac cells, such as cardiomyocytes, smooth muscle cells, and/or endothelial cells.

The at least one agent that activate, increase or enhance the Wnt canonical pathway, herein alternatively termed "agent that activate the Wnt canonical pathway" or "activating agents" shall be understood to comprise agents that activate the Wnt canonical pathway directly or indirectly.

For convenience and clarity, certain terms employed herein collected below. Unless otherwise defined, all technical and scientific terms used herein have the same meaning as commonly understood by one of ordinary skill in the art to which this invention belongs.

The term "laminin" pertains to a family of heterotrimeric glycoproteins composed of α, β, and γ chains that exist, respectively, as five, three, and three genetically distinct types forming 15 different combinations in human tissues. They are named according to the chain composition; for example, laminin-511 (LN-511) consists of α5, β1, and γ1 chains. Earlier, laminins were named according to the order of their discovery. Thus, laminin-111 was named laminin-1; laminin-511 was named laminin-10; laminin-521 was named laminin-11.

Laminins are the main component of basement membranes and are in contact with various cells in vivo and different laminins show various spatio-temoral expression patterns in developing organisms as well tissue-specific location and functions. Thus, laminin-211 and laminin-221 are primarily present in basement membranes around muscle cells and motor neuron synapses, laminin-332 is specific for subepithelial basement membranes, and laminin-511 is practically ubiquitous. The first discovered laminin, laminin-111, which is also known as laminin-1 or just laminin, is restricted to the early embryo and is a very rear isoform in adult human tissues. Laminin-111 has been studied most extensively, because it is possible to isolate it from the mouse Engelbreth-Holm-Swarm (EHS) sarcoma, which is easy to induce. Other laminins are hard to isolate from tissues due to extensive cross-linking and they should preferably be expressed as recombinant proteins in mammalian cells.

The cellular effects of laminins are largely mediated via ligand binding to cell membrane receptors such as integrins, dystroglycan, and Lutheran glycoprotein. They can induce direct outside-in signaling in the cells, which has been shown to alter transcription levels of genes and even influence chromatin remodeling of the gene promoters. Laminins are very different in their ligand specificity. Thus, laminins containing an α5 chain can avidly bind integrin α6β1, integrin α3β1 and Lutheran glycoprotein, while laminin-111 (or laminin) has highest affinity to integrin α7X2β1 and dystroglycan. Laminin β and γ chains can modulate laminin-integrin binding, but the cellular interaction is mediated primarily via binding of the α chains to the receptors. Therefore, α5-containing laminins should be regarded as different from, e.g. α2-containing laminins.

Thus, the term "laminin comprising an α5 chain" used herein refers to any laminin polypeptide comprising an α chain of type five (5), e.g. laminin-511, 521, 522, 523, etc. Additional laminins comprising an α5 chain are naturally also within the scope of the present invention. As used herein, an α5 chain refers to any polypeptide chain that has at least 70% sequence identity to the laminin α5 chain, e.g. of SEQ ID No. 1, preferably a sequence identity of at least 80%, and even more preferably a sequence identify of at least 90%. More generally, all polypeptides and/or nucleotides disclosed in the present application encompass polypeptide and/or nucleotide sequences that have at least 70% sequence identity to the polypeptide and/or nucleotide in question, preferably a sequence identity of at least 80%, and even more preferably a sequence identify of at least 90%.

The term "Isl1$^+$ cell" refers to cells that may under normal circumstances express the following markers (in addition to Isl1); mesodermal markers; Tbx6 and Brachyury T; C-Kit; activation markers of early cardiogenesis: GATA4, Mef2c, Nkx2.5; multipotency markers, such as Sox2, SSEA1, Nanog, Tra-1, KDR, or a combination of these; transcription factors involved in the transcriptional network of the second heart field: Tbx1, Hand2, FoxH1; other relevant factors linked to the Isl1 expression like Fgf8 and 10.

The term "cardiac cell" or "heart cell" or "cardiomyocyte" shall be understood as a cell that may under normal circumstances express markers such as: myosin heavy chains (MyH), Troponin T (TnT) and/or Troponin I (TnI) and the proteins are normally organized in contractile elements.

The term "progenitor cells" or "progenitors" is to be understood to refer to cells that have a cellular phenotype that is more primitive (i.e. is at an earlier stage along a developmental pathway or progression than is a fully differentiated cell) relative to a cell which it can give rise to by differentiation. Progenitor cells also frequently have significant or very high proliferative potential, and they can give rise to multiple distinct differentiated cell types or to a single differentiated cell type, depending on the developmental pathway and on the surrounding environment in which the cells develop and differentiate. A cell can begin as progenitor cell and proceed toward a differentiated phenotype, but then revert and re-express the progenitor cell phenotype. Consequently, a progenitor cell can be derived from a non-stem cell.

The term "stem cell" is to be understood to refer to an undifferentiated cell which is capable of proliferation and to give rise to more progenitor cells having the ability to generate a large number of mother cells which may in turn give rise to differentiated, or differentiable daughter cells. The daughter cells themselves can be induced to proliferate and produce progeny that subsequently differentiate into one or more mature cell types, while at the same time retaining one or more cells with parental developmental potential. The phrase "stem cell" refers to a subset of progenitors that have the capacity or potential, under particular circumstances, to differentiate to a more specialized or differentiated phenotype, and which retains the capacity, under certain circumstances, to proliferate without substantially differentiating. The term "stem cell" may generally refer to a naturally occurring mother cell whose descendants (progeny) specialise, often in different directions, through differentiation, e.g., by acquiring completely individual characters, as occurs in progressive diversification of embryonic cells and/or tissues. Cellular differentiation is a complex process typically occurring through many cell divisions and a differentiated cell may be derived from a multipotent cell which is itself derived from a multipotent cell, etc. While each of these multipotent cells may be considered to be stem cells, the range of cell types each can give rise to may vary substantially. Some differentiated cells also have the capacity to give rise to cells of greater developmental potential and such capacity may be be induced artificially upon treatment with various factors, or may be natural. Stem cells are also in many instances "multipotent" because they can produce progeny of more than one distinct cell type, but this is not required for their "stem-ness." Self-renewal is the other typical part of the stem cell definition, and it is important for the purposes of this invention. Theoretically, self-renewal can occur by either of two major mechanisms, i.e. symmetrically or asymmetrically. Asymmetric division refers to one daughter retaining the stem state and the other daughter expressing some distinct other specific function and phenotype. Symmetric division refers to the process when some of the stem cells in a population divide symmetrically into two stems, thus maintaining some stem cells in the population as a whole, while other cells in the population give rise to differentiated progeny only. It is formally possible that cells that begin as stem cells proceed toward a differentiated phenotype, but then revert and re-express the stem cell phenotype, a process which is often referred to as e.g. "dedifferentiation" or "reprogramming" or "retrodifferentiation".

The term "differentiation" in the present context is to be understood to mean the formation of cells expressing markers or characteristics known to be associated with cells that are more specialized and closer to becoming terminally differentiated cells, which are incapable of further division or differentiation. Progressive differentiation or progressive commitment refers to the pathway along which cells progress from a less committed cell, to a cell that is increasingly committed to a particular cell type, and eventually to a cell that is terminally differentiated. Cell which are more specialized (for instance have begun to progress along a path of progressive differentiation) but not yet terminally differentiated are referred to as partially differentiated. Differentiation is a development process whereby cells acquire a specialized phenotype (for instance acquire one or more characteristics, features, or functions distinct from other cell types). In certain cases, the differentiated phenotype may refer to a cell phenotype that is at the mature endpoint in some developmental pathway (a so called terminally differentiated cell). In many (but not all) tissues, the process of differentiation is connected with exit from the cell cycle and in these instances, the terminally differentiated cells lose or greatly restrict their capacity to proliferate. For the purposes of the present invention, the term "differentiation" or "differentiated" is to be understood to refer to cells that are more specialized in their fate and/or function than at a previous point in their development, consequently including both cells that are terminally differentiated and cells that (although not terminally differentiated) are more specialized than at a previous point in their development.

In the context of cell origins and development (i.e. cell ontogeny), "differentiated", or "differentiating" is a relative term meaning a "differentiated cell" is a cell that has progressed further down a developmental pathway than the cell it is being compared with. Stem cells can thus differentiate to precursor cells restricted to a certain lineage (such as for instance a mesodermal stem cell), which can in turn differentiate into other types of precursor cells further down the pathway in question (such as a cardiomyocyte precursor), and then to a terminally differentiated cell (which may play a characteristic role in a certain tissue type, and may or may not (depending on the circumstances) retain the capacity to proliferate further).

The term "embryonic stem cell" is to be understood to refer to the pluripotent stem cells of the inner cell mass of the embryonic blastocyst, and such cells can also be obtained from the inner cell mass of blastocysts derived from somatic cell nuclear transfer. The distinguishing features of an embryonic stem cell define an embryonic stem cell phenotype.

Consequently, a cell has the phenotype of an embryonic stem cell if it possesses one or more of the unique characteristics/features of an embryonic stem cell, such that the cell is distinguishable from other cells. Exemplary distinguishing embryonic stem cell characteristics/features include but are not limited to proliferative capacity, gene expression profile, karyotype, differentiation capacity, responsiveness to particular culture conditions, as well as possible additional characteristics/features.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Examples of adult stem cells include but are not limited to mesenchymal stem cells, hematopoietic stem cells, neural stem cells, neural crest stem cells, and pancreatic stem cells. As indicated above, stem cells have been found resident in basically every tissue type and within the context of the present invention, therefore, stem cell populations can be isolated from virtually any animal tissue.

The terms "proliferating" and "proliferation" is to be understood to refer to an increase in the number of cells in a population (growth) by means of cell division. Cell proliferation is generally understood to be an implication of coordinated activation of multiple signal transduction pathways (in response to the environment surrounding a cell), including growth factors and other mitogens. Cell proliferation may also be promoted by release from negative or blocking actions of intra- and/or extracellular signals and mechanisms.

The terms "renewal" or "self-renewal" or "proliferation" are used interchangeably herein, and are to be understood to refer to the ability of stem cells to renew themselves by dividing into the same non-specialized cell type over long periods, for instance many months to years. Proliferation may in some cases refer to expansion of cells by the repeated division of a single cell into two identical daughter cells.

The term "embryonic" may within the context of the present invention be used to refer to fetal material (i.e. cells or tissues), i.e. cells/tissues obtainable from a developing foetus. By definition, an embryo enters the foetal stage (i.e. becomes a foetus) at the time of organogenesis (i.e. when organs start to form) and the tissues and cells used in certain examples in accordance with the present invention are obtained from foetal material, i.e. from gestational week 6-10. Normally, the definition in humans is that the embryonic period stretches from fertilization to the eight week after fertilization, whereas the period starting from the eight week and lasting till partus is defined as the fetal period. Essentially, within the context of the present invention, when pre-natal cells and/or tissues are utilized they are normally of a fetal character, but sometimes also of an embryonic character.

The terms "mesenchymal cell" or "mesenchyme" or "cells from a mesenchymal fraction" or "mesenchymal stem cells" or "MSCs" are used interchangeably herein and may for the purposes of the present invention refer to in some instances the fusiform or stellate cells that are found between the ectoderm and endoderm of young embryos, or cells that are found in adult tissue such as bone marrow, mesoderm, umbilical cord blood, Wharton's jelly, adult muscle, developing tooth buds, and/or amniotic fluid. Most mesenchymal cells are derived from established mesodermal layers, but they may also develop from neural crest or neural tube ectoderm in the cephalic region. A "mesenchymal stem cell" or a "mesenchymal cell" is to be understood to refer to a cell from any suitable adult tissue such as bone marrow, mesoderm, umbilical cord blood, Wharton's jelly, adult muscle, developing tooth buds, and/or amniotic fluid, or from fetal or embryonic connective tissue. Furthermore, induced pluripotent stem cells (i.e. iPS cells), which may be derived from e.g. a human fibroblast, a human hepatocyte, and/or a human blood cell, may be utilized in the context of the present invention to derive Isl1+ cells. Further, mesenchymal progenitor or mesodermal progenitors may refer to progenitor cells of mesodermal origin. The mesoderm is the middle embryonic germ layer, lying between the ectoderm and the endoderm, from which connective tissue, muscle, bone, and the urogenital and circulatory systems develop. A cell from the "mesenchymal fraction" shall within the context of the present invention be understood to relate to any type of mesenchymal cell (i.e. a mesenchymal stem cell (MSC)) that may be derived from e.g. any of the following sources: bone marrow, mesoderm, umbilical cord blood, Wharton's jelly, adult muscle, developing tooth buds, and/or amniotic fluid. The MSCs as per the present invention may for instance be obtained by aspiration from the bone marrow, or by isolation from umbilical cord blood, or extracted from the mesoderm of either a foetus and/or an embryo.

The term "lineages" as used herein is to be understood to pertain to a cell with a common ancestry or cells with a common developmental fate. A cell that has entered an "islet 1+ lineage" is to be understood to refer to the cell as being an Isl1' progenitor and expressing Isl1+, and which may differentiate along the Isl1+ progenitor lineage restricted pathways. Such pathways may be one or more developmental lineage pathways, for instance an endothelial lineage, a cardiac lineage or a smooth muscle lineage. For example, a cell that has entered the Isl1+ lineage is a cell which is has the capacity of differentiating into three major cell types in the heart (i.e. cardiac, smooth muscle, and endothelial cells).

A "marker" is to be understood to describe the characteristics/features and/or phenotype of a cell and markers can often be used for selection/identification of cells comprising characteristics of interests. Markers will vary with specific cells. Markers are characteristics, whether morphological, functional or biochemical (enzymatic) characteristics of the cell of a particular cell type, or molecules expressed by the cell type. Markers are preferably proteins and more preferably possess at least one epitope for antibodies or other binding molecules that may be available. However, a marker may be any molecule found in or on a cell including but not limited to proteins (peptides and polypeptides), polysaccharides, nucleic acids, lipids, and steroids. Some examples of morphological characteristics/features or traits include for instance shape, size, and nuclear-to-cytoplasmic ratio. Examples of functional characteristics or traits comprise for instance the capacity to migrate under certain conditions, the ability to adhere to certain substrates, and the capacity to differentiate along particular lineages.

The terms "subject" and "individual" and "patient" may be used interchangeably herein and are to be understood to refer to an animal, for instance a human being, from whom cells can be obtained and/or to whom treatment, including prophylaxis or preventative treatment (for instance using the cells as per the present invention) is provided. Advantageously, the subject of the treatments as described in the context of the present invention is a mammal, preferably a human, or other mammals, preferably domesticated or production mammals.

Cardiovascular diseases, conditions or disorders are to be understood to comprise medical conditions related to the cardiovascular (heart) or circulatory system (blood vessels). A response to myocardial injury follows a clearly defined path in which some cells die while others enter a state of hibernation (wherein they are not yet dead but are dysfunctional). This is followed by infiltration of inflammatory cells and deposition of collagen as part of a scarring process. This happens in parallel with in-growth of new blood vessels and a certain extent of continued cell death. The term cardiovascular diseases is intended to comprise all disorders and diseases characterized by insufficient, undesired or abnormal cardiac function, for instance congenital heart disease and any condition which leads to congestive heart failure in a subject, particularly a human subject, ischemic heart disease, hypertensive heart disease and pulmonary hypertensive heart disease, and valvular disease. Insufficient or abnormal cardiac function can an implication of disease, injury, trauma, and/or aging, comprising for instance diseases and/or disorders of the pericardium, heart valves (for instance stenosed valves, incompetent valves, rheumatic heart disease, aortic regurgitation, mitral valve prolapse), myocardium (myocardial infarction, coronary artery disease, heart failure, angina, ischemic heart disease) blood vessels (for instance arteriosclerosis or aneurysm) or veins (for instance varicose veins, hemorrhoids). The term "ischemia" is to be understood to refer to any localized tissue ischemia due to reduction of the inflow of blood, and the term "myocardial ischemia" is to be understood to comprise circulatory disturbances caused by coronary atherosclerosis and/or inadequate oxygen supply to the myocardium. An acute myocardial infarction may represent an irreversible ischemic insult to myocardial tissue. This insult may result in an occlusive (for instance thrombotic or embolic) event in the coronary circulation, producing a milieu in which the myocardial metabolic demands are exceeding the supply of oxygen to the myocardial tissue.

The term "agent" refers to any chemical, entity or moiety, comprising for instance (without any limitation) synthetic and naturally-occurring non-proteinaceous and proteinaceous entities. An agent may be a nucleic acid, nucleic acid analogues, peptides, proteins, antibodies, aptamers, oligomers of amino acids, nucleic acids, or carbohydrates comprising for instance oligonucleotides, ribozymes, DNAzymes, glycoproteins, proteins, siRNAs, lipoproteins, aptamers, and any modifications and combinations thereof. Agents are to also be understood to possibly include small molecules having certain chemical moieties, comprising for instance chemical moieties such as unsubstituted or substituted alkyl, aromatic, or heterocyclyl moieties including macrolides, leptomycins, and related natural products or analogues thereof. As used herein, the term "Wnt activating agent" refers any agent that activates the Wnt canonical pathway, or inhibits or suppresses the activity of inhibitors of Wnt canonical pathway. The activation is preferably selective activation, which means that the Wnt3 pathway is activated to the substantial exclusion of the effects (i.e. activation of inhibition) on non-Wnt3 pathways.

The term "therapeutically effective amount" is to be understood to refer to an amount that results in an improvement, alleviation, or remediation of the disease, disorder, or symptoms of the disease or condition.

The terms "administering," "introducing" and "transplanting" are used interchangeably for the purposes of the present invention, for instance in the context of the placement of Isl1+ progenitors (for example Isl1+ cells or Troponin T-expressing cardiomyocytes differentiated using the methods of the present invention) into a subject. A suitable method or route is one which leads to at least partial localization of the cardiovascular stem cells at a desired site. The cells may be administered (delivered) by any appropriate route which results in delivery to a desired location/tissue/site in the subject where at least a portion of the cells or components of the cells remain viable (the period of viability of the cells after administration may be as short as a few hours to a few days, to as long as several years).

The modes of administration suitable for the purposes of the present invention comprise for instance (without limitation) intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

The phrase "pharmaceutically acceptable excipient" as used herein is to be understood to relate to a pharmaceutically acceptable material, composition or vehicle, for instance a solid or liquid filler, a diluent, an excipient, a carrier, a solvent or a encapsulating material, involved in suspending, maintaining the activity of or carrying or transporting the subject agents from one organ, or portion of the body, to another organ, or portion of the body.

The term "derivative" or "variant" as used herein is to be understood to refer to for instance a peptide, chemical or nucleic acid that differs from the naturally occurring polypeptide or nucleic acid by at least one amino acid or nucleic acid, for instance deletions, additions, substitutions or side-chain modifications, but at the same time retains one or more specific functions and/or activities of the naturally occurring molecule. Amino acid substitutions may comprise alterations in which an amino acid is replaced with a different naturally occurring or a non-conventional amino acid residue, and these substitutions may be conservative or non-conservative. The present invention pertains inter alia to use of agents that activate the Wnt canonical pathway. Examples of Wnt activating agents may include for example polypeptides, peptides, nucleic acids nucleic acid analogues, phage, peptidomimetics, antibodies, small or large organic molecules, ribozymes or inorganic molecules or any combination of thereof (optionally naturally occurring). The agents that activate the Wnt canonical pathway may include for example antibodies (polyclonal or monoclonal), neutralizing antibodies, antigen-binding antibody fragments, peptides, proteins, peptidomimetics, aptamers, oligonucleotides, hormones, small molecules, nucleic acids, nucleic acid analogues, carbohydrates or variants thereof that function to inactivate or activate one or more, as the case may be, nucleic acid and/or protein participant in a Wnt pathway as described herein or as known in the art. It shall be understood that the above described exemplifying embodiments can be modified without departing from the scope of the invention, inter alia with respect to the described constituents, materials, and process parameters applied. The invention will now be further exemplified with the enclosed examples, which naturally also can be modified without departing from the scope of the invention.

Experimental Section

In order to develop a feeder free culturing system where the origin and expansion of the Isl1+ cells could be followed, the inventors synthesized a plasmid construct comprising parts of the Isl1-promoter region linked to the fluorescent marker green fluorescent protein (GFP). The plasmid was introduced into the cells by means of electroporation. Mesenchymal cells (i) derived from rat embryonic hearts, (ii) obtained from rat bone marrow, (iii) obtained from the bone marrow of young healthy donors, (iv) obtained from human cord blood, or (v) isolated from human amniotic sources, were labeled with the Isl1 gene construct concomitant to the addition of Wnt-containing medium (100 ng/ml Wnt-3a and 2.5 mM BIO). The feeder cells used in previous studies were in this protocol replaced with dishes pre-coated with various laminins comprising an α5 chain (notably laminins 511, laminin 521, and a combination thereof). In culture the cells grew to confluency and were passaged every other day. At each passage, cells were analysed immunohistochemically for the expression of Isl1. With each successive passage the ratio of Isl1+ cells increased, which also corresponded to the Isl1 expression registered directly on the plate through activation of the Isl1 gene construct. In the initial fraction less than 1% of the cells expressed Isl1, which increased to 73±18% after two weeks in culture. Within two weeks, the Isl1+ cell population had expanded 16 times from the initiation of the Wnt+laminin-protocol and 35% of the cells were still proliferating expressing Ki67 at the end of the culturing process.

Pure populations of Isl1+ cells have not previously been derived from human fetal or embryonic hearts. To study the ability of the adherent fraction of human fetal or embryonic hearts (gestational weeks 5 to 10) to give rise to Isl1+ cells, these cells, and cells aspirated from human bone marrow or isolated from cord blood, were labeled with the Isl1+ gene construct after the cells had grown to confluence and before being seeded on plates pre-coated with α5-containing laminin(s) in accordance with the present invention. Additionally, 100 ng/ml Wnt-3a was again utilized to activate the Wnt canonical pathway, but this time BIO was excluded and the concentration of fetal bovine serum (FBS) was increased to 10%, cells proliferated in a similar manner to rat Isl1$^+$ cells. These cells demonstrated a similar growth pattern as the rat cells and MSCs from other human tissues (i.e. mesenchymal cells obtainable from bone marrow, amniotic or cord blood cells), and after two weeks the cells had expanded almost 70 times from the initiation of the protocol, generating 92±2% pure populations of Isl1+ cells. At the end of the culturing process, more than 40% of the cells were still proliferating expressing Ki67.

Figure 3:
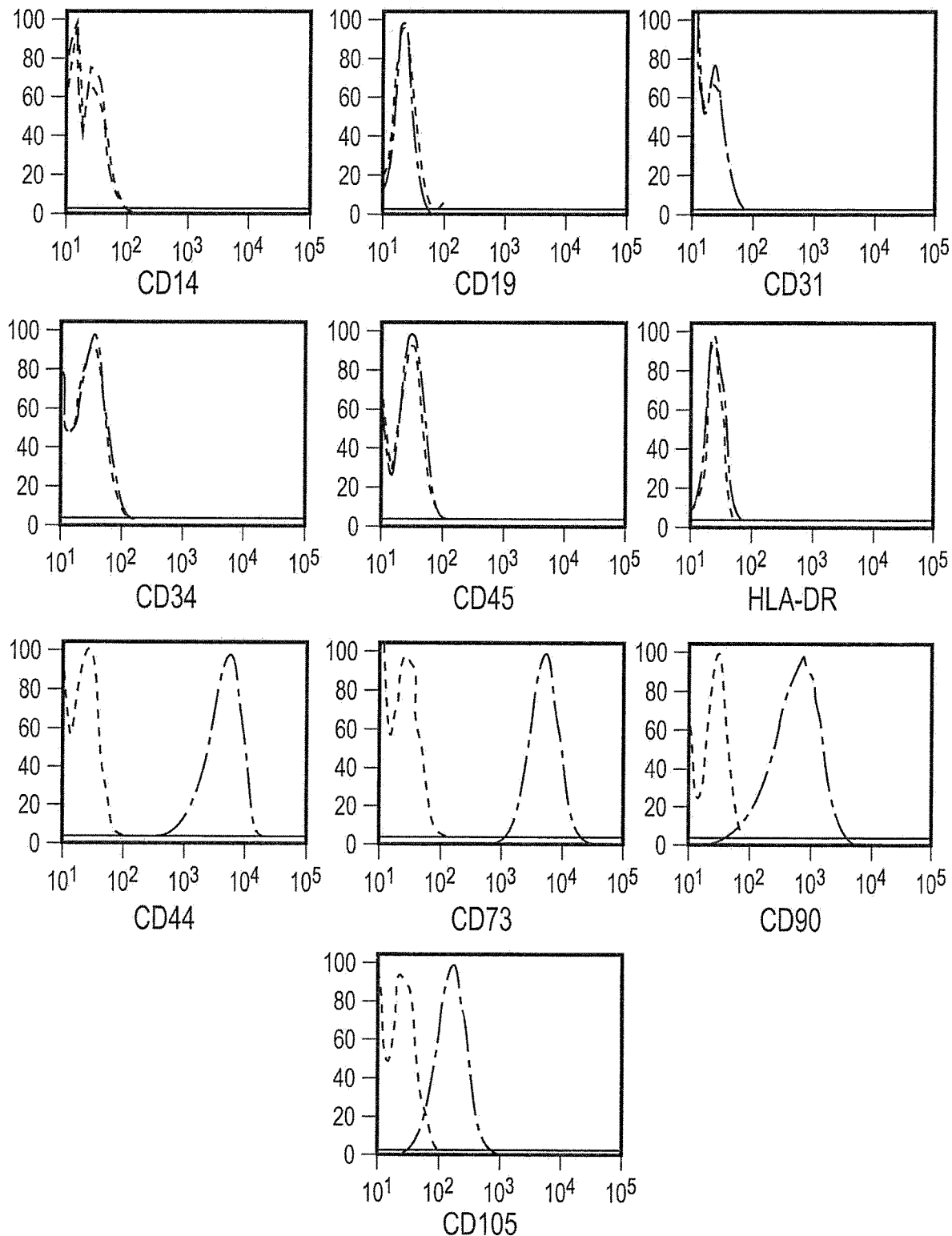
FIG. 3 Flow cytometry analysis of the adherent fraction from a human fetal/embryonic heart and bone marrow aspirate from healthy human donors. The cells expressed the mesenchymal stem cell markers CD105, CD90, CD73 and CD44, while being negative for the hematopoietic lineage markers CD14, CD19, CD34, CD45 and the endothelial marker CD31.

The initial adherent fraction of the fetal/embryonic hearts, that give rise to both human and rat Isl1+ cells, have a similar appearance as mesenchymal stem cells. These cells can be characterized as regards to their expression of surface antigens. We therefore prepared adherent cells from human embryonic hearts (gestational week 6), which were expanded for five weeks followed by FACS analysis using the mesenchymal panel. The adherent fraction expressed the mesenchymal stem cell markers CD105, CD90, CD73 and CD44, while being negative for the hematopoietic lineage markers CD14, CD19, CD34, CD45 and endothelial marker CD31 (FIG. 3). Similar expression profiles were detected using mesenchymal cells obtainable from bone marrow or cord blood cells. In order to ensure that the cells did not change their phenotype during expansion, samples of cells from the different sources were removed and stimulated according to the Wnt/laminin-protocol. This yielded similar amounts and ratio of Isl1+ cells. These findings lead us to conclude that Isl1+ cells can be generated from various mesenchymal cell sources by stimulation of the Wnt canonical pathway when culturing on laminin(s) comprising an α5 chain.

Figure 4A:
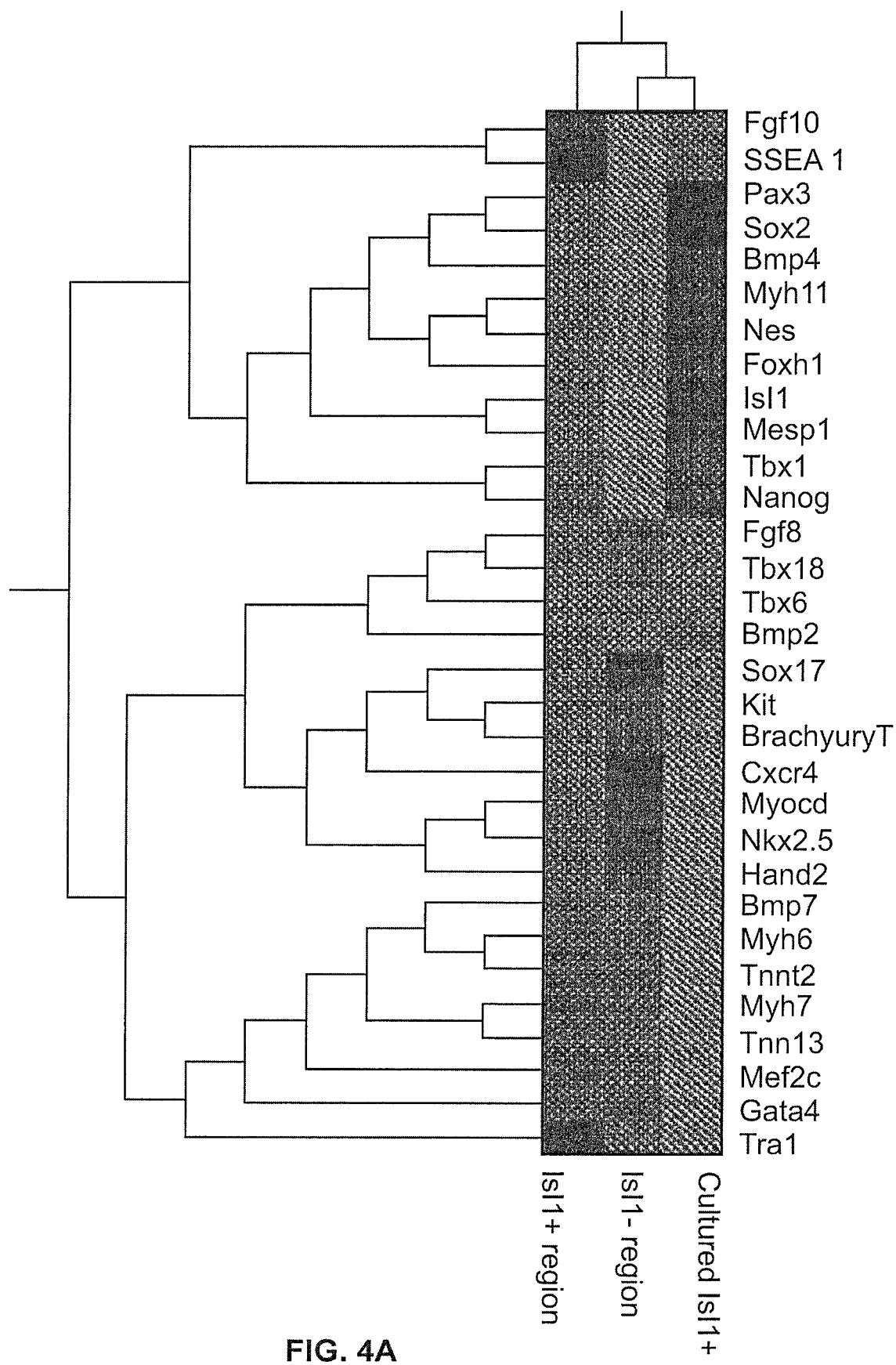
FIGS. 4A-B Heat maps representative of the gene-expression profiles of cultured Isl1+ cells in comparison to in vivo present cells in the Isl1-positive and -negative regions of a fetal heart. The origin of the cells is in (FIG. 4A) rat and (FIG. 4B) human. Average linkage and log 2 transformation of signals are presented. The heatmap color scale range from red (high expression) via black (average expression) to green (low expression).
Figure 4B:
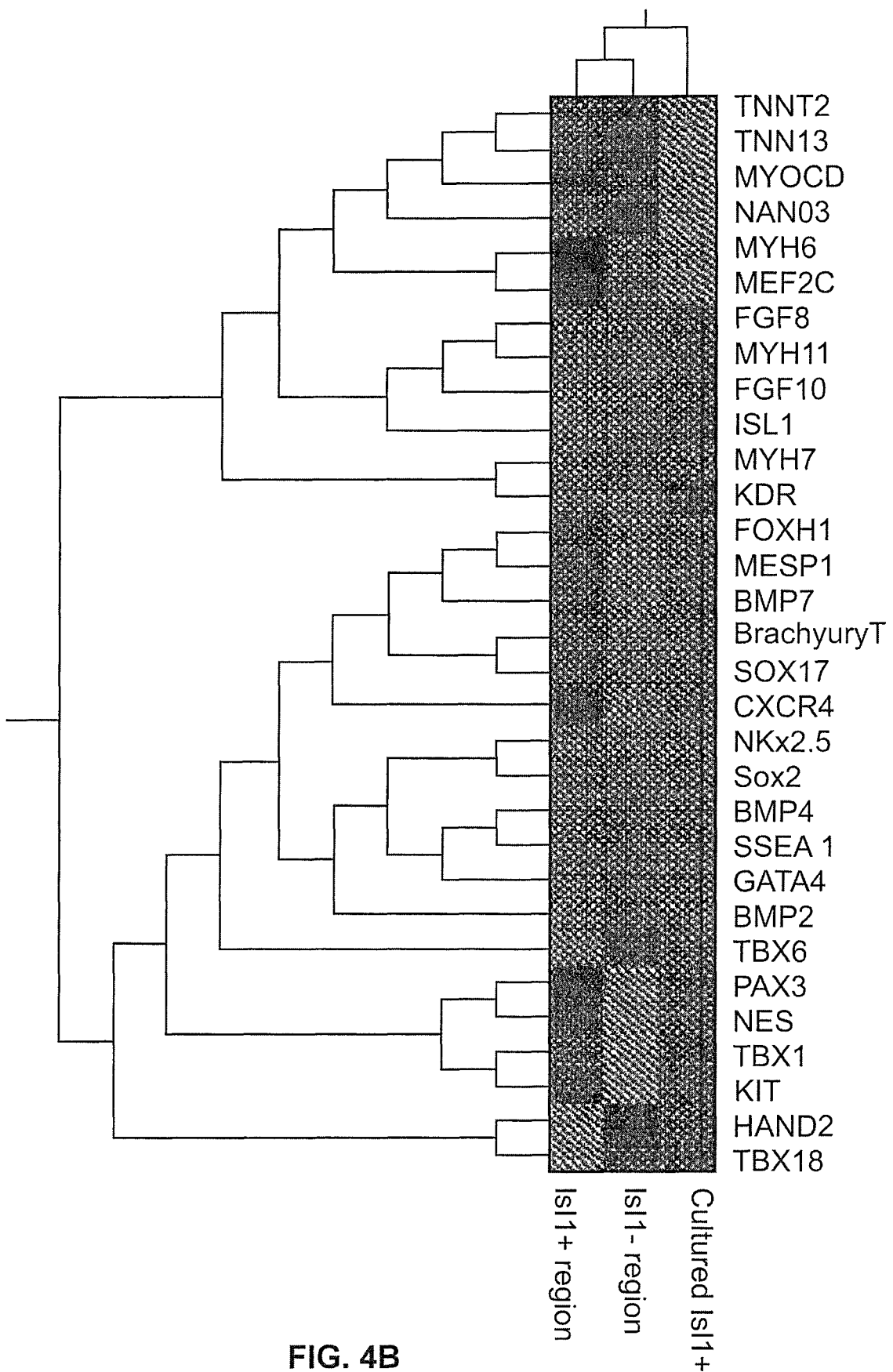
Figure 5A:
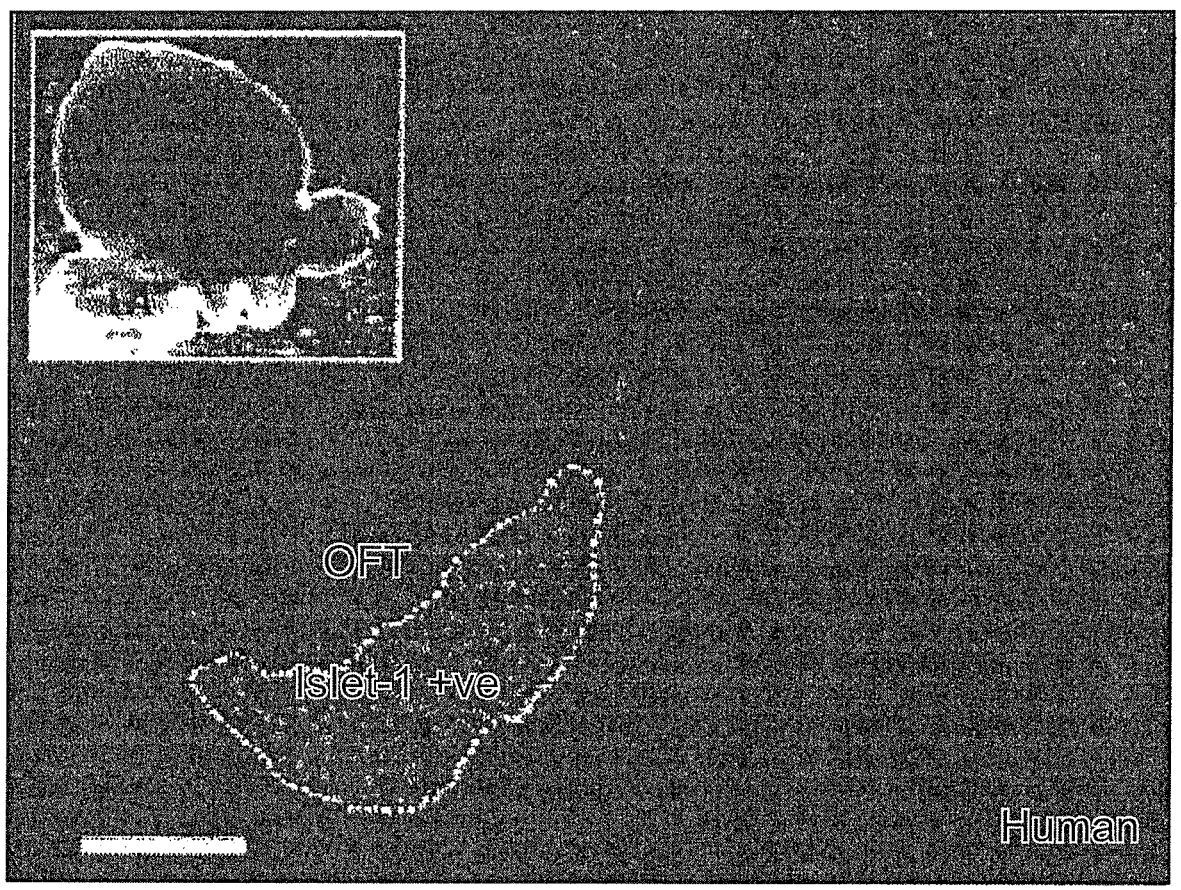
FIGS. 5A-C Heat map representative of the gene-expression profile and flow cytometry analysis defining different progenitor populations of the cultured human Isl1+ cells.
Figure 5B:
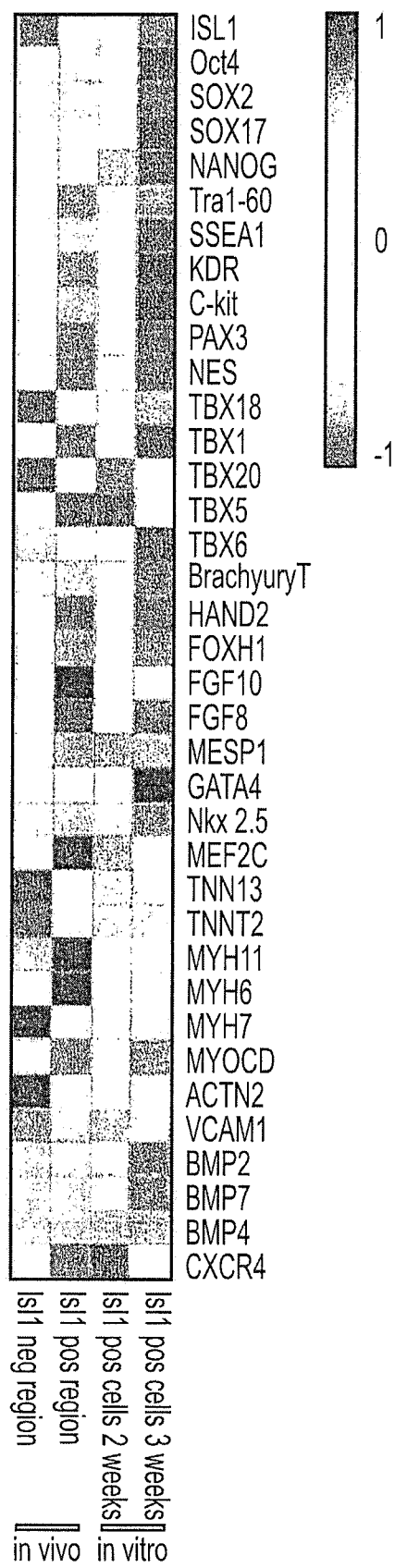
Figure 5C:
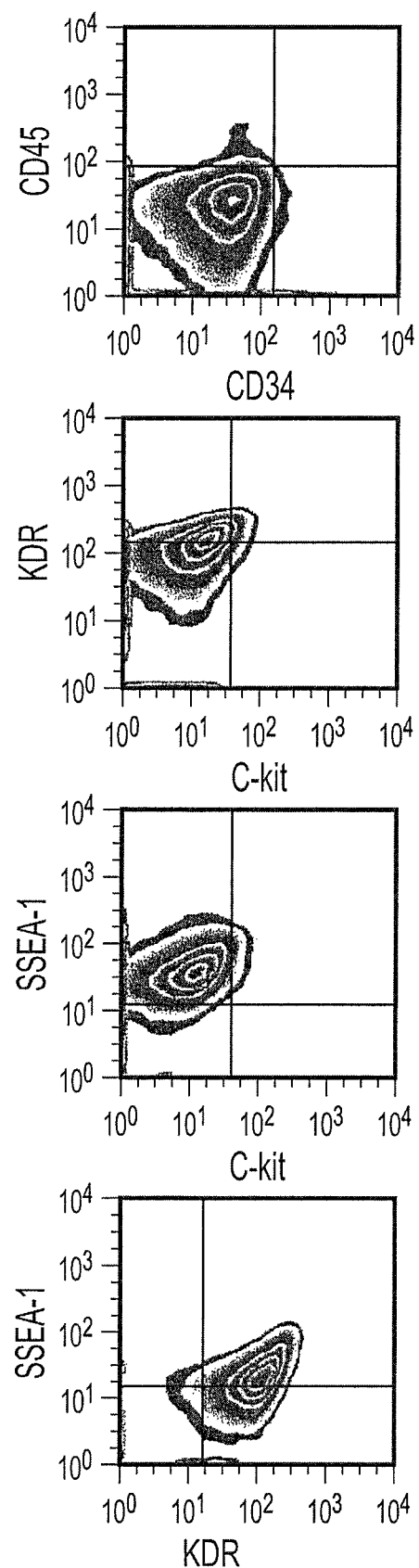
Figure 6A:
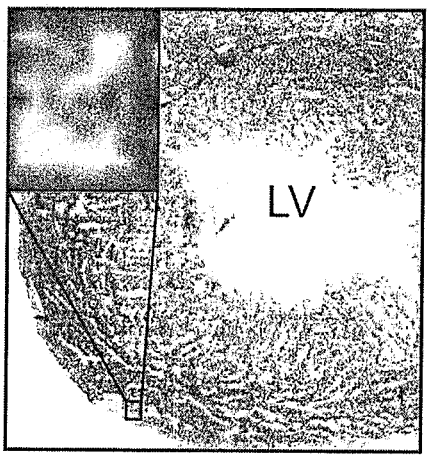
FIGS. 6A-F Detection by immunohistochemistry of the implanted rat Isl1+ cells (obtained either from embryonic or fetal heart or from rat bone marrow) labelled with luciferase and β-gal expressing transposons.
Figure 6B:
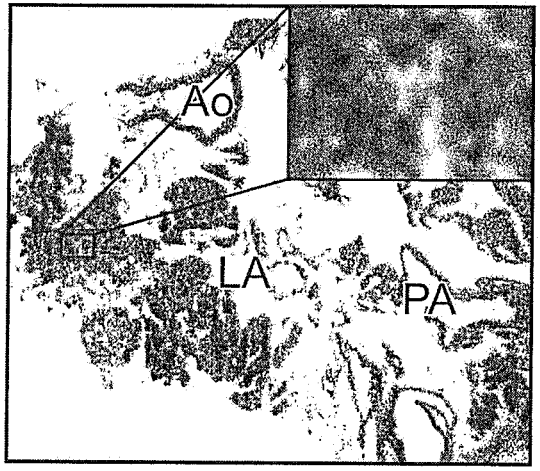
Figure 6C:
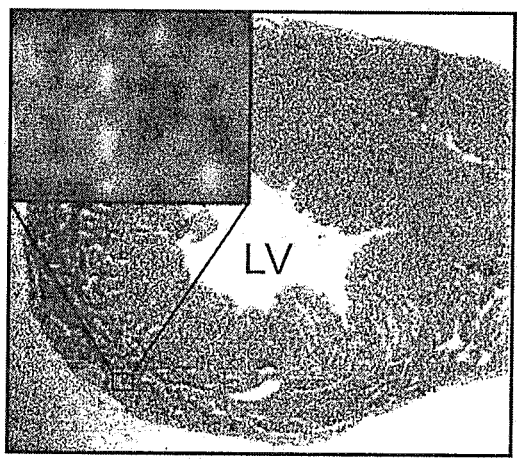
Figure 6D:
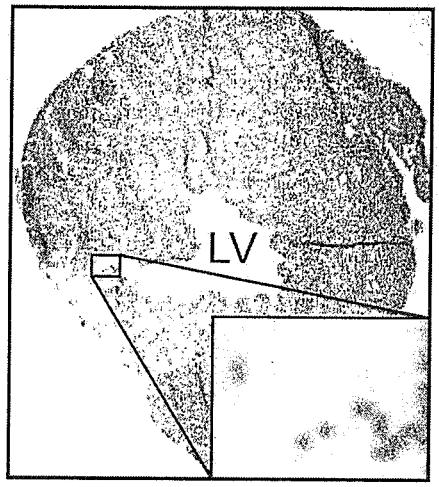
Figure 6E:
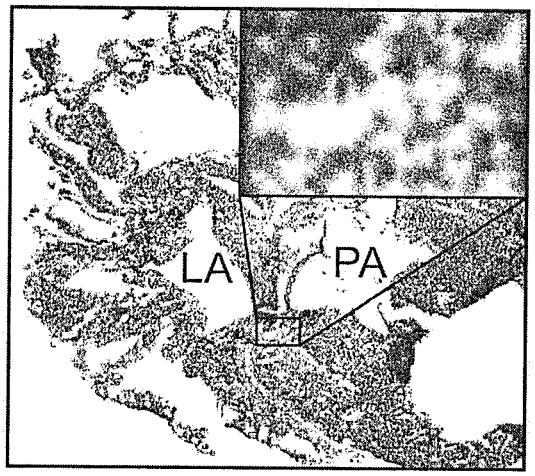
Figure 6F:
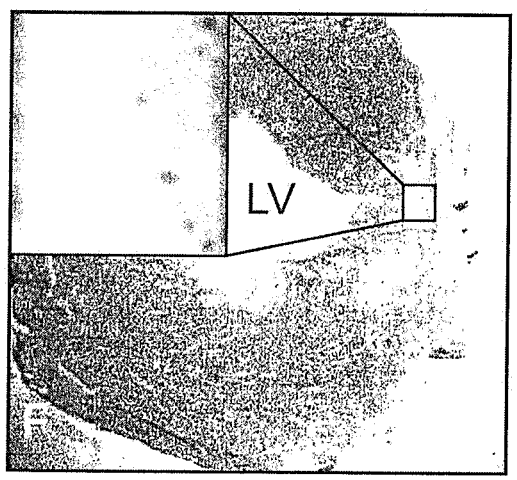
Figure 7:
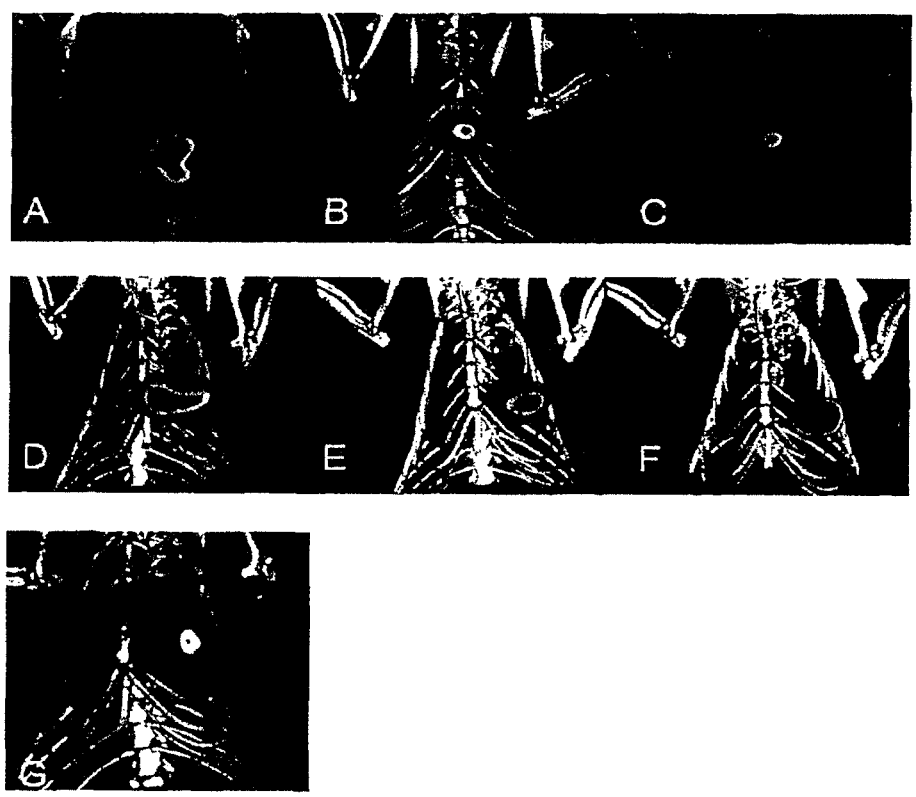
FIGS. 7A-G Study of in vivo survival and migration of rat Isl1+ cells (obtained either from bone marrow or from embryonic heart) labelled with luciferase and β-gal expressing transposons.

The gene-expression profile of cultured rat and human Isl1+ cells were studied and compared to the Isl1+ cells present in vivo in the embryonic hearts (FIG. 4). These studies were performed in order to confirm that the cultured Isl1+ cells were similar to the Isl1+ cells that give rise to the second heart field (SHF). In order to identify a core group of transcription factors that most probably are activated in Isl1+ cells, we identified relevant transcription factors shown to be important for regulating the SHF development in mice. These studies have identified a set of transcription factors that are intimately involved in the transcriptional network of the SHF. These include members of the NK class of homeodomain proteins, the zinc-finger transcription factor GATA4, the MADS domain transcription factor Mef2c, T-box and Forkhead transcription factors as well as Hand class of basic-loop-helix (Hand) factors. Downstream to the Isl1 transcription factor, the Isl1-GATA4-Mef2c pathway seems to be playing a pivotal role for activation of the cascade that induces derivation of cardiomyocytes. The Isl1 and GATA4 factors seem to interact to induce activation of the Mef2c transcription factor, followed by upregulation of the transcription factors Nkx2.5 and Hand2. Other key-regulators of the SHF, are the Forkhead transcription factor FoxH1, the Tbx1 transcription factor, which is dependent on Forkhead factors for its activation and finally Fgf8, which in turn is regulated by Tbx1. Furthermore, blockage of Fgf-signaling prevents expansion of Isl1+ cells in the SHF, indicating an upstream effect on the Isl1-pathway. The cultured rat and human Isl1+ cells express the mesodermal markers TBX6 and Brachyury T, together with the above-mentioned key transcription factors involved in the transcriptional network of the SHF, i.e. Isl1, Mef2c, Nkx2.5, FoxH1, Tbx1, Fgf8 and Fgf10. Furthermore, they also express the early cardiomyocyte marker mesoderm posterior 1 (MESP1), while being negative for the more mature cardiomyocyte markers troponin I (TnI), troponin T (TnT) and myosin heavy chains (Myh) 6 and 7.

The cultured Isl1+ cells demonstrate a similar gene-expression profile as the Isl1+ cells isolated from the embryonic hearts, except that these cells have an even higher expression of the late cardiomyocyte markers Myh, TnT and TnI. In the cultured human Isl1+ cells, the Isl1-GATA4-MEF2c pathway is more upregulated than in both the cultured rat Isl1+ cells and in the in vivo present Isl1+ cells. This correlates well with the upregulation of bone morphogenic peptides (BMPs), which are important for stimulation of early cardiogenesis and concomitant upregulation of the early cardiomyocyte markers Nkx2.5 and MESP1.

Other important findings are that both the cultured and the in vivo present Isl1+ cells express the pluripotency markers Tra-1, Sox2, Nanog and stage-specific embryonic antigen-1 (SSEA-1) while at the same time expressing nestin (NES), paired box 3 (PAX3), known to be expressed in neural crest cells and to a smaller extent the smooth muscle markers myocardin (MYOCD) and Myh11.

According to micro-array data the cultured human and rat Isl1+ cells are multipotent stem cells with a genetic signature (Isl1+, KDR+, Nkx2.5+, Mef2c+) that has shown to be effective in differentiating into the three cardiovascular lineages with emphasis on cardiomyocytes. The cultured Isl1+ cells also express the stem cell markers C-Kit, the epicardial marker Tbx18, together with the multipotent surface marker SSEA1, which make the relationship between these selection markers used to identify different populations of cardiac progenitors a bit confusing. Perhaps these markers identify different states of activation of Isl1+ cells, which at the same time demonstrates the plasticity of these cells.

In prior studies we have shown that Isl1+ cells are during the embryonic and post-natal period localized to the outflow tract (OFT). Even in the adult heart, resident Isl1+ cells can be found in this region and respond to ischemia by migrating from the OFT into the ischemic regions. This could imply that Isl1+ cells respond to myocardial ischemia by actively homing into this region. In order to follow the homing capacity of Isl1+ cells in vivo and at the same time confirm this migration immunohistochemically, the cells were labelled with luciferase and β-gal expressing transposons by means of electroporation. Cells expressing luciferase can be followed in vivo with bioluminescent imaging and n-gal expressing cells can be stained for immunohistochemistry. By utilising the Sleeping-Beauty-100X (SB-100X) transposon system the transgenes were stably integrated into the genome. Labeled rat Isl1+ cells, were injected into the left ventricle wall in immunoincompetent rats and the migration of the Isl1+ cells was detected by an In Vivo Imaging System (IVIS®Spectrum CT) (PerkinElmer Inc., USA). Within 24 hours, the majority of the Isl1+ cells have started to migrate towards the outflow tract and to a lesser extent there were cells left at the site of injection (FIGS. 5A-C and 6A-C). In contrast, if the Isl1+ cells were injected into the peri-ischemic region induced by ligation of the left anterior descending artery (LAD), the majority of the cells did not migrate to the OFT. Instead they were found in the infarct where they at 2 weeks had become elongated and arranged in parallel to the surrounding cardiomyocytes. In order to further characterize the homing ability of Isl1+ cells, they were injected into the left ventricle of normal hearts and their migration followed with IVIS. Within 24 hours the Isl1+ cells were detected in the OFT, but after induction of myocardial Infarction through LAD ligation, the cells migrated into the ischemic region. To further study the homing characteristics of Isl1+ cells, a myocardial infarction was induced followed by intravenous administration of labeled Isl1+ cells through a tail vein. Again the cells migrated to the myocardial Infarct. These results imply that the Isl1+ cells have the ability to home, especially to ischemic regions of the heart but also to areas where the Isl1+ cells are resident in the embryonic and adult heart. The explanation for this migratory response might be that during myocardial ischemia, the surrounding cardiomyocytes up-regulate CXCR4, which is the receptor for stromal cell derived factor-1 (SDF-1). Mesenchymal stem cells are known to express SDF-1 and during ischemia these cells home from the circulation into the infarcted region stimulated through the SDF-1-CXCR4 axis. Moreover, engrafted mesenchymal stem cells secrete SDF-1, which were shown to cause homing of the cardiac progenitors into the infarct. According to our micro-array data, both cultured and especially in vivo present Isl1+ cells express CXCR4, which probably mediates the homing of Isl1+ cells into the ischemic region. The SDF-1-CXCR4 axis might also be important for homing of Isl1+ cells into the OFT of a normal heart, since in vivo present Isl1+ cells have a high expression of this receptor.

In this study we have shown that it is possible to derive pure populations of rat and human Isl1+ cells from mesenchymal cells from the bone marrow of healthy young donors, from mesenchymal cells obtained from cord blood, from amniotic sac sources, and from embryonic/fetal cardiac mesenchymal cells in a culturing system where feeder cells have been replaced by laminins comprising an α5 chain (notably laminins 511, laminin 521, and a combination thereof), and where we use a culturing medium that stimulates the Wnt canonical pathway. Both the human and rat Isl1+ cells have a similar gene-expression profile as their respective in vivo present cells, but they are more immature. The cultured Isl1+ cells have a genetic signature that is favorable for differentiation into the three cardiovascular lineages and they actively home into ischemic myocardium. In this study we have also devised a method for differentiating Isl1+ cells into cardiac cells (cardiomyocytes, smooth muscle cells, and endothelial cells), by including either laminin 111, 211, or 221, or any combination thereof, in the culture medium. These characteristics are beneficial for the use of Isl1+ cells to repair damaged hearts after myocardial infarction. Another field is the congenital heart diseases, where defects affecting the aortic arch, proximal pulmonary arteries and the outflow tract account for almost 30% of all congenital cardiac defects. These defects might be due to alterations in SHF migration, differentiation or proliferation and perhaps in the future, ex vivo cultured Isl1+ cells can be used for in utero treatment of these cardiac defects. This reflects the magnitude of importance of our findings, which hopefully will add a new dimension to regenerative cardiology.

Animals and Ethics

The animal care committée of the Karolinska University Hospital approved all experimental animal procedures. Pregnant Sprague-Dawley (B&K Universal AB, Sollentuna, Sweden), gestational day 14 and Rowett nude rats (RNU, genotype rn/mu) (Charles River Deutchland Inc., Germany) weighing 250-300 g were used in this study. To collect bone marrow tissue and cord blood individual permission was obtained using a standard informed consent procedure and prior approval by the regional ethical committee. To collect human embryonic tissue (gestational weeks 5 to 10), individual permission was obtained using a standard informed consent procedure and prior approval by the regional ethical committee. The investigation conforms to the principles outlined in the Declaration of Helsinki.

Cloning of the Isl1-Promoter Construct and Transfection of the Mesenchymal Cells A 3 kb genomic human DNA fragment upstream of an Isl1 start codon (−3 to −3170 from ATG) was amplified by PCR with a high-fidelity Phusion DNA polymerase (Thermo Scientific). Forward primer 5'-aaa gag ctc GGT GTA ACA GCC ACA TTT-3' and reverse primer 5'-gga gaa ttc CTG TAA GAG GGA GTA ATG TC-3'. The PCR product was cloned into the MCS of the vector pEGFP-1 (Clontech Laboratories Inc, USA) between the restriction enzyme cleavage sites SacI and EcoRI. The Isl1-plasmid was introduced into the rat and human cells using the Neon™ Electroporation system (Invitrogen, US). Pig pancreatic Isl1+ cells were used as positive controls, while Human Aortic Endothelial Cells (HAEC) were used as negative controls for the Isl1-gene construct.

Derivation and Expansion of Isl1+ Cells from Embryonic Rat Hearts

For each experiment 10 pregnant sprague-dawley rats (gestational day, GD, 13 to 14) were used. The rats were eutanized in a $CO_2$ chamber after which the whole embryos (approximately 10 embryos/rat) were removed through a low midline abdominal incision. From each embryo the heart was removed under microscope, minced into small pieces and rinced repetitively with Hank's buffered salt solution (HBSS) (GibcoBRL, NY, USA). The heart pieces were then predigested over night in 4° C. in 0.5 mg/ml Trypsin-solution in HBSS. The next step was to prepare the mesenchymal fraction, which is a modification of the protocol developed by Laugwitz and coworkers (Laugwitz et al., 2005). The predigested heart pieces were treated with collagenase type II (Worthington Biochemical Corp, Lakewood, N.J.) 240 U/ml in HBSS, 2-3 ml per round in the incubator at 37° C., for 10 to 15 minutes under gentle stirring. The supernatant was then centrifuged at 330-350 g for 8 minutes, resuspended in ice cooled HBSS. This procedure was repeated until the heart pieces were dissociated. The pooled cells were again washed, centrifuged at 330-350 g twice and resuspended in Dulbecco's Modified Eagle's Medium (DMEM) 4.5/M199 (4:1) (GibcoBRL) containing 10% horse serum (GibcoBRL) and 5% fetal bovine serum (FBS) (PAA Laboratories Inc., USA) with MycoZap (Lonza, Switzerland). The mesenchymal (adherent) fraction was separated from the cardiomyocytes and endothelial cells by two rounds of culture on plastic wells for 1 hour in incubator at 37° C., 5% $CO_2$ in 3% $O_2$. In order to follow the derivation of Isl1+ cells from the adherent fraction, these cells were labeled with the Isl1-gene construct containing the promoter for the Isl1-gene linked to the green fluorescent protein (GFP) gene (described above). This gene construct enables us to follow the derivation of Isl1+ cells directly in the culture dish. To stimulate the transformation of the mesenchymal cells into Isl1+ cells, the adherent fraction was detached using TrypLE™ Express (GibcoBRL) and recultured on plates coated with a thin layer of laminin 511, 521 or a combination of these, cultured in medium DMEM high glucose (GibcoBRL), MycoZap (Lonza), Hepes (25 mM) (GibcoBRL), glutamin (2 mM) (Fisher Scientific) and 15% FBS (PAA) in incubator at 37° C., 5% $CO_2$ in 3% $O_2$. At confluence (48 h), the cells were detached using TrypLE™Express (GibcoBRL) and recultured on plates coated with Laminin 511, 521 or a combination of these, in Wnt-medium containing DMEM/F12 supplemented with 1 ml B27 (GibcoBRL), 2% FBS (PAA), MycoZap (Lonza), epidermal growth factor (EGF, 10 ng/ml) (R&Dsystems, Minneapolis, USA), 2.5 mM BIO (Sigma-Aldrich, USA), Wnt 3a (100 ng/ml) (R&Dsystems). At confluence, the cells were passaged and recultured on wells coated with laminin 511, 521 or a combination of these, in the same medium. At each passage, cells were harvested for analyses described below. After two weeks treatment with the Wnt medium, the culturing process was finished and cells harvested for further analyses or injections.

Furthermore, we have also freezed and thawed adherent cells from different time points. Freezing of the cultured adherent cells was performed by detaching the cells and resuspending them after centrifugation in cooled Recovery™-cell culture freezing medium (GibcoBRL). The cells were transferred to storage vials and frozen gradually (−1° C. per minute) down to −70° C. and then transferred to liquid nitrogen (−180° C.). When the frozen cells were recultured, they were quickly thawed to 37° C., washed, and recultured on plastic plates coated with Laminin 511, 521 or a combination of these, in the same Wnt-medium and culturing conditions as described above.

Derivation and Expansion of Human Isl1+ Cells

Aspiration of bone marrow cells was carried out as previously described from young health human donors. Cord blood cells and amniotic cells were collected and isolated using standard conventional procedures. Abortion was performed according to a technique previously described by Westgren et al. (Acta Scand Obstet Gynecol 73, 601-604 1994)). The cardiac material was minced into small pieces and predigested over night as described for the rat embryonic hearts. The following procedures followed the same steps as for culturing of rat Isl1+ cells except that the preplating procedure was extended to 72 hours and performed in mesenchymal stem cell medium with DMEM low glucose (GibcoBRL), 10% FBS (PAA) and MycoZap (Lonza). As an alternative, culture medium free from non-human components may be employed, wherein the FBS is replaced by lyzed platelets obtainable from human blood. In order to follow the derivation of Isl1+ cells, the mesenchymal cells were labeled using the same Isl1-gene construct as for derivation of rat Isl1+ cells. To stimulate transformation into Isl1+ cells, we used similar culturing conditions as for rat Isl1+ cells with laminin 511, 521 or a combination of these as coating matrix, but with a Wnt-medium where BIO was excluded and serum level increased to 15% FBS (PAA)

(or lyzed human platelets at a suitable concentration). After each passage cells were saved for further analyses and after 2 weeks the culturing process was finished and cells harvested for immunohistochemical staining and micro-array analyses. The mesenchymal cells from different time periods were also freezed and thawed as described for the rat Isl1+ cells.

Immunohistochemical Analyses of the Cultured Isl1+ Cells

At each passage and at the end of the culturing process, cells were cytospinned and analyzed immunohistochemically for the presence of Isl1+ cells and also Ki67 to detect cell proliferation. The cytospinned cells were initially stored frozen, followed by fixation in 4% formaldehyde, blocked with serum, and incubated with the primary antibodies; Isl1: goat anti-human Isl1 (R&D systems); Ki67: mouse anti-rat Ki67 (clone MIB-5, DakoCytomation, Denmark) and direct-conjugated mouse anti-human Ki67-FITC (clone MIB-1, DakoCytomation) respectively. To visualize the unconjugated primary antibodies, the sections were washed and incubated with the fluorescence-labelled secondary antibodies; Isl1: Alexa Fluor 488 rabbit anti-goat (Molecular Probes, Invitrogen) and for Ki67: Alexa fluor 568 goat anti-mouse (Molecular Probes). Staining with control antibodies, as well as staining of negative and positive control tissues, was done to verify the specificity of all antibodies.

Expansion of the Human Mesenchymal Cells for Flow Cytometry Analysis

The human mesenchymal stem cells (MSCs) from different sources were prepared according to the same protocol as described above. Instead of changing to the Wnt-medium, the MSCs were maintained in DMEM high glucose (GibcoBRL), MycoZap (Lonza), Hepes (25 mM) (GibcoBRL), glutamin (2 mM) (Fisher Scientific) and 15% FBS (PAA) for five weeks at 37° C., humidified air containing 5% $CO_2$ and 3% Oz. Cells were passaged twice during this time, followed by flow cytometry. In order to test that the correct MSC was expanded, cells were transferred to wells coated with laminin 511, 521 or a combination of these, for continued culture for another two weeks in Wnt-medium, followed by immunohistochemical analysis of Isl1 expression.

Flow Cytometry

Approximately $0.85 \times 10^5$ cells per single staining were washed in PBS, centrifuged once at 300 g for 5 min and incubated at 4° C. for 30 min with appropriate amounts of antibody. The labelled cells were then washed in PBS as above. For characterization of the mesenchymal fraction we used the following panel containing fluorochrome-conjugated monoclonal antibodies (mAbs) against the human surface antigens: CD31 (WM59), CD34 (581), CD73 (AD2), CD44 (G44-26), CD14 (MoP9), CD19 (HIB19), CD105 (266) (all from BD Biosciences, San Jose, Calif.); HLA DR (Tu36), CD45 (H130) (Invitrogen) and CD90 (eBio5E10) (eBioscience Inc., USA). Each antibody-clone was titrated to optimal staining concentration using primary human samples. Data acquisition was done on a CyFlow ML (Partec GmbH, Munster, Germany), followed by data analyses with the FloJo software (TreeStar Inc., USA).

Laser Capture Microdissection (LCM)

Cryosections (7 μm) of whole rat embryos (GD 13), sliced in a transverse plane from head to tail and cryosections (7 μm) of a human embryonic heart (gestational week 9.5) and bone marrow-derived MSCs were collected onto sterile glass slides as well as on a 1-μm-thick PEN-Membrane-coated glass slides (Carl Zeiss, Germany). Targeted areas including both Isl1 positive and negative, were selected for capture using a 10× and 40× objectives. The negative regions were harvested from the developing left ventricle. Cryosectioning was performed using the 4-2-4-protocol, in which each slide was mounted with 3 sections. In using this protocol, two unstained membrane slides was preceded and followed by four cryosectioned slides, which were subsequently stained towards Isl1, using the same primary and secondary antibodies as for the cultured cells. These protocols aimed to histoanatomically localize the Isl1 positive and negative areas as well as generating high quality RNA yield. The micro-dissection process was performed through identifying the cells of interest, which in the next step were delineated and cut out through laser dissection. Equivalent Isl1 positive and negative areas were laser captured and total RNA isolated using the PicoPure RNA isolation kit (PicoPure RNA isolation kit, Arcturus Engineering, Invitrogen) following the manufacturer's protocol. The quantity and quality of the RNA were determined using 2100 Agilent Bioanalyzer, RNA 6000 Pico LabChip (Agilent, Palo Alto, Calif., USA). All RNA samples were stored under sterile conditions at −80° C. for future analysis. All safety handling measures to avoid RNA degradation were fulfilled.

Microarray Analysis

Total RNA from cultured rat and human Isl1+ cells was isolated using the PicoPure RNA isolation kit (PicoPure RNA isolation kit) following the manufacturer's protocol as described in the previous section. Equivalent amounts (about 2 ng) of purified total RNA from micro-dissected tissues as well as from cultured cells were reversely transcribed and amplified using the Ovation Pico WTA system (NuGEN Technologies, CA, USA) following the manufacturer's instructions. Sense strand cDNA was generated using WT-Ovation Exon Module (NuGEN Technologies). cDNA was fragmented and labelled using the Encore Biotin Module (NuGEN). Labeled cDNA were hybridized to Affymetrix Rat and Human Gene ST 1.0 microarrays (Affymetrix Inc, CA, USA) respectively. GeneChips were washed, stained and scanned using the Fluidic Station 450 and GeneChip Scanner 3000 7G (Affymetrix).

Preprocessing of the microarray data was performed in the Affymetrix Expression Console (v. 1.1) (Affymetrix Inc.) using the following methods: Summarization: PLIER; Background Correction: PM-GCBG; Normalization: Global Median.

Generation of Heatmaps

Heatmaps were created using QIucore Omics Explorer 2.2. Hierarchical clustering of both samples and variables was done using the Euclidean metric and data where each variable was normalized to mean 0 and variance 1. Average linkage and log 2 transformation of signals were used. The heatmap color scale range from red (high expression) via black (average expression) to green (low expression).

Anaesthesia and Postoperative Care

RNU rats (genotype rn/rnu, Charles River Deutschland Inc.) used for intramyocardial injection of labelled rat Isl1+ cells were anesthetized with a subcutaneous injection of Midazolam (Dormicum, 5 mg/kg) (Algol Pharma AB, Germany), Medetomidin hydrochloride (Domitor vet, 0.1 mg/kg) (Orion Corp., Espoo, Finland), Fentanyl (0.3 mg/kg) (B. Braun Medical AG, Seesatz, Switzerland) and subsequently endotracheally intubated to be able to perform the intramyocardial injections and induce myocardial infarctions described below. Positive-pressure ventilation was kept at a rate of 100 cycles per minute with a tidal volume of 4-5 ml with room air using a ventilator (7025 Rodent ventilator, UGO BASILE S.R.L., Italy).

The anesthesia was reversed by an intramuscular injection of Flumazenil (Lanexat, 0.1 mg/kg) (Hameln Pharma, Germany) and Tipamezol hydrochloride (Antisedan vet 5 mg/kg) (Orion Corp., Espoo, Finland). Postoperative analgesia was maintained by administrating Buprenorphin hydrochloride (Temgesic, 0.004 mg/kg/twice per day for 3 days) (Schering-Plough Corp., Belgium). Rats that showed signs of malfunction were excluded from the study.

Study of In Vivo Survival and Migration of Labeled Isl1+ Cells

The RNU rats were divided into four groups depending on how the Isl1+ cells were injected. In each experiment the hearts were exposed through a left thoracotomy. In the myocardial infarction groups, the left anterior descending artery (LAD) was permanently ligated and infarction induction was confirmed by color change and dyskinesia of the antero-lateral wall of the left ventricle. In each experiment 1 million labeled Isl1+ cells (obtained either from cardiac tissue or from the bone marrow) were used except for the intravenous experiment where 4 million cells were injected. Before injection, the Isl1+ cells were labelled with 2 µg pT2/C-fluc (Addgene, US), 2 µg pT2-β-gal and 1 µg SB 100× using the Neon™ Electroporation system (Invitrogen). In order to detect the cells after implantation into the myocardium, D-Luciferin (300 mg/kg) was injected intraperitoneally, followed by 15 min incubation. Bioluminescence imaging was in the next step performed in the IVIS®Spectrum CT (Perkin Elmer Inc.) using 5 min exposure and high sensitivity settings. The rats were imaged in a ventral position to be able to detect the expression of the transplanted cells and quantify the total flux using the Living Image Software (Perkin Elmer Inc.). The corresponding CT image was performed on a Quantum FX µCT (Caliper, Perkin Elmer Inc.) with 17 s scan time. The luminescent images were superimposed on the corresponding CT scan.

The rats were divided into the following groups: 1) injection into the left ventricular wall of a normal heart (n=4); 2) Injection into the peri-ischemic region of the left ventricle, directly after induction of a myocardial infarction (n=4). Cell survival and distribution were followed by IVIS (Perkin Elmer Inc.) and the hearts were harvested at 1 and 2 weeks for immunohistochemical analysis to confirm the IVIS data; 3) Injection into the left ventricular wall of a normal myocardium, followed three days later by induction of a myocardial infarction through a re-thoracotomy and LAD ligation (n=3); 4) Induction of a myocardial infarction followed by intravenous injection through the tail vein 8 hours after infarction induction (n=2). Since cell survival and distribution were found to correlate well with the IVIS signal, the animals in group 3 and 4 were only followed with IVIS for 1 week.

Detection of Rat Isl1+ Cells after Intramyocardial Injection

The hearts were harvested and freeze-sectioned into 7 µm thick sections. Hematoxylin and eosin stainings were used to get an overview of the different areas and subdomains of the hearts. From these sections, it was then possible to direct the X-gal staining to the regions of interest. The X-gal staning was done using a β-gal-staining kit (K1465-01) (Invitrogen) following the manufacturer's protocol.

Further Aspects of the Disclosure

1. A method for deriving a multipotent Isl1$^+$ cell, comprising the step of:
    (i) culturing a mesenchymal cell in the presence of at least one laminin comprising an α5 chain, and in a medium comprising at least one agent which activates the Wnt canonical pathway.
2. The method according to claim 1, wherein the mesenchymal cell is a cardiac mesenchymal cell, an embryonic or fetal stem cell, a cord blood stem cell, a bone marrow cell, and/or an amniotic stem cell.
3. The method according to any one of the preceding claims, wherein the at least one laminin comprising an α5 chain is selected from the group comprising laminin 511, laminin 521, and a combination of laminin 511 and laminin 521, and any synthetic, natural, or recombinant part or derivative or variant thereof.
4. The method according to any one of the preceding claims, wherein the at least one agent which activates the Wnt canonical pathway is selected from the group comprising Wnt-1, Wnt-3a, Wnt-8, Wnt-8b, and any combination thereof.
5. The method according to any one of the preceding claims, wherein the at least one agent which activates the Wnt canonical pathway is present at of concentration of 10-250 ng/ml.
6. The method according to any one of the preceding claims, wherein a second step (ii) further comprises expanding the Isl1$^+$ cell population.
7. The method according to any one of the preceding claims, further comprising a differentiation step, wherein the differentiation step comprises culturing the Isl1$^+$ cell in the presence of at least one laminin selected from the group comprising laminin 111, laminin 211, laminin 221, and any combination thereof.

What is claimed is:

1. A method for self-renewal of a multipotent Isl1+ cell, comprising the steps of:
   (i) culturing an Isl1+ cell in the presence of at least one laminin comprising an α5 chain, and in a medium comprising at least one agent which activates the Wnt canonical pathway; and,
   (ii) maintaining and/or expanding cells obtainable from step (i) in culture.

2. The method according to claim 1, further comprising a differentiation step, wherein the differentiation step comprises culturing the Isl1+ cell in the presence of at least one laminin selected from the group consisting of laminin 111, laminin 211, laminin 221, and any combination thereof.

* * * * *